United States Patent [19]
Wheelhouse et al.

[11] Patent Number: 6,087,493
[45] Date of Patent: Jul. 11, 2000

[54] PORPHYRIN COMPOUNDS AS TELOMERASE INHIBITORS

[75] Inventors: Richard Thomas Wheelhouse, Skipton, United Kingdom; Laurence H. Hurley, Austin, Tex.

[73] Assignee: Regents of the University of Texas System, Austin, Tex.

[21] Appl. No.: 09/018,545

[22] Filed: Feb. 4, 1998

Related U.S. Application Data

[60] Provisional application No. 60/037,295, Feb. 5, 1997.

[51] Int. Cl.$^7$ .................................................. C07D 487/22
[52] U.S. Cl. ............................ 540/145; 536/26.6; 435/6; 534/11; 534/15; 514/183; 514/184
[58] Field of Search .......................... 540/145; 536/26.6; 435/6; 534/11, 15

[56] References Cited

U.S. PATENT DOCUMENTS

| | | | |
|---|---|---|---|
| 5,595,726 | 1/1997 | Magda et al. | 424/9.61 |
| 5,622,685 | 4/1997 | Sinn et al. | 424/1.65 |

FOREIGN PATENT DOCUMENTS

| | | |
|---|---|---|
| 0345141 | of 1989 | European Pat. Off. |
| 0345171 | 12/1989 | European Pat. Off. |
| WO 93/00815 | 1/1993 | WIPO |

OTHER PUBLICATIONS

Butorin et al., "Optimization of synthesis conditions for oligonucleotide derivatives containing a hydrophobic porphyrin group on the 5'–ring," *Chemical Abstracts*, 121(11):1092, Abstract 134645q, 1994.

Hirota et al., "Preparation and characterization of bisviologen–linked porphyrin and bisviologen–linked zinc porphyrin," *Chemical Abstracts*, 120(25):863, Abstract 323040d, 1994.

International Search Report dated Jul. 8, 1998 (PCT/US98/02058) (UTFB:654P).

Kobayashi et al., "Electrochemical and spectroscopic studies of α, β, γ, δ–tetrakis–[1–(2–hydroxyethyl)pyridinium–4–yl]porphine and its metal complexes," *Bull. Chem. Soc. Jpn.*, 53(8):2195–2200, 1980.

Madakyan et al., "New water–soluble metal complexes of meso–tetrakis[3–N–(2'–hydroxyethyl)pyridyl]porphyrins and their pharmacological activity," *Chemical Abstracts*, 113(13):653, Abstract 114907h, 1990.

Qin et al., "Studies on kinetics of incorporation of metal ion into porphyrin. II. Reaction of manganese (II) with tetrakis(N–carbomethoxymethyl–3–pyridyl) porphyrin," *Chemical Abstracts*, 113(16):139558, Abstract 139563f, 1990.

Wheelhouse et al., "Carionic porphyrins as telomerase inhibitors: The interaction of tetra–(N–methyl–4–pyridyl)porphine with quadruplex DNA," *J. Am. Chem. Soc.*, 120(13):3261–3262, 1998.

Kobayashi et al., Bull. Chem. Soc. Jpn., 53., 1980 pp. 2195–2200.

Chem. Abst: 113: 114907h 1990 Madakyan et al.

Anatha and Sheardy, "Porphyrin binding to mult–stranded DNA,"*Biophys. J.,*Biophysical Society 41st Ann. Mtg, New Orleans, LA, 72:(2)A422, 1997.

Blackburn, "Structure and Function of Telomeres,"*Nature*, 350:569–573, 1991.

Anatha and Sheardy, "Porphyrin binding to mult–stranded DNA," *Biophys. J.*, Biophysical Society 41st Ann. Mtg, New Orleans, LA, 72:(2)A422, 1997.

Blasco et al., "Telomere shortening and tumor formation by mouse cells lacking telomerase RNA, " *Cell* 91:25–34, 1997.

Burger et al., "Inhbition of telomerase activity by cisplatin in human testicular cancer cell," *Eur. J. Cancer*, 33:638–644, 1997.

Chen et al., "XB596, a promising bis–naphthalimide anti––cancer agent," *Anti–Cancer Drugs*, 4:447–457, 1993.

Fletcher et al., "Human Telomerase Inhibition by 7–Deaza 2'–deoxypurine Nucleoside Triphosphates," *Biochem*, 35:15611–15617, 1996.

Georgiou et al., "Measurement of the Rate of Subcellular Localization of Porphyrins in Cells Using Fluorescence Digital Imaging Microscopy," *Photochem. Photobiol.,* 59:419–422, 1994.

Han and Hurley, "A Model for the T–Antigen–Induced Structual Alteration of the SV40 Replication Origin Based Upon Experiments with Specific Probes for Bent, Straight, and Unwounded DNA," *Biochem.,* 35:7993–8001, 1996.

Haq et al., "Molecular Anchoring of Duplex and Triplex DNA by Disubstituted Anthracene–9,10–diones: Calorimetric, UV Melting and Competition Dialysis Studies," *J. Amer. Chem. Soc.,* 118, 10693–10701, 1996.

Holt et al., "Lack of Cell Cycle Regulation of Telomerase Activity in Human Cells," *Proc. Natl. Acad. Sci. USA,* 94:10687–10692, 1997.

Kim et al., "Specific Association of Human Telomerase Activity with Immortal Cells and Cancer," *Science,* 266:2011–2015, 1994.

Kirk et al., "Block in Anaphase Chromosome Separation Caused by a Telomerase Template Mutation," *Science,* 275:1478–1481, 1997.

Lejnine et al., "Conserved Nucleoprotein Structure at the Ends of Vertebrate and Invertebrate Chromosomes," *Proc. Natl. Acad. Sci. USA,* 92:2393–2397, 1995.

(List continued on next page.)

Primary Examiner—Richard L. Raymond
Assistant Examiner—Pavanaram K Sripada
Attorney, Agent, or Firm—Arnold, White & Durkee

[57] ABSTRACT

The present invention has identified compounds with extended aromatic chromophores that bind the G-quadruplex formed by the folding of single-stranded human telomeric DNA. These compounds have been shown to be effective telomerase inhibitors and are contemplated to be useful in developing cancer treatments. A model of cationic porphyrin interaction with quadruplex DNA by intercalation has been established and in combination with structure activity relations has provided novel porphyrin compounds that exhibit discrimination between binding duplex and quadruplex DNA and show improved activity against telomerase.

29 Claims, 19 Drawing Sheets

OTHER PUBLICATIONS

Lingner et al., "Reverse Transcriptase Motifs in the Catalytic Subunit of Telomerase," *Sci.*, 276:561–567, 1997.

Lipscomb et al., "Structure of a DNA–Poprhyrin Complex," *Biochem.*, 35:2818–2823, 1996.

Mata et al., "A Hexameric Phosphorothioate Oligonucleotide Telomerase Inhibitor Arrests Growth of Burkitt's Lymphoma Cells *in Vitro* and *in Vivo*, "Toxicol *Appl. Pharmacol.*, 144:189–197, 1997.

Morin, "Is Telomerase a Universal Cancer Target?", *J. Natl. Cancer Inst.*, 87:859–861, 1995.

Norton et al., "Inhibition of Human Telomerase Activity by Peptide Nucleic Acids," *Nature Biotechnol.*, 14:615–619, 1996.

Parkinson, "Do Telomerase Antagonists Represent a Novel Anti–Cancer Strategy?" *Brit. J. Cancer*, 73:1–4, 1996.

Raymond et al., "Agents that target telomerase and telomeres," *Curr Opinion Biotech.*,7:583–591, 1996.

Salazar et al., "Thermally Induced DNA–RNA Hybrid to G–Quadruplex Transitions: Possible Implications for Telomere Synthesis by Telomerase," *Biochem* 35:16110–16115, 1996.

Strahl and Blackburn, "Effects of Reverse Transcriptase Inhibitors on Telomere Length and Telomerase Activity in Two Immortalized Human Cell Lines,"*Mol. Cell. Biol.*, 16;53–65, 1996.

Strahl and Blackburn, "The Effects of Nucleoside Analogs on Telomerase and Telomeres in *Tetrahymena*," Nucl. *Acids Res.*, 22:893–900, 1994.

Sun et al., "Inhibition of Human Telomerase by a G–Quadruplex–Interactive Compound," *L.H. J. Med. Chem.*, 40:2113–2116, 1997.

Weitzmann et al., "The Development and Use of a DNA Polymerase Arrest Assay for the Evaluation of Parameters Affecting Intrastrand Tetraplex Formation," *J. Biol. Chem.*, 271(34):20958–20964, 1996.

Wheelhouse et al., "Non–Nucleotide Telomerase Inhibitors: Structure–Based Design of G–Quadruplex Interactive Agents," *Proc. Amer. Assoc. Cancer Res.*, 38:637, 1997.

Zhu et al., "Cell Cycle–Dependent Modulation of Telomerase Activity in Tumor Cells," *Proc. Natl. Acad. Sci. USA*, 93:6091–6095, 1996.

Control  TMPyP4

PORPHYRIN COMPOUNDS AS TELOMERASE INHIBITORS

This application is a continuation-in-part of U.S. provisional patent application 60/037,295 filed Feb. 5, 1997.

The government has rights in the following invention pursuant to NCI Grant CA67760 and grant CA49751 from the National Institutes of Health.

1.0 BACKGROUND OF THE INVENTION

1.1 Field of the Invention

The present invention relates to porphyrin compositions and their use as telomerase inhibitors. More particularly, porphyrin analogs and derivatives are disclosed that interact with unique nucleic acid complexes formed during reactions catalyzed by telomerase.

1.2 Description of Related Art

Significant levels of telomerase activity have been detected in over 85% of tumors (Kim et al., 1994). Telomerase is also present in stem and germline cells of normal tissues, albeit at much lower levels (Morin, 1995). Thus, telomerase presents a target with potentially good selectivity for tumor over healthy tissue. Telomerase inhibition has been proposed as a new approach to cancer therapy (Morin, 1995; Parkinson, 1996; Raymond et al., 1996). The structure of the human telomerase protein remains elusive, although recently shown to be closely related to other reverse transcriptases (Linger et al., 1997). However, it has been possible to inhibit telomerase activity either by antisense strategies directed towards the telomerase RNA template, for example peptide nucleic acids (Norton et al., 1996) and phosphorothioate oligonucleotides (Mata et al., 1997) or by using inhibitors of reverse transcriptases [e.g., established agents such as AZT (Strahl and Blackburn, 1996) and other nucleosides (Fletcher et al., 1996)]. Inhibition by cisplatin, possibly due to crosslinking of the telomeric repeat sequences, has also been reported (Burger et al., 1997).

Telomerase is a specialized reverse transcriptase that contains its own RNA template for synthesis of telomeric DNA (Greider and Blackburn, 1989; Shippen-Lentz and Blackburn, 1990). The activity of this telomerase has been associated with cancer cells (Kim et al., 1994) and is thus a potential target for anticancer chemotherapy.

Telomeres consist of characteristic tandem repeats (TTAGGG in humans) found at the ends of most eukaryotic chromosomes (Blackburn, 1991). The stability and integrity of eukaryotic chromosomes depend on these genetic elements, which are synthesized by the ribonucleoprotein enzyme telomerase.

A mechanism for telomere synthesis by telomerase has been proposed by Blackburn and co-workers (Greider and Blackburn, 1989; Shippen-Lentz and Blackburn, 1990). In this mechanism, the processivity of telomere synthesis depends on translocation of the growing telomere. Although the exact mechanism of translocation is not yet well understood, this step appears to involve unwinding of the DNA:RNA hybrid formed by the extended telomere at the start site on the template. Since translocation can occur in the absence of a high-energy cofactor, it has been proposed that the formation of either G:G hairpin or G-quadruplex structures by the telomere product may provide the driving force for translocation (Shippen-Lentz and Blackburn, 1990; Zhaler et al., 1991).

The unique nucleic acid structures associated with telomeric DNA have been proposed as targets for the design of telomerase inhibitors (Zhaler, et al, 1991; Shippen-Lentz and Blackburn, 1990). Other studies on the unique DNA secondary structures adopted by telomeric DNA sequences have been reported (Fletcher, et al, 1996; Salazar, et al, 1996).

The telomeres are multiple tandem repeats of a highly conserved DNA sequence (in mammals 5'-TTAGGG-3') (SEQ ID NO:3) found at the ends of chromosomes and in human germline cells the telomeres may be 15–25 kilobases long. The telomeres are dynamic structures responsible for chromosome stability and have a role in control of chromosome separation and are thus involved in regulation of the cell cycle. The end replication problem means that with each cell division about 60–100 bases are lost from the ends of the chromosomes and as the telomeres shorten, cells eventually reach crisis and apoptosis is triggered. In immortal cell lines (tumors, germline and stem cells), an unusual enzyme activity—telomere terminal transferase, telomerase—is active which maintains the telomere length just above the crisis level. Whether telomerase activation is a cause or effect of the neoplastic state remains a matter of debate. However, the observation that telomerase is active in almost all tumor cells but not in most normal tissues does mean that telomerase presents a potentially highly selective target for the design of new agents to interfere with the growth of tumor cells.

2.0 SUMMARY OF THE INVENTION

The present invention provides porphyrin complexes and analogs that are effective in regulating telomerase function by interacting with G-quadruplex structure, particularly at the translocation step. The inventors have demonstrated that telomerase may be indirectly inhibited at the translocation step by ligands that either stabilize or disrupt G-quadruplex formation. Accordingly, G-quadruplex interactive compounds have been designed and demonstrated to have this effect. In vitro and in vivo studies have shown that these compounds are effective telomerase inhibitors and have an effect in modulating tumor proliferation and mortality in animal models.

G-quadruplex formation by the telomere product apparently is necessary for efficient translocation to occur. A wide range of compounds has been shown to be effective in this respect; all related to porphyrin and porphyrin analogs. Unexpectedly, these series of compounds show significantly less toxicity than other compounds that interact with DNA and that have some effect in disrupting or stabilizing G-quadruplex formation. Because the bound repeat must dissociate from the RNA template, the DNA:RNA hybrid to G-quadruplex transitions appear to provide at least part of the driving force for translocation by facilitating unwinding of the bound repeat.

A model of how cationic porphyrins could interact with quadruplex DNA by intercalation has been established. Structure-activity relationships (SAR) for a series of >60 porphyrins, analogues and complexes against telomerase are consistent with the intercalation model. The SAR and modeling data have been combined in the design of novel compounds to exhibit greater discrimination between binding duplex and quadruplex DNA and improved activity against telomerase.

In one aspect, the invention includes novel porphyrin compounds and analogs that inhibit telomerase. The compounds include aryl substituted porphyrins, with and without a chelated metal ion. The compounds are active as telomerase inhibitors whether or not the metal is present; however, presence of the metal offers advantages in that the compound is less photoreactive and thus is expected to show few photosensitivity effects when used in human therapies. Typically one would choose the metal ion from among the transition metals, preferably Ca, Sc, Mn, Fe, Co, Ni, Cu, Zn, Sr, Y, Ru, Pd, Ag, In, Ba, La, Pt, Au, Gd, or Eu and the numerous other metal cations shown in Table 4.

Certain examples of exemplary porphyrins that are useful as telomerase inhibitors include those designed to exploit the groove geometry of G-quadruplex. Known ligands, such as those shown, may be attached to the modified porphyrin shown where M is H⁺ or a metal cation such as Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb or Eu; m is 0–3, and X is O, NH or CO.

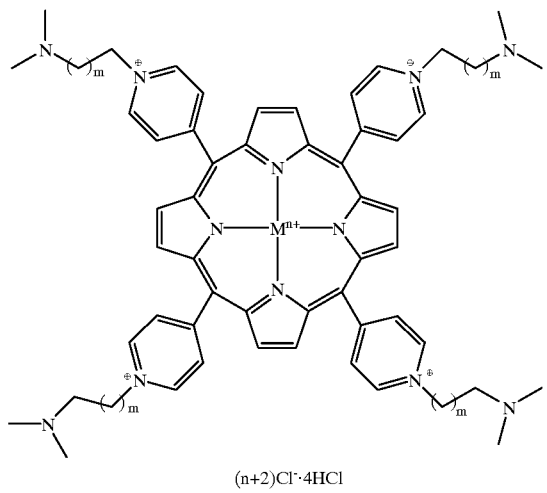

The ligand may be any of several groups as shown:

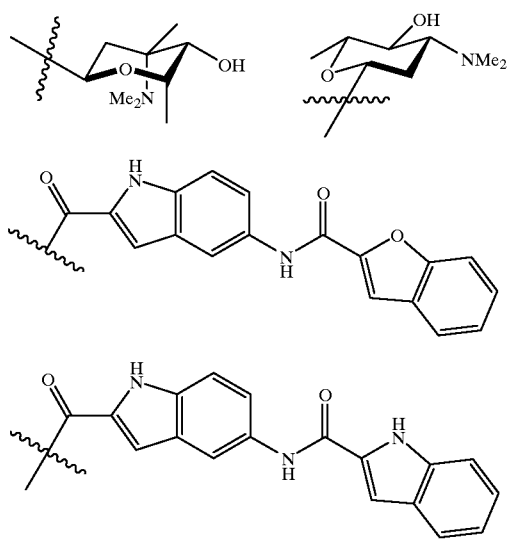

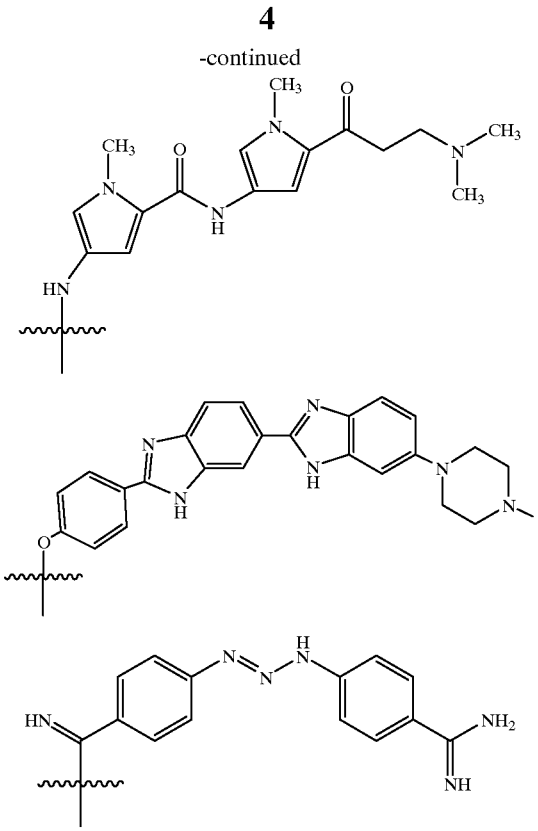

Other porphyrins are derivatives of porphyrin such as:

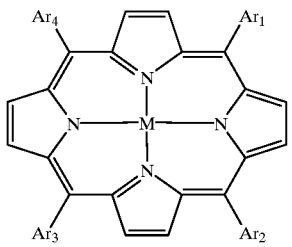

where M is a metal cation such as Ca, Sc, Mn, Fe, Co, Ni, Cu, Zn, Sr, Y, Ru, Pd, Ag, In, Ba, La, Pt, Au, Gd, or Eu, it being understood that an appropriate anion such as chloride, acetate, isothionate, citrate, etc. is present, preferably one suitable for use in pharmaceutical preparations.

$Ar_1$, $Ar_2$, $Ar_3$ and $Ar_4$ may be independently selected from aryl groups such as

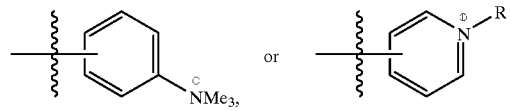

where R is H, lower alkyl, —$CH_2CH_2OH$, $CH_2OAc$, or —$CH_2CH_2CH_2SO_3^-$,

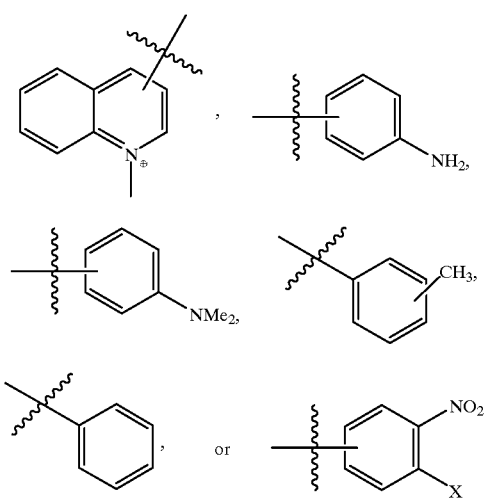
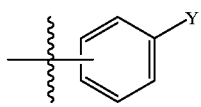
where X is H, OH, OMe, Cl or Me,
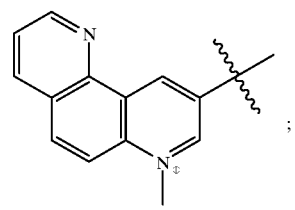
where Y is —CO$_2$H, CONH$_2$, CONHCH$_2$CH$_2$Br or NHCOCH$_3$,
Other groups may be attached to the porphyrin, including the following:
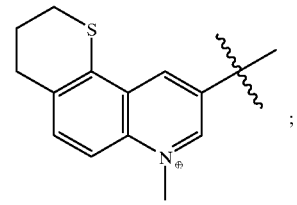
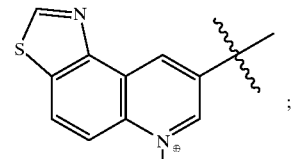
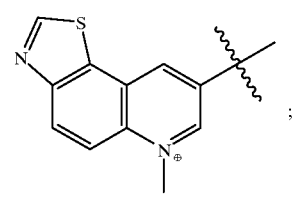
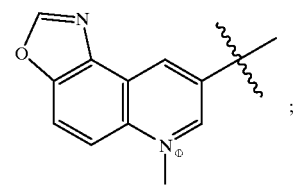
-continued
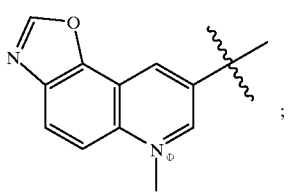
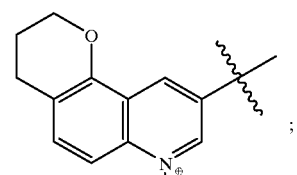
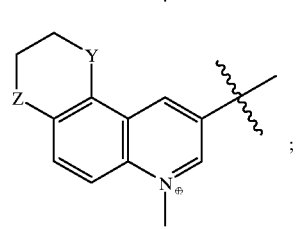

-continued
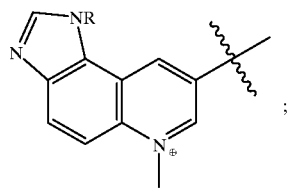
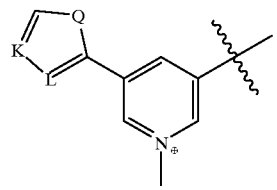
where R is lower alkyl, Y and Z are independently CH, NH, NMe, O or S;
or where Ar₁, Ar₂, Ar₃ and Ar₄ are independently;
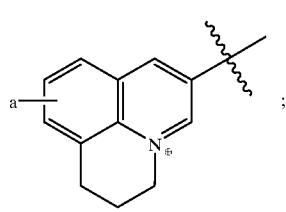
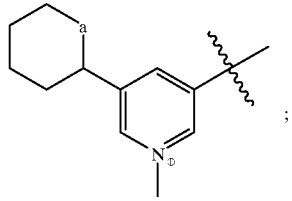
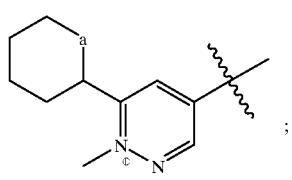
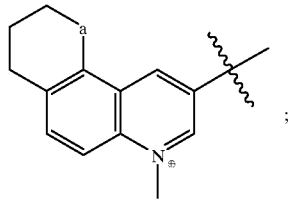
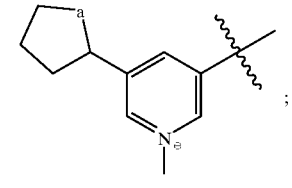
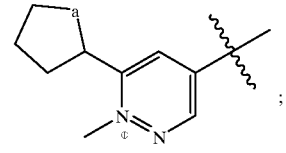
-continued
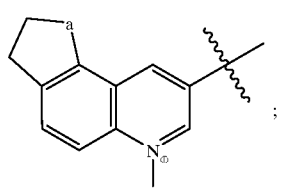
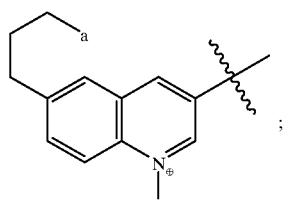
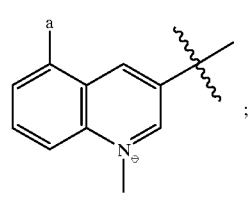
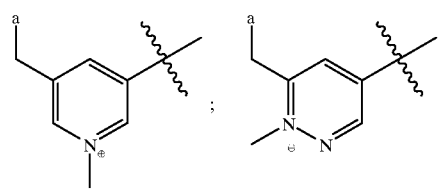
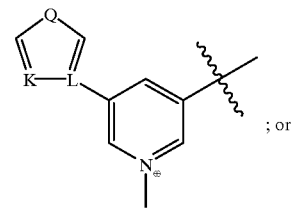
Where Q = O, S, NH or NMe
K = CH or N
L = N or CH or
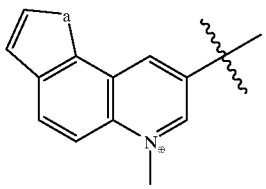
where a is NH, NH₂, NHMe, NMe₂, NMe, OH, OMe, SMe, O or S Ar₁, Ar₂, Ar₃ and Ar₄ may be independently;
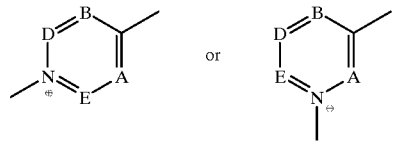
where A, B, D and E are independently N or CH; or where Ar₁, Ar₂, Ar₃ and Ar₄ are independently

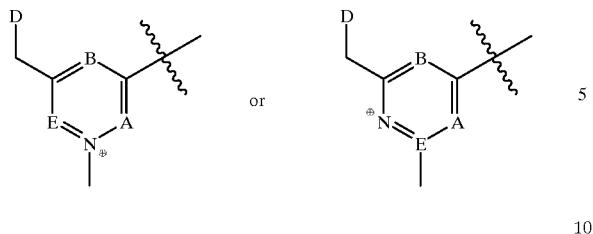

where A, B and E are independently N or CH and D is NH$_2$, NHMe, NMe$_2$, OH, SH, SMe or CF$_3$.

In further aspects, the invention includes additional porphyrin related compounds such as pyridyl and quinolyl porphyrins, which may be synthesized by the methods disclosed in the illustrative examples herein and by well-established chemical steps known to those skilled in the art. As used herein, it is understood that porphyrin is intended to apply to numerous analogs and derivatives of porphyrin, such as substituted porphyrins, particularly the porphines disclosed herein and quaternary salts thereof.

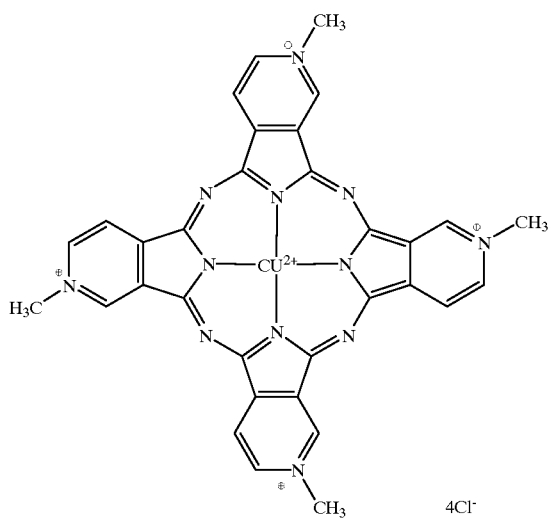

An important aspect of the invention is the use of porphyrin compounds as telomerase inhibitors. In one manner of use, a porphyrin compound such as one or more of those disclosed, is allowed to interact with telomeric DNA. The amount of the compound used to achieve such an effect has been found to be significantly lower than the toxic dose that may cause cell death. Thus such compounds are attractive candidates for human therapy, particularly in cancer treatment.

In further aspects, the invention includes a method of cleaving telomeric DNA. The telomeric DNA is contacted with a suitable porphyrin derivative, such as where a Fe.EDTA group is attached to the porphyrin. Such metal chelators are recognized as being effective in cleaving up to several nucleotide bases from the single strand telomere ends. The compound shown below is an example. Other cleaving groups include Ce(IV).EDTA and ene-diynes. Alternatively, addition of a cleaving group is not necessary as in some cases an appropriate metal may cleave the DNA, such as the following compound:

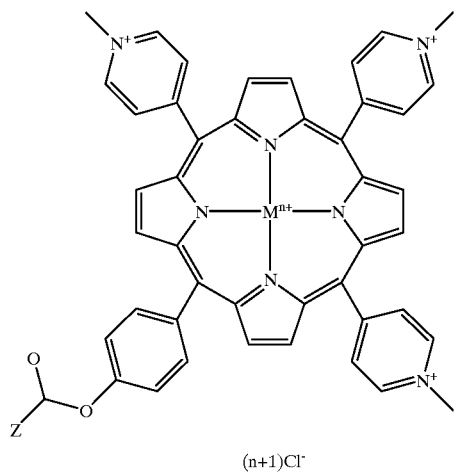

where Z may be Fe.EDTA or similar cleaving groups.

Yet another aspect of the invention is a method of covalently modifying telomeric DNA. This also may be achieved with selected porphyrin derivatives where Z is an alkylating agent such as:

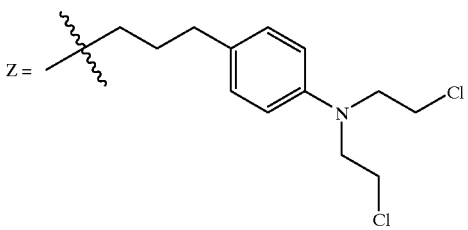

Other alkylating agents include imidazotetrazinones, cyclopropylimidazoles, cis-dichloroplatinum, epoxides, nitrosourea and aziridines.

Cationic porphyrins have been identified which are effective inhibitors of human telomerase. From data pertaining to a wide range of analogues a basic SAR has been determined, viz: the face of the porphyrin must be available for stacking; the positively charged substituents are important such that 4$^+$>3$^+$, 2$^+$ trans>2$^+$cis>1+; substitution is only tolerated on the meso positions of the porphyrin and the size of the substituents should to be matched to the width of the grooves in which they lie. These factors are all consistent with a model in which the porphyrins stack externally on the G-tetrads of quadruplex, placing the meso substituents in each of the four grooves.

The cationic porphyrins represent a promising class of compounds for the development of clinical telomerase inhibitors. For a compound to be useful it must have a significant therapeutic window between its activity against telomerase and the onset of cytotoxic effects. This is clearly so with the porphyrins; for example, TMPyP4 has cell free telomerase IC$_{50}$ about 12 μM but its cytotoxic IC$_{50}$ against a panel of normal and transformed breast and prostate cell lines is in the range 50–200 μM. Furthermore, evidence exists for the uptake and concentration of TMPyP4 in the nuclei of cells grown in culture and for its accumulation in tumor tissue in mice. Thus the cationic porphyrins have a number of properties that render them attractive candidates for development as telomerase inhibitors for the treatment of patients with cancer. The data indicate the potential for drug development to achieve the dual aims of efficacy and selectivity in vivo. This is supported by the use of TMPyP4 in mice implanted with MX-1 mammary carcinomas in which treated animals showed improved survival and decreased tumor growth compared to controls.

The validity of telomerase as a selective target for drug therapy has recently been questioned. In mice deficient in telomerase RNA it was found that the absence of telomerase activity and consequent severe shortening of telomeres did not reduce the tumorigenicity of murine cells (Blasco et al, 1997). The inventors have found that cellular effects following administration of TMPyP4 may not only be related to telomerase inhibition but also to disruption of other G-quadruplex structures, leading to more rapid onset of chromosomal instability, cell senescence and other consequences of telomere malfunction than could be accounted for by consideration of telomerase inhibition and concomitant telomere shortening alone.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. The reaction cycle of telomerase.

FIG. 2. Minimized model of a 2:1 complex between TMPyP4 and the $d(AG_3[T_2AG_3]_3)$ quadruplex.

FIG. 3. Rapid assay data for the inhibition of telomerase by porphyrins at 37° C. TAP is tetra(N,N,N-trimethyl-4-aminophenyl)porphyrin chloride; TMPyP4 is tetra(N-methyl-4-pyridyl)porphyrin. Data are shown for a series of transition metal complexes of TMPyP4. C-100% represents the control (no inhibitor); C-0% is the negative control. All porphyrin concentrations were at 100 $\mu$M.

FIG. 4A. The concentration dependence of effect of tetra(N-methyl4-pyridyl)porphyrin on telomerase activity in MCF-7m breast tumor cells. Cells were grown in the continuous presence of porphyrin and for each data point 20 million viable cells were taken, washed, lysed and the telomerase activity of the extract assayed using a standard assay.

FIG. 4B. The time dependence of effect of tetra(N-methyl4-pyridyl)porphyrin on telomerase activity in MCF-7m breast tumor cells. Cells were grown in the continuous presence of porphyrin and for each data point 20 million viable cells were taken, washed, lysed and the telomerase activity of the extract assayed using a standard assay.

FIG. 5A Inhibition of human telomerase by TMPyP4. Effect of TMPyP4 on the ladders produced by telomerase extension of an 18-base primer. Lanes 1–5 contained 0, 2.5, 5, 10, 25 $\mu$M TMPyP4 respectively; the roman numerals to the left of the gel indicate the number of $T_2AG_3$ repeats.

FIG. 5B. Inhibition of human telomerase by TMPyP4. Graphical determination of the $IC_{50}$.

FIG. 6A. Structures of TMPyP4.

FIG. 6B. Structure of a G-tetrad.

FIG. 6C. Model of TMPyP4 stacking with human telomeric complex.

FIG. 7A. Inhibition of telomerase extension of an 18-base primer by porphyrins and metalloporphyrin complexes. Effects of increasing concentrations of porphyrin on the telomerase ladder.

FIG. 7B. Inhibition of telomerase extension of an 18-base primer by porphyrins and metalloporphyrin complexes. Concentration dependence of telomerase inhibition by porphyrins.

FIG. 8. Cytoxic effects of porphyrins against normal (Hs578Bst) and transformed (HS578t) human breast cells.

FIG. 9A. Long-term inhibition of telomerase activity by a porphyrin TMPyP4 in intact MCF7 human breast carcinoma cells. Autoradiogram for the telomerase activity assay in MCF7 cells extracts;

FIG. 9B. Long-term inhibition of telomerase activity by a porphyrin TMPyP4 in intact MCF7 human breast carcinoma cells. Concentration-dependence of telomerase activity inhibition.

FIG. 9C. Long-term inhibition of telomerase activity by a porphyrin TMPyP4 in intact MCF7 human breast carcinoma cells. Time-dependence of telomerase inhibition by TMPyP4.

FIG. 10. Cell cycle analysis in MCF7 cells treated in culture with 100 $\mu$M TMPyP4.

FIG. 11. Nuclear incorporation of QP3.In$^{III}$ into intact MCF7 human breast carcinoma cells.

FIG. 12 Chromosomal destabilization induced by by 100 $\mu$M TMPyP4 in sea urchin embryos.

FIG. 13A. DNA synthesis arrest by intramolecular quadruplex formation in a single-stranded template beating four telomeric repeats Effect of increasing the concentration of TMPyP4.

FIG. 13B. DNA synthesis arrest by intramolecular quadruplex formation in a single-stranded template beating four telomeric repeats Effect of increasing temperature in the absence and presence of TMPyP4. The arrow marks the 5'-end of the telomeric sequence.

4.0 DETAILED DESCRIPTION OF ILLUSTRATIVE EMBODIMENTS

Human telomerase and its associated nucleic acid structures represent novel, cancer-specific targets for the development of new therapeutic agents. Human telomeric DNA consists of tandem repeats of the sequence 5'-TTAGGG-3' (telomeres) and can adopt a number of secondary structures that are essential for the functioning of telomerase, the enzyme that synthesizes the telomeres.

Telomerase is a specialized reverse transcriptase that carries its own RNA template. The structure of the telomerase protein remains elusive (although recently shown to be related to other reverse transcriptases (Lingner et al., 1997) and in consequence, the design of telomerase inhibitors has hitherto been restricted to anti-sense strategies directed towards binding or cleaving the template sequence of the telomerase RNA (oligodeoxyribonucleotides (Feng et al., 1995), peptide nucleic acids (Norton et al., 1996), phosphorothioate oligonucleotides (Mata et al., 1997) or established strategies for inhibiting reverse transcriptases; for example, nucleoside analogues such as AZT (Strahl and Blackburn, 1994) and 7-deazaguanosine (Fletcher et al., 1996).

The cartoon in FIG. 1 outlines the reaction cycle of telomerase (based on Zahler et al.). A DNA primer attaches to the binding region of the template RNA (A) and is extended by six bases (B) thus generating an enzyme-bound DNA-RNA heteroduplex. Since the template region of the RNA includes only 1.5 repeats of the telomere sequence it is necessary for the extended telomere to be shifted back to the beginning of the template—the translocation step—which produces a single-stranded G-rich DNA (C). The translocation appears to be independent of high-energy co-factors. Thus there are at least three nucleic acid targets for drug design: the telomeric duplex, the RNA-DNA hybrid generated on the enzyme and the newly-formed single-strand.

A property of G-rich single-stranded DNA is that it may adopt quadruplex secondary structures. It has been shown that conditions which favor quadruplex formation ($K^+$) result in inhibition of telomerase. Other work has shown that where a DNA-RNA hybrid exists in equilibrium with a DNA quadruplex and free RNA the equilibrium lies towards formation of the quadruplex. These observations taken together suggested that quadruplex formation may provide at least part of the driving force for the translocation reaction, and that quadruplex itself may therefore be a target for the rational design of telomerase inhibitors.

Several compounds with extended aromatic chromophores that are able to bind the G-quadruplex formed by the folding of single-stranded human telomeric DNA have been identified. An assay using partially purified telomerase has shown that these compounds are effective telomerase inhibitors. Furthermore, there exists a significant threshold between telomerase inhibitor ($IC_{50}$~10 $\mu$M) and cytotoxicity ($IC_{50}$>100 $\mu$M) demonstrating the plausibility of developing relatively non-toxic telomerase inhibitors for in vivo and clinical use.

The inventors postulated that 5,10,15,20-tetra-(N-methyl-4-pyridyl)porphine (TMPyP4), was of appropriate size to stack with the G-tetrads that stabilize quadruplex DNA. This porphyrin has now been shown to interact with human telomeric quadruplexes, stabilize quadruplex DNA to thermal denaturation, and inhibit human telomerase in a cell-free system. In vivo studies indicate that TMPyP4 increases survival in adjuvant human breast tumor xenografts implanted mice.

The interaction of TMPyP4 with quadruplexes based on human telomeric sequences was investigated using a variety of techniques. In a series of one-dimnensional high-field NMR studies, TMPyP4 was titrated into solutions of parallel-stranded quadruplexes (Wang and Patel, 1992) formed by the sequences d(TTAGGG), d(TTAGGGTT), and d(TTAGGGTTA). Line broadening and chemical shift changes in the DNA resonances indicated that TMPyP4 was associated with the TTAG portion of the sequences. For example, upon titrating one equivalent of TMPyP4 into a solution of the quadruplex formed by d(TTAGGG), G4(NH1) shifted 0.7 ppm upfield, G5(NH1) shifted 0.2 ppm upfield, and G6(NH1) was unchanged. UV titration studies with the intramolecular quadruplex (Wang and Patel, 1993) d($AG_3[T_2AG_3]_3$) showed sharp isosbestic points, hypochromicity, and a marked red-shift. These data indicated a discrete mode of binding, strong stacking interactions and stoichiometry of two porphyrins per quadruplex. The UV and NMR data together strongly suggested that TMPyP4 binds to quadruplex DNA by stacking externally on the G-tetrads rather than by intercalating between them.

For the first time it has been shown that targeting G-quadruplex with effective G-quadruplex interactive agents is a sound strategy for the inhibition of telomerase activity in cancer cells. This finding is important because it demonstrates the validity of a rational, structure-based approach to the design of compounds that yield net telomerase inhibition. The fact that DNA, not telomerase protein or RNA, can be a target for rational drug design has important implications for development of a new class of telomerase inhibitors and methods for controlling cell proliferation.

The present work shows that cationic porphyrins inhibit telomerase, cause G2/M arrest, and lead to chromosomal destabilization, while not inducing significant telomere shortening. These effects might be expected from the G-tetraplex interactive agents interfering with the correct functioning of telomere structures.

The cationic porphyrins, particularly TMPyP4, are telomerase inhibitors at low micromolar concentrations. These porphyrins are relatively nontoxic to cells (both tumor and normal) at levels that can inhibit telomerase. Therefore, this class of G-quadruplex interactive compounds can selectively inhibit telomerase activity at concentrations that do not have general toxic effects on cells. The uptake and accumulation data demonstrate that the cationic porphyrins accumulate at useful levels (i.e. inhibitory to telomerase) in the nuclei of intact cells.

Long-term exposure of the human tumor cells to TMPyP4 leads to repression of telomerase activity. The repression is paralleled by a time-dependent increase in cell arrest at the G2/M phase. These results suggest that telomerase activity is different at various stages of the cell cycle, as proposed (Zhu et al., 1996). However, with not more than 32% of the MCF7 cells arrested in G2/M, only residual telomerase activity was measured. In the untreated controls a significant fraction of cells was in the G2/M phase (47%), yet the cells expressed telomerase. Therefore, a variation of telomerase activity in the cell cycle may not completely explain the observed decrease of telomerase activity. Another possibility is an indirect effect of TMPyP4 on downregulation of telomerase expression, recently postulated as a part of the mechanism of cisplatin action against human testicular cancer cells (Burger et al., 1997).

The first indication that TMPyP4 induces chromosomal abnormalities was found in sea urchin embryos. The inventors have shown that TMPyP4 significantly decreases proliferative rates in the developing embryos and increases the percent of the cell in mitosis leading to formation of largely elongated mitotic chromosomes. A similar phenotype was described in Tetrahymena with telomerase RNA template mutation (Kirk et al, 1997). In HeLa cells cultured in the presence of 3 $\mu$M TMPyP4 for 2–4 days the number of fused chromosomes was increased in comparison with the untreated controls. These chromosomal aberrations may be sufficient to inhibit cellular proliferation even in the absence of repression of telomerase activity.

Although the inventors' results suggest that TMPyP4 induces chromosome destabilization, telomere shortening in human tumor cells in vitro has not yet been demonstrated. This finding is not very surprising. Telomere shortening occurs at approximately 65–100 base pairs per cell division (Counter et al., 1992). At this rate of telomere loss, even with relatively short telomeres in MCF7 cells, a longer time in culture (>20 population doubling time) in the presence of the porphyrins may be required to achieve significant effects on telomere length. Moreover, telomeres have been shown to play a direct role in mitosis—a physical block in anaphase chromosome separation is caused by telomerase template mutation (Kirk et al., 1997). An implication of this finding is that porphyrins (as telomere-interactive agents) may arrest the cells in mitosis and thus abrogate telomere shortening. In support of this notion, the inventors have observed an increase of the G2/M fraction in MCF7 cells treated with TMPyP4.

Telomere shortening may not be a paradigm for telomerase inhibitors. Highly variable telomere lengths in two immortalized cell lines treated with reverse transcriptase inhibitors supposedly were a result of telomerase-dependent and telomerase-independent mechanisms for telomere maintenance (Strahl and Blackburn; 1996). Therefore, agents like TMPyP4 which repress telomerase activity and can directly interact with telomeres, may be effective in situations where telomere length in tumor cells is maintained by telomerase-independent mechanisms.

It has been suggested that the ideal preclinical and clinical trial models for evaluation of telomerase inhibitors will be tumors in which high telomerase activity is accompanied by short telomeres (<7 kilobases) (Raymond et al., 1996). In such tumors, end-points related to telomere malfunction or shortening would be reached sooner than in those with long telomeres or telomeres maintained by mechanisms not related to telomerase. In the present work, it has been shown that the G-quadruplex interactive agents directly interact with telomeres and rapidly evoke antiproliferative effects in tumor cells. Telomerase repression may be a secondary event to tumor growth arrest. Thus, the G-quadruplex interactive agents which represent a different mechanism of action than other telomerase inhibitors may be most effective in tumors with low telomerase activity.

The present work provides a basis for developing methods using small-molecule telomerase inhibitors targeting telomeric DNA rather than telomerase per se. The rapid cell response to G-quadruplex interactive agents, even without observed telomere shortening, indicates greater significance and multiple roles for G-quadruplex in the whole telomere system. A recent report describing telomere shortening and tumor formation by mouse cells lacking telomerase RNA (Biasco et al., 1997) raises questions regarding the validity of telomerase as a target for anticancer agents. Thus the strategies herein disclosed focusing on telomere interactive agents opens a new approach to developing G-quadruplex interactive agents for specific anticancer therapies.

4.1 Models for Identification of G-quadruplex Interactive Compounds

The present invention is based in part on the notion that extended chromophores might thread, and thereby stabilize, quadruplexes. The inventors selected 5,10,15,20-tetra-(N-methyl-4-pyridyl)porphine, TMPyP4, as being of appropriate size to stack with the G-tetrads of quadruplex DNA. The crystal structure of a complex of this porphyrin with a short duplex has recently been determined and has two notable features: the porphyrin is too large to fully intercalate so only fits about half-way into the duplex and this is accompanied by considerable disruption of the helical structure adjacent to the hemi-intercalation site.

The solution structure of human telomeric G-quadruplex DNA, d(AG$_3$[T$_2$AG$_3$]$_3$) has been determined (Wang and Patel, 1993). It is an intramolecular fold-over structure that is stabilized by three guanine tetrads, stacked at its center. FIG. 7 shows the structure of the cationic porphyrin TMPyP4 FIG. 7(A) and a G-tetrad FIG. 7(B). The interaction of TMPyP4 with duplex DNA has been the subject of much work. The X-ray crystal structure of this porphyrin with a short duplex has been solved (Lipscomb et al., 1996). This structure has two notable features: the porphyrin only fits halfway into the duplex and there is extensive disruption of the bases adjacent to the intercalation site. The inventors have built a model to assess how many TMPyP4 molecules may complex with the human telomeric quadruplex, FIG. 7C. The model shows that TMPyP4 is a good fit for stacking with G-tetrads where it can be oriented to place each of the cationic N-methylpyridine groups into each of the four grooves of the quadruplex. A section through the minimized model of the 2:1 complex between TMPyP4 and the intramolecular quadruplex formed by the sequence d(AG$_3$[T$_2$AG$_3$]$_3$) shows that TMPyP4 may stack on the G4 G8 G16 G20 tetrad.

Investigations with quadruplexes indicated that TMPyP4 bound in the loop regions of quadruplexes and stacked externally on the tetrads rather than opening up a true intercalation site. This complexation stabilized quadruplex to thermal denaturation. The solution structure for a twenty-two-base oligonucleotide based on the human telomere sequence, d(AG$_3$[T$_2$AG$_3$]$_3$), (SEQ ID NO:9), consists of a single looped strand which is stabilized by a core of stacked G-tetrads. Using the coordinates from the crystal structure of the porphyrin and the solution structure of the quadruplex, a minimized model of how the two might interact was built, FIG. 2. The quadruplex can accommodate porphyrins above and below the tetrads at the core of the complex with very little distortion. The porphyrins lie stacked on the tetrads and can be orientated so that the positively-charged groups were directed into the grooves towards the sugar-phosphate back bone. A number of analogues of TMPyP4 were obtained and assayed for activity against telomerase. A structure activity relationship was observed, consistent with a mechanism of action involving stacking.

The present invention is a novel approach to achieve the net inhibition of telomerase by targeting its substrate, the telomere. A rational, structure-based approach to the design of telomere interactive agents was employed by considering unique nucleic acid secondary structures associated with the telomerase reaction cycle. One such structure is the G-quadruplex formed by folding of the single stranded G-rich overhang produced by telomerase activity. The template region of the telomerase RNA has only 1.5 copies of the complementary sequence (3'-CAAUCCCAAUC-5', (SEQ ID NO:8) so after each extension, the end of the DNA must be translocated back to the beginning of the of the coding region prior to the next extension (Blackburn, 1991). Translocation occurs without consumption of high energy cofactors. Other work has shown that potassium ions stabilize the quadruplex and that high concentrations of potassium inhibit telomerase (Zahler et al., 1991). Furthermore, the inventors have shown that there is an equilibrium between the DNA:RNA heteroduplex and the G-quadruplex that lies in favor of G-quadruplex formation (Salazar et al., 1996). These observations point to the involvement of G-quadruplex formation in dissociating the primer from the telomerase or RNA template and possibly providing the driving force for the translocation reaction. Thus the inventors hypothesized that the G-quadruplex would be a viable target for drug design as first suggested by Blackburn (Blackburn, 1991).

An objective of the inventors' studies was to identify effective G-quadruplex interactive agents (with significant concentration differences between telomerase inhibition and the cytotoxic effects). Herein the inventors describe the inhibition of telomerase by TMPyP4, the related tetraquinolyl porphine QP3, and several metal complexes. The cytotoxicity and cellular uptake of this family of porphyrins have been examined in a series of human tumor and normal cell lines. The inventors have demonstrated that rapid repression of telomerase activity and cell growth arrest in intact tumor cells by subtoxic concentrations of TMPyP4 is achievable without significant telomere shortening. This finding suggests that the use of effective G-quadruplex interactive agents to directly target telomeres and to destabilize DNA as a possible therapeutic strategy. Three tumor models (breast, prostate, and lymphoma) are relevant to the future clinical development of telomerase inhibitors. The low cytotoxicity and inhibition of telomerase at low micromolar concentrations combine to make the cationic porphyrins attractive candidates for anticancer drug development.

4.2 Telomerase

Telomerase is a specialized reverse transcriptase which carries an internal RNA template for the synthesis of highly conserved DNA tandem repeats (telomeres) at the ends of eukaryotic chromosomes. The telomeres are responsible for maintaining the stability and integrity of chromosomes necessary for sell survival. Telomerase offers a selective target for cancer since, with few exceptions, only cancer cells have detectable levels of this enzyme. Without telomerase, the telomeres of immortalized cancer cells would shorten with each cell division, eventually leading to chromosomal instability and cell death. While little is known about this enzyme, particularly the human form, it was proposed (Shippen-Lentz and Blackburn, (1990)) (Zhaler, et al. (1991)) that it is possible to design telomerase inhibitors based upon what is known about the mechanistic aspects of the enzyme and its associated nucleic acid structures. However, while G-quadruplex has been suggested as a target for drug design, there has been no guidance on what classes of compounds might be effective in at this site that would be effective in modifying telomerase or telomere activity.

The present invention shows that the cationic porphyrin TMPyP4 binds strongly to DNA quadruplexes relevant to the functioning of telomerase by stacking on the G-tetrads at the core of the quadruplex. The binding results in stabilization of the quadruplex, a phenomenon that has previously been linked to inhibition of telomerase. TMPyP4 is an effective inhibitor of human telomerase in HeLa cell extract.

The validity of telomerase as a selective target for drug therapy has recently been questioned. In mice deficient in telomerase RNA, it was found that the absence of telomerase activity and consequent shortening of telomeres did not reduce the tumorigenicity of murine cells (Blasco et al., 1997). However, the inventors have found that cellular effects following administration of TMPyP4 may not only be related to telomerase inhibition but also to disruption of other G-quadruplex structures, leading to chromosomal instability and cell senescence.

4.3 Porphyrins as G-quadruplex Interactive Agents and Telomerase Inhibitors

Several series of porphyrin derivatives, analogues and metallo-porphyrin complexes have been screened through a telomerase assay. In the metallo-porphyrin series, the level of inhibition shows a correlation with the coordination chemistry of the metal. Square-planar complexes, which are known to intercalate duplex, give the greatest inhibition while octahedral complexes with strongly bound axial ligands that, in the case of duplex are unable to intercalate, show less activity against telomerase. Pasternack (1983) and Ward, et al (1986) have discussed the interaction of cationic porphyrins, and their complexes, with duplex DNA.

Using a standard assay to observe the telomerase extension ladders, it was noted that the uncomplexed porphyrins and certain metal complexes gave blurred bands and ill-defined high molecular-weight material. By running the assays in the dark, these anomalies in the gel were shown to be due to photosensitization. This depended on the d-electron configuration of the metal; unpaired d-electrons quenched the excited state of the porphyrin and prevented light-induced damage to DNA. This demonstrated the need to identify a metal ion that forms a stable, square-planar complex with porphyrins, has an unpaired d-electron, and is non-toxic.

Another significant result is that the inhibition of telomerase is always seen after the first extension of the primer, which itself consists of three telomere repeats; thus telomerase inhibition is only seen when the DNA is able to fold into a quadruplex loop.

A wide range of different porphyrin structures and analogues has been tested, (see Tables 4–15) and some structure activity relationships for activity against the isolated enzyme have been determined, including:

1. Positive charges are essential for activity;
2. Substituents should be placed on the meso positions of the porphyrin;
3. Pyrrole rings should not be substituted;
4. Meso substituents should bear an electron withdrawing group.

4.4 Cytotoxicity

Table 1 shows preliminary cytotoxicity data two porphyrins against a variety of breast tumor cell lines in vitro. Also shown is the activity against telomerase ($IC_{50}$~10 $\mu$M).

Table 1 shows the in vitro evaluation of cytotoxicity of cationic porphyrins in human tumor cell lines and normal fibroblast cells. The cells were cultured in the presence of the porphyrins incubator for 4–7 days and then treated with 3-(4,5-dimethylthiazol-2-yl)-2,5-diphenyl-tetrazolium bromide (MTT). Formazan concentration was quantitated by absorbance at 570 nm.

TABLE 1

| | In Vitro Evaluation of Cytotoxicity IC 50 ($\mu$M) | | | | | | |
|---|---|---|---|---|---|---|---|
| Cell Line | TMPyP4 | TMPyP4(Pt) | TMPyP3(Cu) | TMPyP4(In) | QP3 | QP3(Cu) | QP3(In) |
| Breast | | | | | | | |
| MCF-7 | 49.6 | >100 | 47.8 | >100 | 212.0 | >100 | 134.2 |
| MDA-231 | 44.0 | >100 | 220.5 | 390.1 | 597.0 | 226.0 | 116.5 |
| BT-20 | 106.4 | 261.7 | 9.8 | 160.8 | 81.4 | 20.4 | 79.1 |
| Prostate | | | | | | | |
| PC3 | 184.0 | >200 | 384.7 | >200 | 304.7 | >100 | 111.5 |
| DU145 | 93.6 | 1356.6 | 90.7 | 1166.6 | 323.3 | 40.9 | 27.1 |
| LNCap | 22.8 | 42.2 | 126.4 | 62.2 | ND | ND | ND |
| Lymphoma | | | | | | | |
| Daudi | 3.1 | 103.5 | ND | 5.3 | 34.0 | ND | ND |
| Raji | 11.9 | 64.6 | 69.7 | 43.7 | ND | ND | ND |
| Normal | | | | | | | |
| NHLF | 13.5 | 11.6 | 228.1 | >100 | 191.2 | 4.9 | 86.2 |

4.5 Uptake and Inhibition of Telomerase in Whole Cells

In proposing a structure for the development of a new drug it is important to show that it is possible for the compound to reach its cellular target. The uptake and distribution of cationic porphyrins is cultured fibroblasts has been monitored by fluorescence microscopy (Georgiou, et al., 1994). While uptake was shown to be highly charge dependent, such that 2+>>3+>4+, tetra(N-methyl-4-pyridyl) porphyrin was taken up by cells and localized in organelles known to contain DNA.

The effect of chronic exposure breast tumor cell lines to tetra(N-methyl-4-pyridyl)porphyrin is shown in FIG. 4A and 4B. This shows that telomerase activity is reduced relative to control cells and that this reduction in activity is both dose and time dependent.

4.5 Design and Synthesis of Novel Porphyrins

The structure activity relationship (SAR) and modeling data described above make an initial assumption that the disclosed porphyrins likely interact with G-quadruplex. This provides a basis for the design of new compounds with both increased binding constants and selectivity for quadruplex, and thus increased activity against telomerase. DNA quadruplex presents a unique structure with significant differences from duplex DNA. Firstly, steric accessibility of the grooves: one wide, one narrow and two medium width grooves. Secondly, the hydrogen bonding potential of groups in the base of the grooves. The symmetry of the G-tetrads results in all four grooves having the same hydrogen bonding group: one guanine-N(2)H per tetrad in each groove; significantly less hydrogen bonding potential than found in duplex.

There are three approaches to the design of novel porphyrin telomerase inhibitors:

(i) Simple Porphyrins

The tetra(N-methyl-4-pyridyl)porphyrin skeleton presents an appealingly elegant and simple structure. The effects of a number of cationic and uncharged hydrophilic groups on the activity against telomerase are contemplated to provide additional support for the design of porphyrin compounds that act effectively as telomerase inhibitors. Simple variations of pyridinium/quinolinium structures and their syntheses are outlined in Scheme 1. While the isolated enzyme assay has shown that optimally four positive charges are required on the porphyrin, it is possible that these may pose cellular uptake problems in vitro and absorption problems in vivo. Synthesis may be adapted to prepare 2+ or 3+ analogs which may address these problems.

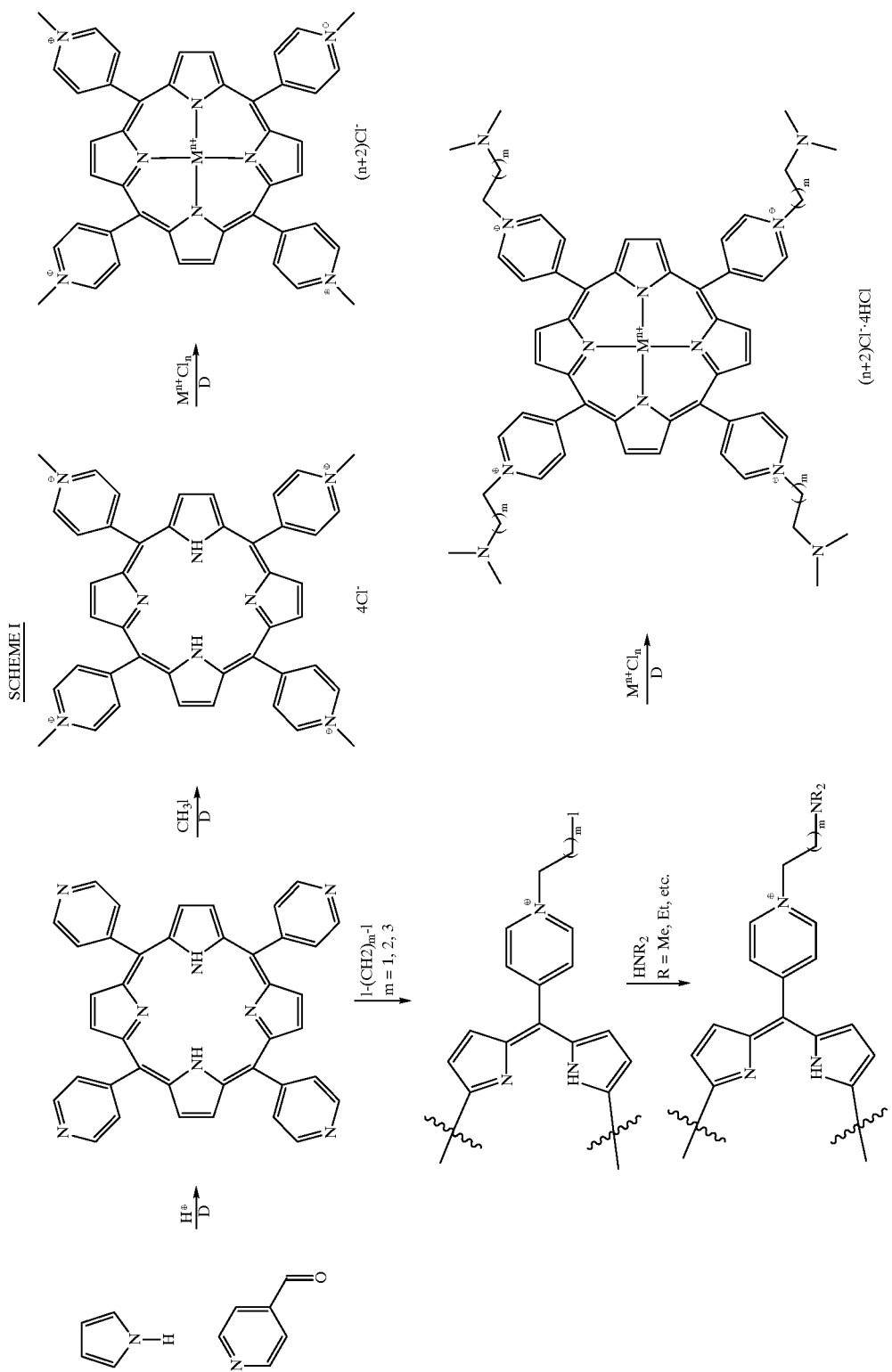

(ii) Exploitation of the Different Groove Widths

Selectivity in binding can be achieved by the use of groove-binding ligands with strong steric preferences. There is precedent in the literature for achieving selectively between duplex and triplex binding by attaching groove binding ligands at the ends of an appropriately sized aromatic chromophore (Haq, et al., 1996). The porphyrin skeleton will be used to build such compounds using ligands such as Hoechst compound 33258 (which in duplex selects for the wide minor groove of GC-rich duplex) and netropsin (which on duplex selects for the narrow minor groove of $AT_4$ sequences). All of these ligands are available either commercially or by standard syntheses and may be attached to the porphyrins by amide, ester, ether or similar linkages can be prepared with up to 4 ligand groups.

pyridyl)porphyrin, the space in the groove was mapped out to determine what structures could be devised that would deliver a hydrogen bond accepting group to an appropriate location (distance and angle of approach) proximal to the guanine N(2)H above or below the intercalation site occupied by the porphyrin. This result can be used to design new meso substituents for novel porphyrins. The two positions adjacent to the bond to the porphyrin must be either CH or N to allow the compound to achieve planarity for intercalation. One may use a molecular "scaffold" to attach a hydrogen bond acceptor, a. From this structure a variety of compounds based on substituted quinolines and pyridines can be envisioned as illustrated in Scheme II.

SCHEME II

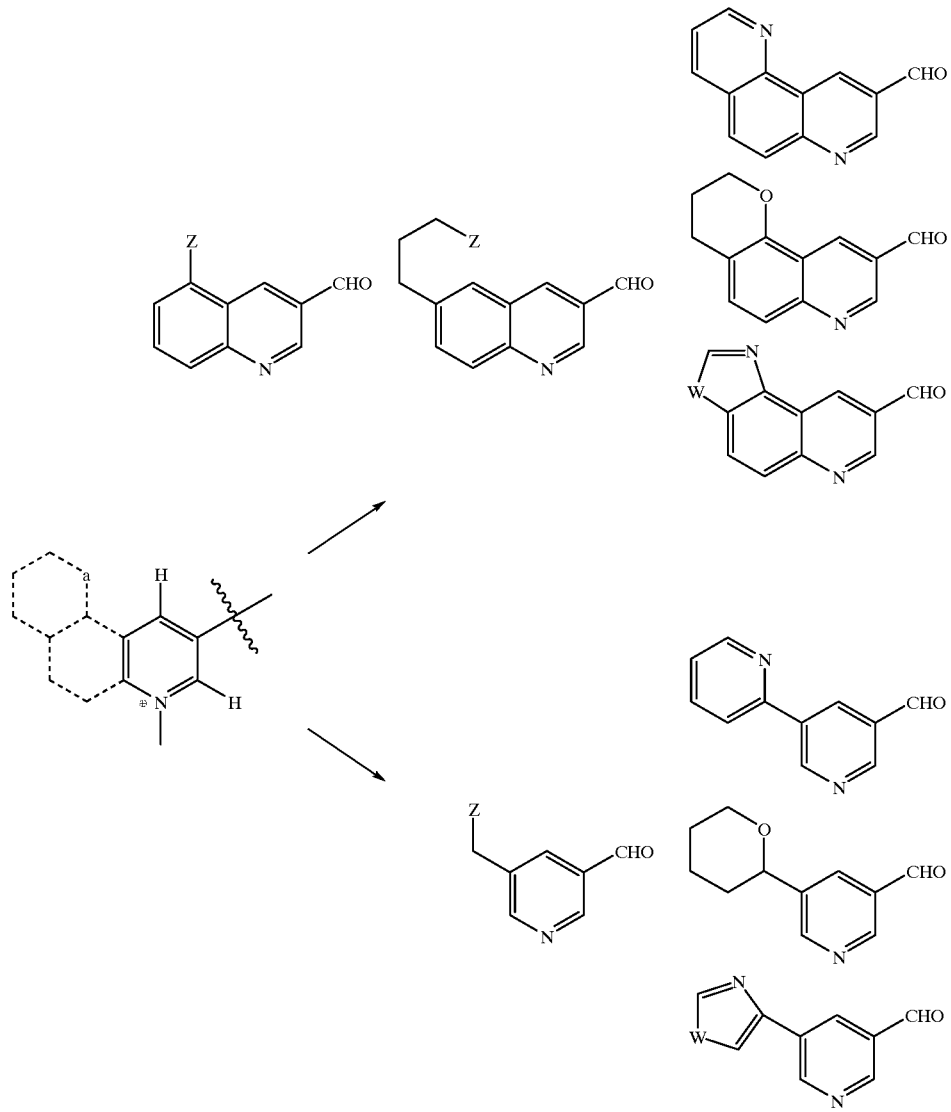

(iii) Design of Meso Substituents Tailored to the Grooves of G-quadruplex

Using a model of the complex between ATTTTTAGGGT-TAGGGTTAGGG (SEQ ID NO:2) and tetra(N-methyl4- where a is a hydrogen bond acceptor, Z is a substituent such as OMe, $NMe_2$, $NH_2$, OH or $CF_3$ and W may be heterocyclic such as NH, O or S.

(iv) Other Uses of G-quadruplex Specific Porphyrins

There are two additional ways in which G-quadruplex selective porphyrins may be used in the development of therapeutics.

(a) G-quadruplex cleavage A compound with the porphyrin linked to a DNA cleavage agent such as iron-EDTA is expected to selectively destroy G-quadruplex thus rendering telomerase activity futile.

(b) Alkylation The porphyrin may be attached to a group which covalently links to the quadruplex thus rendering the quadruplex more stable and either interfering with telomerase function or blocking the production of telomeric duplex by DNA polymerase.

4.6 Selection of Metal Ions

A range of metal complexes (transition metals and lanthanides) of the simple porphyrins (tetra N-methyl-3-pyridyl, N-methyl-4-pyridyl and N-methyl-3-quinolyl) can be prepared to identify those metals that confer the best combination of low photosentization, strong telomerase inhibition and low cytotoxicity on the porphyrin. The preferred metal ions may be used in the more elaborate porphyrin conjugates.

4.7 Materials and Methods 4.7.1 Molecular Modeling

Models were built using the Sybyl package (Tripos Inc., St. Louis, Mo.). Coordinates for the DNA quadruplex (Wang and Patel, 1993) and TMPyP4 (Lipscomb et al., 1996) were obtained from the Brookhaven Protein Data Bank. Hydrogen bonding constraints were added to the G-tetrads and torsional constraints set to maintain the planarity of the porphyrins. Porphyrins were inserted above and below the G-tetrads and the complex allowed to minimize using Kollman charges, Tripos force field and conjugate gradient. After 100 iterations the porphyrins were replaced and the minimization repeated for 500 iterations to a terminal gradient of 0.05 kcal/mol.

4.7.2 Chemicals and Cell Lines

All porphyrins were obtained from Midcentury, Posen, Ill. The experimental work with porphyrins was performed under minimum exposure to light. All human tumor cell lines and normal human breast cells Hs578Bst were purchased from the American Type Culture Collection. Normal human lung fibroblasts NHLF were obtained from Clonetics Corporation. The cell lines were grown according to the suppliers' instructions.

4.7.3 Telomerase Inhibition Assay

Telomerase activity in human tumor cell lines was measured using a non-PCR™ based telomerase assay with 5'-biotinylated d(TTAGGG)$_3$. Extracts were obtained from $1\times10^6$ cells: the cells were washed once in PBS (400 μl) and pelleted at 10,000 g for 1 min at 4° C., resuspended in 1.5 ml tubes containing 400 μl of ice-cold washing buffer (10 mM HEPES-KOH pH 7.5, 1.5 mM MgCl$_2$, 10 mM KCl, and 1 M DTT), then pelleted again at 10,000 g for 1 min at 4° C. Washed cells were resuspended in 100–400 μl of ice-cold lysis buffer (10 mM Tris-HCl pH 7.5, 1 mM MgCl$_2$, 1 mM EGTA, 0.1 mM PMSF, 5 mM β-mercaptoethanol, 1 mM DTT, 0.5% CHAPS, 10% glycerol, and 40 UI/ml RNase guard). The suspension was incubated on ice for 30 min and the lysate then transferred to polyallomer tubes (Beckman) and spun at 100,000 g for 1 h at 4° C. in a tabletop ultracentrifuge. The supernatants were stored at −80° C. in 10% glycerol. Protein concentration was determined by the Bradford assay (BioRad). All tumor cell extracts were normalized to the same protein concentration (1 mg/ml).

Telomerase reaction mixtures were protected from light during the reactions involving porphyrins. In brief, reaction mixtures (20 μl) containing 4 μl of cell lysate, 50 mM Tris acetate pH 8.5, 50 mM potassium acetate, 1 mM MgCl$_2$, 5 mM β-mercaptoethanol, 1 mM spermidine, 1 μM telomere primer, 1.5 μM [α-$^{32}$P]-dGTP (800 Ci/mmol), 2 mM dATP, and 2 mM dTTP were incubated at 37° C. for 1 h. Reactions were terminated by adding 20 μl of streptavidin-coated Dynabead suspension containing 10 mM Tris-HCl pH 7.5 and 2 M NaCl. The beads complexed selectively with the 5'-biotinylated DNA. The complex was separated from the suspension using a magnet (Dynal MPC) and washed several times with washing buffer (1M NaCl) to eliminate [α-$^{32}$P]-dGTP background. Telomerase reaction products were separated from the magnetic beads by protein denaturation with 5.0 M guanidine-HCl at 90° C. for 20 min. After ethanol precipitation, the reaction products were analyzed by 8% polyacrylamide gel electrophoresis. Telomerase activity in HeLa cells was used for reference and defined as 100% activity.

4.7.4 Cytotoxicity Assay (MTT)

Exponentially growing cells ($1-2\times10^3$ cells) in 0.1 ml medium were seeded on day 0 in a 96-well microtiter plate. On day 1, 0.1 ml aliquots of medium containing graded concentrations of the investigational compound were added to the cell plates. After incubation at 37° C. in a humidified incubator for 4–7 days, the plates were centrifuged briefly and 100 μl of the growth medium was removed. Cell cultures were incubated with 50 μl of 3-(4,5-dimethylthiazol-2-yl)-2,5-diphenyltetrazolium bromide [MTT, 1 mg/ml in Dulbecco's phosphate buffered saline (PBS)] for 4 hr at 37° C. The resulting purple formazan precipitate was solubilized with 200 μl of 0.04 M HCl in isopropyl alcohol. Absorbance was measured in a BioRad Model 3550 Microplate Reader at a test wavelength of 570 nm and a reference wavelength of 630 nm. The absorbance data were transferred to a PC 486 computer and IC$_{50}$ values determined by fitting the data (n=2) to a four-parameter logistic equation using the program EZ-ED50 as described (Mossman, 1983; Chen et al., 1993).

4.7.5 Telomere Length Analysis

DNA was extracted from a minimum of $5\times10^6$ cells by SDS, proteinase K treatment, then purified and quantitated as previously described (Strahl and Blackburn, 1991). Approximately 1 μg of total DNA was digested with Mse I; the digested DNA was size fractionated by agarose gel electrophoresis and Southern blotted. The blots were hybridized with a $^{32}$P-labeled 0.5 kb PCR™ DNA fragments composed of the telomere repeat d(TTAGGG), which served as a probe for the telomeres. The hybridized probe was detected by autoradiography and each lane on the film was analyzed by phosphoimage analysis (Molecular Dynamics).

4.7.6 Cell Cycle Analysis

The effects of TMPyP4 on the cell cycle were assessed by flow cytometry by measuring the percentage of cells in G1/G0, S, and G2/M phases, with and without treatment with the porphyrin. Cells were stained with 50 μg/ml propidium iodide in a hypotonic sodium citrate solution with 0.3% NP-40 and 1.0 mg/ml RNase-A at $1.0\times10^6$ cells/ml, vortexed and stained for 30 min at room temperature in the dark. Prior to flow cytometric measurements, samples were filtered through a 37 μm nylon mesh into 12×75 mm tubes and stored at 4° C. until analysis within 24 h. All samples were analyzed with an EPICS ELITE flow cytometer (Coulter Cytometry, Miami, Fla.) using a 15 m Watt argon ion laser operated at 6 Amps of power at 488 nm for fluorochrome excitation. Photomultiplier tube voltage was adjusted for each control sample to position the G0G1 to channel 240 on a 1024 channel presentation. The propidium iodide emission was collected through a 675 nm long pass filter. Histograms were analyzed for cell cycle compartments using MultiCycle-PLUS Version 3.0 (Phoenix Flow Systems, San Diego, Calif.). Histograms all had 50K events collected to maximize the statistical validity of the compartmental analysis.

4.7.7 Nuclear Localization of TMPyP4

MCF7 cells were seeded at $5 \times 10^5$ cells per flask and cultured in the presence of 0, 50, or 100 µM TMPyP4 for 7 days with one exchange of medium. The cells were harvested with trypsin-EDTA, washed with PBS and counted using a Coulter counter. The cells were then pelleted by centrifugation at 700 g and lysed in a hypotonic solution (0.1×PBS); the resulting lysate was sedimented at 700 g for 10 min. The supernatant was removed and the pellet was dissolved in 0.5 ml of 2% SDS. Absorbance of the supernatants and pellet was measured at 423 nm. TMPyP4 diluted in 2% SDS containing 1 mg/ml salmon sperm DNA was used for the standard curve.

4.7.8 Metaphase Spreads

MCF7 cells (at $5 \times 10^5$ cells per flask) were grown for 3 days in the presence of QP3.In$^{III}$ (the most fluorescent porphyrin). The cells were trypsinized, harvested by centrifugation and incubated in Colcimide (Gibco) at 100 ng/ml for 1 h. The cells were pelleted, the medium was replaced with 75 mM KCl (hypotonic solution). After incubation for 20 min, the cells were spun at 700 g for 2 min, all but 1 ml of the KCl solution was removed, and the cells were gently resuspended; 10 ml of freshly prepared methanol-glacial acetic acid (3:1) was added to the cells for fixation. The fluorescence microphotographs were taken with the filters for the excitation wavelength at 563–598 nm (maximum 582 nm) and emission at 584–620 nm (maximum 600 nm).

4.7.9 Sea Urchin Embryos

*Lytechinus pictus* sea urchins were purchased from Marinus Inc. (Long Beach, Calif.) and maintained at 15° C. in refrigerated aquaria containing Instant Ocean synthetic sea water, following a described procedure [Vafa, 1996 #300]. For polyspermic fertilization, 0.01 vol freshly prepared stock sperm suspension (25 ml ASW containing 2 ml undiluted semen) was added to the eggs suspended for 10 min at 1% concentration in ASW adjusted to pH 9.0 with $NH_4OH$ and stirred at 60 rpm with motor-driven Teflon paddles. Ten min after insemination, the fertilized eggs were allowed to settle, and the supernatant ASW containing sperm was aspirated and replaced with fresh ASW. The embryos were cultured at 18° C. Twenty min after fertilization TMPyP4 or TMPyP4.Pt$^{II}$ (100 µM final concentration) was added from a concentrated stock in DMSO to 1% embryo suspensions. Equivalent amounts of DMSO (final 0.1%) were added to control egg suspensions. At measured times after insemination, the embryos were pelleted by centrifugation and resuspended in Carnoy's fixative (ethanol:acetic acid, 3:1) for at least 1 hr. After fixation the embryos were pelleted and resuspended successively in: (1) ethanol:acetic acid, 1:1 for 5–15 min: (2) 45% acetic acid for 5–15 min; (3) room temperature 1 N HCl for 1–2 min: (4) 60° C. 1 N HCl for 7–8 min; (5) room temperature 1 N HCl for 1–2 min; (6) Schiffs reagent for 90–120 min; and (7) 45% acetic acid before affixing the embryos to microscope slides. Embryo samples were placed on microscope slides, covered with coverslips, and frozen on a bed of dry ice. After at least 30 min, the coverslips were popped off using a razor blade and the slides were immediately plunged into Coplin jars containing 95% ethanol for 5–10 min. The slides were then transferred to Coplin jars containing 100% ethanol for 3–5 min. After removing the slides and allowing them to air dry, the embryos were mounted with one drop Permount (Fisher) under a coverglass.

4.7.10 Photocleavage Assay

The 39-base single-strand DNA sequence 5'-CATGGTGGTTTGGGTTAGGGTTAGGGTTAGGG-TTACCAC-3' (SEQ ID NO:5) was synthesized on a Perseptive Biosystems Expedite nucleic acid synthesizer and purified by polyacrylamide gel electrophoresis. The DNA was labeled with 32p at the 5'-end and stored in buffer (10 mM Tris-HCl, 1 mM EDTA, pH 8.0) at 3000 cpm/µl. For each photocleavage reaction, 10 µl of DNA (~5 ng) was mixed with 10 µl of 200 mM KCl, boiled for 10 min, and cooled to room temperature. For the control studies, 10 µl of distilled water was added instead of the KCl solution. The mixtures were transferred to a 96 well plate, 2 µl of 1 µM aqueous TMPyP4 solution added, and the samples exposed to a 24 W fluorescent day-light under a glass filter for various periods of time. The reactions were stopped with 100 µl of calf thymus DNA (0.1 µg/µl), and after phenol-chloroform extraction, the samples were subjected to strand breakage treatment and ethanol precipitation (Han and Hurley, 1996). The DNA samples were loaded onto a 12% polyacrylamide gel for electrophoresis and visualized using a phosphorimager (Molecular Dynamics, model 445 S1).

4.7.11 DNA Synthesis Arrest Assay

This assay was a modification of that described by Weitzmann et al. (Wang and Patel, 1993). Briefly, primers (24 nM) labeled with [γ-$^{32}$P] ATP were mixed with template DNA PQ74 (12 nM) in a Tris-HCl buffer (10 mM Tris, pH 8.0) containing 10 mM $MgCl_2$ and heated at 90° C. for 4 min. After cooling at room temperature for 15 min, spermidine (to give 100 µM) and TMPyP4 (to give the concentrations indicated in the figure) were added. The primer extension reactions were initiated by adding dNTP (final concentration 100 µM) and Taq DNA polymerase (2.5 U/reaction, Boehringer Mannheim). The reactions were incubated at 55 C. (or otherwise as indicated) for 15 min, then stopped by adding an equal volume of stop buffer (95% formamide, 10 mM EDTA, 10 mM NaOH, 0.1% xylene cyanol, 0.1% bromophenol blue). The products were separated on a 12% polyacrylamide sequencing gel. The gels were then dried and visualized on a phosphorimager (Molecular Dynamics model 445 S1).

Sequence of the template, PQ74:
5'-TCCAACTATGTATAC(TTGGGG)$_4$TTAGCGGCACGCAATTGCTATAGTGAGTCGT-ATTA-3' (SEQ ID NO:6)

Sequence of the primer:
5'-TAATACGACTCACTATAG-3' (SEQ ID NO:7)

4.7.12 Rapid Telomerase Assay

For an initial evaluation of novel G-quadruplex interactive porphyrins as telomerase inhibitors, a rapid telomerase assay was used. The assay employs a 5'-biotinylated (TTAGGG)$_3$ primer, SEQ ID NO:1. The 20 µl reaction mixture contains 1 µM primer, 2 mM dATP and dTTP, 0.2 µM α$^{32}$P-dGTP, 5 µl S-100 extract as a telomerase source, and an appropriate concentration of test compound. After incubation at 37° C. for 1 hour, the telomerase reaction is terminated by the addition of Streptavidin-coated Dynabeads which selectively immobilize the 5'-biotinylated DNA sequences. The beads are separated from the suspension using a magnet (Dynal MPC) and transferred to a nylon membrane on a 96-well Minifold apparatus where they are washed intensively to eliminate the $^{32}$P-dGTP background. The Dynabead-product complex on the nylon membrane is air dried, covered with a plastic wrap and exposed to X-ray film for 3 hours. The autoradiogram is analyzed using a Phosphor-Imaging Analyzer. Alternatively, telomerase reaction products may be recovered from the Dynabeads using protein denaturant and analyzed by denaturing polyacrylamide gel electrophoresis for a comprehensive telomere length analysis. Rapid assay data for several porphyrins are shown in FIG. 3 and FIG. 4.

The assay was generally performed using 5'-end-biotinylated d(TTAGGG)$_3$ (SEQ ID NO:1) as a telomere (Sun et al., 1997). Telomerase reaction mixtures were protected from light exposure during the reactions by using brown-colored tubes to avoid degradation of reaction components by TMPyP4. In brief, reaction mixtures (20 µl) containing 4 µl of cell lysate, 50 mM Tris-OAc (pH 8.5), 50 mM K-OAc, 1 mM MgCl$_2$, 5 mM β-mercaptoethanol, 1 mM spermidine, 1 µM telomere primer, 1.5 µM [α-$^{32}$P]-dGTP (800 Ci/mmol), 2 mM dATP, and 2 mM dTTP were incubated at 37° C. for 1 h. Reactions were terminated by adding 20 µl of Streptavidin-coated Dynabeads suspension containing 10 mM Tris-HCl (pH 7.5) and 2 M NaCl. Streptavidin-coated Dynabeads bind selectively to the desired target (5'-biotinylated DNA), forming a magnetic bead-target complex. This complex was separated from the suspension using a magnet (Dynal MPC) and washed several times with washing buffer (1M NaCl) to eliminate [α-$^{32}$P]-dGTP background. Telomerase reaction products were separated from the magnetic beads by protein denaturation with 5.0 M guanidine-HCl at 90° C. for 20 min. After ethanol precipitation, the reaction products were analyzed by 8% polyacrylamide gel electrophoresis.

4.7.13 Telomerase Assay

A standard telomerase assay uses (TTAGGG)$_3$ (SEQ ID NO:1) as primer and dTTP, and α-$^{32}$P-dGTP as substrates. The products are separated by polyacrylamide gel electrophoresis and detected by phosphoimaging analyzer.

Telomerase inhibition was assessed by measuring activity against telomerase activity in HeLa cell extract using a primer extension assay. A 5'-biotinylated primer consisting of three telomeric repeats was employed and the incorporation of $^{32}$P-labeled GTP assayed. To facilitate screening of large numbers of compounds, the porphyrin concentration was fixed at 25 µM and TMPyP4 and QP3, set. Data are presented in the tables included as controls in each data as the percentage inhibition of telomerase relative to the telomerase activity measured in the porphyrin-free control (0%). Select compounds were later run at different concentrations to determine IC$_{50}$ values.

FIG. 5A shows the concentration-dependent effect of TMPyP4 on the ladder produced by telomerase extension of an 18-base primer. By quantitation of the bands in each lane using a phosphorimager the relative telomerase activity was calculated as a percentage of activity measured in the control and the IC$_{50}$ determined from the graph, FIG. 6B. TMPyP4 showed an IC$_{50}$ of 6.5±1.4 µM. The pattern of ladders formed by telomerase extension of the 18-base primer in the presence of TMPyP4 was quite different from that seen in the control reaction. In the presence of low concentrations of TMPyP4, the amounts of the first and second extension products were little affected but a significant reduction in the formation of products corresponding to more than four repeats was seen (see FIG. 5A). Since a quadruplex structure cannot be formed until after at least two rounds of extension, this result supports the contention that TMPyP4 interacts mainly with quadruplex structures formed during the telomerase reaction. Previously (Salazar et al., 1996) the inventors observed that an anthraquinone inhibited telomerase by targeting G-quadruplex structures generated during the telomerase reaction and produced a change in the pattern of ladder formation which is very similar to that observed in the presence of TMPyP4.

4.7.14 Chemicals and Reagents

Porphyrins not described in the synthetic section were obtained from Midcentury Inc., Posen, Ill. Other chemicals and reagents were purchased through the Aldrich Chemical Company (Milwaukee, Wis.).

4.7.15 Molecular Modeling

Models were built using the Sybyl package (Tripos Inc., St. Louis, Mo.). Coordinates for the DNA quadruplex (Sun et al., 1997) and TMPyP4 (Wheelhouse et al., 1997) were obtained from the Brookhaven Protein Data Bank (Brookhaven, N.Y.). Hydrogen bonding constraints were added to the G-tetrads and torsional constraints set to maintain the planarity of the porphyrins. Porphyrins were inserted above and below the G-tetrads and the complex allowed to minimize using Kollman charges, Tripos force field and conjugate gradient. After 100 iterations the porphyrins were replaced and the minimization repeated for 500 iterations to a terminal gradient of 0.05 Kcal/mol.

4.7.16 Measurements

NMR spectra were acquired on Bruker AC250 and Varian Gemini 300 spectrometers recording $^1$H at MHz and $^{13}$C at MHz. Melting points are uncorrected.

4.7.17 Synthetic Methods 4.7.17.1 General Method A: from pyrrole and arylaldehydes in propionic acid A mixture of the appropriate arylaldehye (mol) and pyrrole (mol) in propionic acid (vol) was heated under reflux in air, after which the solvents were evaporated and the products purified by column chromatography. For mixed substituents the appropriate mixture of arylaldehydes was used and the products separated by column chromatography following a precolumn to remove non-porphyrin byproducts.

4.7.17.2 General Method B: Preparation of Quaternary Ammonium Salts

The substituted porphyrin (mol) free base was dissolved in chloroform (ml) and appropriate alkyliodide added. The mixture was heated under reflux for h, cooled to room temperature, the products collected by filtration and washed with excess chloroform. Final compounds were converted to the chloride salts by mixing a slurry of the iodide salt in water with a ten-times excess of Dowex 50 ion exchange resin in the chloride form and warming over a water bath with occasional stirring until all the porphyrin had dissolved. Filtration and evaporation of the filtrate yielded the chloride salts.

D1 5,10,15,20-tetra-(N-ethyl-4-pyridyl)porphine chloride

D3 5,10,15,20-tetra-(N-[2-hydroxyethyl]-4-pyridyl) porphine chloride

D2 5,10,15,20-tetra-(N-acetoxymethyl-4-pyridyl)porphine chloride

D4 5,10,15,20-tetra-(N-ethyl-3-pyridyl)porphine chloride

D5 5,10,15,20-tetra-(N-[2-hydroxyethyl]-3-pyridyl) porphine chloride

D6 5,10,15,20-tetra-(N-acetoxymethyl-3-pyridyl)porphine chloride

D7 Copper(II)tetra-N-methyl-tetrazaphthalocyanine

D10(D8) 5,10,15,20-tetra-(6-methyl-N-methyl-2-pyridyl) porphine chloride

D12 5,10-di-(N-methyl-3-quinolyl)-15,20-di-(N-methyl-3-pyridyl)porphine chloride D11 5,10,15-tri-(N-methyl-3-quinolyl)-20-(N-methyl-3-pyridyl)porphine chloride D13 5,10,15,20-tetra-(4-chloro-3-nitrophenyl)porphine chloride D14 5,10-di-(3-nitro-4-hydroxyphenyl)porphine chloride D17 5,10,15,20-tetra-(4-methoxy-3-hydroxyphenyl) porphine chloride D23 5,10,15-tri-(N-methyl-4-pyridyl)-20-(4-carboxyphenyl)porphine chloride D22 5,10,15-tri-(N-methyl-4-pyridyl)-20-(3-carboxyphenyl)porphine chloride D21 5,10-di-(N-methyl-4-pyridyl)-15,20-(3-carboxyphenyl)porphine chloride D19 5,10,15-tri-(N-methyl-4-pyridyl)-20-(3-nitrophenyl) porphine chloride D20 5,10-di-(N-methyl-4-pyridyl)-15,20-di-(3-nitrophenyl) porphine chloride D16 5,10-di-(3-nitrophenyl)porphine D24 5,10,15-tri-(N-methyl-4-pyridyl)-20-(3-carboxamidophenyl)porphine chloride D25 5,10-di-(N-methyl-4-pyridyl)-15,20-di-(3-[2-bromoethylcarboxamido)phenyl)porphine chloride D26 5,10-tri-(N-methyl4-pyridyl)-15,20-di-(3-acetylamino) porphine chloride D27 5,10-di-(N-methyl-4-pyridyl)-15,20-di-(3-carboxamidophenyl)porphine chloride D28 5,10,15,20-tetra-(5-[2-furanyl]-N-methyl-3-pyridyl)-porphine chloride 5,10,15-tri-(5-[3-thiophene]-N-methyl-3-pyridyl)-20-(5-bromo-N-methyl-3-pyridyl)porphine chloride 5,10,15,20-tetra-(5-[3-thiophene]-N-methyl-3-pyridyl)-porphine chloride 5,10,15,20~tetra-(5-[2-thiophene]-N-methyl-3-pyridyl)-porphine chloride 5,10-di-(3-bromomethylcarboxamido)-15,20-di-(N-methyl-4-pyridyl)porphine chloride

5.0 EXAMPLES

5.1 Example 1

Porphyrin Preparation

The standard porphyrin synthesis is the acid catalyzed condensation of pyrrole with an aryl or heteroaryl aldehyde, Scheme I. This reaction is versatile and with a wide range of pyridyl and quinolyl aldehydes available lends itself to the combinatorial synthesis of novel porphyrins with mixed meso substituents.

The cationic porphyrins are prepared by subsequent reaction with a methyl donor such as methyl iodide or dimethylsulfate. Metal complexes are typically prepared by heating a solution of the porphyrin and a metal chloride at reflux in a suitable solvent. The complexes are purified by a combination of column chromatography, HPLC and crystallization.

Novel porphyrins were prepared as described below; D3, 5,10,15,20-tetra-(N-[2-hydroxyethyl]-4-pyridyl)porphine chloride and D5, 5,10,15,20-tetra-(N-[2-hydroxyethyl]-3-pyridyl)porphine chloride [5-(3-ethylcarbonyloxyphenyl)-10,15,20-tris-(4-pyridyl)]porphine were prepared according to published procedures.

5.1.1 General Method A: From Pyrrole and Arylaldehydes in Propionic Acid

Pyrrole (0.3 M) in propionic acid was mixed a mixture of the appropriate benzaldehyde, pyridine carboxaldehyde and quinoline carboxaldehydes to give a total of 1 equivalent and heated under reflux in air for 1 hr, after which the solvents were evaporated and the products purified by column chromatography.

5.1.2 General Method B: Preparation of 5,10-disubstituted Porphyrins

Dipyrrylmethane (0.54 mmol) and one equivalent of aromatic aldehyde were dissolved in dry dichloromethane (60 mL), one drop of trifluoroacetic acid added and the mixture stirred at room temperature. After 15 hr, chloranil (2.20 mmol) was added and the solution heated under reflux for 1 hr. Evaporation of the solvent gave a purple solid which was purified by flash column chromatography.

5.1.3 General Method C: Preparation of Porphyrin Dimers

A solution of [5-(3-ethylcarbonyloxyphenyl)-10,15,20-tris-(4-pyridyl)]-porphyrin in DMF (0.2 M) was treated with various oligoethylene glycol di-p-tosylates (0.9 equiv.) and a large excess of powdered NaOH (~10-fold), and the resulting slurries were stirred for 5 hr. The reaction mixtures were filtered and the filtrates were concentrated to a purple paste and the residue purified by silica gel chromatography eluting with ethanol (7%) in dichloromethane. This yielded purple solids that were further purified by recrystallization from boiling methanol.

Purified porphyrin dimers were dissolved in DMF (~0.2 M) and treated with a large excess of methyliodide. The resulting solutions were stirred for 20 hr and then evaporated. The resulting solid was dissolved in water and adsorbed onto Biorex-70 (protonated form) ion exchange resin. The resin was washed several times with water (3×40 ml) and 1:1 water/methanol (3×40 ml), then treated with 6 M HCl (5×50 ml) to remove the hexacationic porphyrin dimer. The combined acid washes were concentrated to a green solid, dissolved in water, and lyophilized.

5.1.4 General Method D: Preparation of Quaternary Ammonium Salts

The pyridyl- or quinolyl-substituted porphyrin free-base (0.1 mmol) was dissolved in chloroform (1 mL) and diluted with 10 mL of nitromethane. The appropriate alkyliodide (5 mmol) was added and the mixture was heated under reflux for 6 hr under an argon atmosphere and then evaporated to dryness. The residue was taken up in 20 mL of water (or 3 mL of acetone then diluted with water) and treated with 2 g of Dowex 1 X2-200 anion exchange resin in the chloride form, stirring slowly for 1 hr. The resin was removed by filtration and the filtrate lyophilized to give the solid chloride salt. The salt could be further purified by chromatography on lipophilic sephadex using methanol as eluent.

5.1.5 Free-bases meso-Tetra(5-bromo-pyrid-3-yl)porphine

By general method A from pyrrole and 5-bromo-3-fornylpyridine (1:1) in propionic acid and chromatography on silica with chloroform: acetone 6:1 according to general method A yielded meso-tetra(5-bromo-pyrid-3yl)porphine, 18%, $^1$H NMR (CDCl$_3$) δ 9.34 (br s, 4H), 9.14 (d, J=2.2 Hz, 4H), 8.86 (br s, 8H), 8.65 (br s, 4H), −2.94 (s, 2H); MS m/z: 935, 933, 853, 766; HRMS (M+H) calcd 931.8680, obsd 931.8689, $C_{40}H_{23}Br_4N_8$.

D10 free base 5,10,15,20-tetra-(6-methyl-2-pyridyl) porphine

Condensation of 6-methylpyridinecarboxaldehyde and pyrrole (1:1) according to the general method and chromatography twice on silica using chloroform:methanol (50:1 then 100:5) as the eluent gave a brown powder, further purified by recrystallisation form from dichloromethane: hexane (1:12), 12%. $^1$H NMR (CDCl$_3$) δ 8.82 (s, 8H), 7.99–7.90 (m, 8H), 7.53 (d, J=7.0 Hz, 4H), 2.87 (s, 12H), −2.87 (s, 2H); MS (CI) 675 (M+H).

D12 free-base 5,10-di-(3-quinolyl)-15,20-di-(3-pyridyl) porphine chloride D11 5,10,15-tri-(3-quinolyl)-20-(3-pyridyl)porphine chloride Condensation of pyrrole, 3-pyridine carboxaldehyde, 3-quinoline carboxaldehyde (2:1:1) in propionic acid, by general method A and chromatography (twice) using chloroform:methanol 8:1, then chloroform: acetone gave D11 free-base 2%, $^1$H NMR (CDCl$_3$) δ 9.82 (d, J=1.9 Hz, 3H), 9.45 (br s, 1H), 9.01 (br s, 4H), 8.93–8.86 (m, 8H), 8.56 (d, J=7.8 Hz, 1H), 8.49 (d, J=8.5 Hz, 3H), 8.13 (d, J=7.8 Hz, 3H), 8.02–7.94 (m, 3H), 7.81–7.61 (m, 4H); MS (CI) 769 (M+H); and D12 free-base 5%, $^1$H NMR (CDCl$_3$) δ 9.83 (d, J=1.7 Hz, 2H), 9.48 (s, 2H), 9.05 (dd, J=1.5, 4.8 Hz, 8H), 9.00 (br s, 2H), 8.95–8.88 (m, 12H), 8.57 (d, J=7.6 Hz, 2H), 8.49 (d, J=8.4 Hz, 2H), 8.12 (d, J=7.5 Hz, 2H), 7.98 (dt, J=1.3, 7.0 Hz, 2H), 7.82–7.75 (m, 2H), –2.74 (s, 2H). MS (CI) 719 (M+H).

5,15-(4-pyridyl)-10,20-(4-nitrophenyl)porphine

Condensation of pyrrole, 4-pyridine carboxaldehyde and 3-hydroxy-4-nitrobenzaldxehyde (2:1:1) and chromatography on silica using chloroform:acetone (6:1) as the eluent gave 6%.

D9 free-base 5-(4-pyridyl)-10,15,20-tri(4-methylphenyl) porphine and 5,15-di(4-pyridyl)-10,20-di(4-methylphenyl) porphine Condensation of pyrrole, 4-pyridinecarboxaldehyde, 4-tolualdehyde (1:2:1), by general method A. Chromatography on silica dichloromethane:methanol (100:3) gave D9 free-base 4%, $^1$H NMR (CDCl$_3$) δ 9.01 (d, J=4.9 Hz, 2H), 8.92 (d, J=4.8 Hz, 2H), 8.89 (s, 4H), 8.78 (d, J=4.9 Hz, 2H), 8.16 (d, J=5.7 Hz, 2H), 8.09 (d, J=7.7 Hz, 6H), 7.53 (d, J=7.7 Hz, 6H), –2.77 (s, 2H); MS (CI) 657 (M+H); and 5,15-(4-pyridyl)-10,20-(4-methylphenyl)porphine recrystallised from methanol:chloroform (40:10) as a purple solid, 1%.

D20 free-base 5,10-di-(4-pyridyl)-15,20-di-(3-nitrophenyl)porphine

D19 free-base 5,10,15-tri-(4-pyridyl)-20-(3-nitrophenyl) porphine

From the condensation of pyrrole, 4-pyridine carboxaldehyde and 3-nitrobenzaldehyde (2:1:1) according to general method A and chromatography twice on silica eluted with chloroform:methanol (100:3).

D20 free-base 6%, $^1$H NMR (DMSO-d$_6$) δ 9.18 (d, J=5.5 Hz, 4H), 9.00–8.85 (m, 6H), 8.90 (br s, 2H), 8.50 (br d, 4H), 8.41 (d, J=7.5 Hz, 4H), 8.36 (s, 2H), 8.02 (m, 2H), 7.60 (s, 2H), –3.01 (s, 2H); MS (CI) 707 (M+H D19 free-base 9%, $^1$H NMR (CDCl$_3$) δ 9.05 (m, 8H), 8.84 (s, 6H), 8.78 (br d, 1H), 8.68 (d, J=7.8 Hz, 1H), 8.48 (d, J=7.9 Hz, 1H), 8.90 (d, J=5.3 Hz, 6H), 7.96 (t, J=7.5 Hz, 1H), –2.90 (s, 2H); MS (CI) m/z: 663 (M+H).

D22 free-base, 5,10,15-tri-(4-pyridyl)-20-(3-carboxyphenyl)porphine

D21 free-base 5,10-di-(4-pyridyl)-15,20-(3-carboxyphenyl)porphine

From the condensation of pyrrole, 4-pyridinecarboxaldehyde and 3-carboxybenzaldehyde according to general method A followed by chromatography (twice) on silica eluted with chloroform:methanol:acetic acid (110:10:1).

D22 free-base 7%, $^1$H NMR (DMSO-d$_6$) δ 13.01 (br s, 1H), 9.00 (be s, 6H), 8.86 (br s, 8H), 8.71 (br s, 1H), 8.46–8.41 (m, 2H), 8.23 (br s, 6H), 7.95 (br s, 1H), –2.98 (br s, 2H). MS (CI) 662 (M+H);

D21 free-base 4%, $^1$H NMR (DMSO-d$_6$) δ 12.80 (br s, 2H), 9.03 (d, J=5.4 Hz, 4H), 8.89–8.82 (m, 8H), 8.70 (be s, 2H), 8.14–8.41 (m, 4H), 8.26 (br d, 4H), 8.00–7.94 (m, 2H), –3.00 (s, 2H); MS (CI) 705 (M+H).

D23 free-base 5,10,15-tri-(4-pyridyl)-20-(4-carboxyphenyl)porphine

Condensation of pyrrole, 4-pyridine carboxaldehyde, and 4-carboxybenzaldehyde (4:3:1) in propionic acid according general method A. Chromatography twice on silica with chloroform:methanol (10:1 then 95:6) gave.

D23 freebase 4%, $^1$H NMR (DMSO-d$_6$) δ 9.06 (d, J=5.4 Hz, 6H), 8.84 (S, 6H), 8.80 (s, 2H), 8.36 (d, J=8.2 Hz, 2H), 8.28 (d, J=4.8 Hz, 6H), 8.20 (d, J=8.1 Hz, 2H), –2.89 (br s, 2H); MS (CI) 707 (M+H).

D24 free-base 5,10,15-tri-(4-pyridyl)-20-(3-carboxamidophenyl)porphine 5,10,15-tri-(4-pyridyl)-20-(3-carboxyphenyl)porphine (65 mg, 98 μmol) in 8 mL of dry THF was added carbonyldiimidazole (14 mg, 86 μmol) and the mixture heated under reflux for 1 hr under a nitrogen atmosphere. The reaction mixture was cooled to room temperature and concentrated aqueous ammonium hydroxide added (1 mL) and the mixture stored at room temperature overnight. The porphyrin was extracted into chloroform (60 mL), washed with saturated aqueous NaHCO$_3$ and dried over sodium sulphate. Chromatography on silica eluted with chloroform: methanol:acetic acid (100:10:1) gave a solid 58 mg, 89%, $^1$H NMR (CDCl$_3$) δ 9.03 (d, J=6.8 Hz, 6H), 8.9 (m, 8H), 8.70 (br s, 1H), 8.46 (m, 2H), 8.28 (d, J=6.8 Hz, 6H), 7.94 (br s, 1H), 7.55 (s, 2H), –2.81 (s, 2H); HRMS (M+H) calcd 661.2464, obsd 661.6430, C$_{42}$H$_{29}$N$_8$O.

D26 other intermediate free-base 5,10,15-tri-(4-pyridyl)-20-(3-aminophenyl)porphine 5,10,15-tri-(4-pyridyl)-20-(3-nitrophenyl)porphine (0.18 g, 0.272 mmol) was reduced with SnCl$_2$ (0.98 g, 4.33 mmol) in 6M HCl (18 mL) according to the procedure of reference 33 to give 0.124 g (72%), $^1$H NMR (CDCl$_3$) δ 9.04, (d, J=5.9 Hz, 6H), 8.89 (d, J=4.9 Hz, 2H), 8.85 (s, 4H), 8.80 (br s, 2H), 8.16 (br s, 6H), 7.99 (br s, 3H), 7.34 (s, 1H), –3.03 (s, 2H); MS (CI) 633 (M+H).

D26 free-base 5,10,15-tri-(4-pyridyl)-20-di-(3-acetylamino)porphine

A mixture of tri3-Py-mono3-NH2, (30 mg, 47 μmol) acetic anhydride (2 ml) and triethylamine (1 mL, 7.2 mmol) in 10 mL of dry chloroform was heated overnight. After evaporation of solvents and chromatography on silica eluting with chloroform:methanol:acetic acid (100:10:1) a solid was obtained, 21 mg (65%), $^1$H NMR (CDCl$_3$) δ 9.02 (d, J=5.8 Hz, 6H), 8.91 (d, J=4.9 Hz, 2H), 8.82 (s, 4H), 8.79 (br d, 2H), 8.30 (br s, 1H) 8.17 (d, J=6.2 Hz, 6H), 7.98 (br s, 1H), 7.69–7.65 (m, 2H), 6.82 (s, 1H), 2.23 (s, 3H), –3.03 (s, 2H); MS (CI) 675 (M+H).

D27 free-base 5,10-di-(4-pyridyl)-15,20-di-(3-carboxamidophenyl)porphine

Prepared from D21 free-base by a similar method to the preparation of D24 free-base, 55% yield, $^1$H NMR (DMSO-d$_6$) δ 9.16 (d, J=5.5 Hz, 4H), 8.96–8.86 (m, 6H), 8.71 (br s, 2H), 8.49 (br d, 4H), 8.38 (d, J=7.7 Hz, 4H), 8.26 (br s, 2H), 7.93 (t, J=7.6 Hz, 2H), 7.58 (br s, 2H), –2.98 (s, 2H); MS (CI) 703 (M+H), 686.

D28 free-base meso-Tetra[5-(2-furyl)pyrid-3-yl]porphine

Meso-tetra(5-bromo-pyrid-3-yl)porphine, 61 mg, 65 μmol), 2-furanboronic acid (60 mg, 520 μmol) and Pd(PPh$_3$)$_4$ (2 mg, 1.74 μmol) were dissolved in a mixture of toluene (7.5 mL) and methanol (1.8 mL) under argon. Aqueous sodium carbonate (1.5 mL, 2M) was added via a syringe and the reaction stirred at 70° C. for 20 hr. Further boronic acid (25 mg) and Pd(PPh$_3$)$_4$ (1 mg) were added and the reaction continued for another 15 hr. The mixture was poured into 40 mL water and extracted with chloroform (3 times 60 mL). The combined extracts were dried over sodium sulphate, filtered and evaporated. The product was purified by flash chromatography eluting with chloroform-acetone (5:1) to give a solid, 25 mg (44%). $^1$H NMR (CDCl$_3$) δ 9.35 (d, J=2 Hz, 4H), 9.29 (br s, 4H), 8.91 (br s, 8H), 8.76 (br s, 4H), 7.56 (s, 4H) 6.96 (d, J=3.2 Hz, 4H), 6.56 (m, 4H), –2.82 (s, 2H).

meso-Tetra[5-(3-thiophen)pyrid-3-yl]porphine and 5-(5-bromopyrid-3-yl)-10,15,20-tri[5-(thiophen-3-yl)pyrid-3-yl] porphyrin From 5,10,15,20-Tetra-[3-(5-bromopyridyl)]porphyrin (20 mg, 21 μmol), 3-thiophene boronic acid (21 mg, 164

μmol) and Pd(PPh$_3$)$_4$ (1 mg) according to the procedure used for the preparation of D28. Flash chromatography eluting with chloroform:acetone 5:1 gave meso-tetra[5-(thiophen-3-yl)pyrid-3-yl]porphine, 4 mg, (13%), $^1$H NMR (CDCl$_3$) δ 9.36 (br, 4H), 9.31 (s,4H), 8.94 (br, 8H), 8.72 (br, 4H), 7.76 (br, 4H), 7.09 (d, J=4.5 Hz, 4H), 7.51 (br d, 4H), −2.80 (s, 2H); HRMS (M+H) calcd 947.1868, obsd 947.1842, C$_{56}$H$_{35}$N$_8$S$_4$; and 5-(5-bromopyrid-3-yl)-10,15,20-tri[5-(thiophen-3-yl)pyrid-3-yl]porphyrin, 10.5 mg (35%), $^1$H NMR (CDCl$_3$) δ 9.45 (br, 3H), 9.32 (br, 1H), 9.27 (br, 3H), 9.40 (br, 1H), 8.92 (br, 4H), 8.87 (br, 3H), 8.68 (s, 4H), 8.65 (br, 1H), 7.78 (br, 3H), 7.71 (br, 3H), 7.65 (d, J=3.6 Hz, 3H), −2.74(s, 1H), −2.26 (s, 1H); MS (CI) 943, 899, HRMS (M+H) calcd 943.1095, obsd 943.1089, C$_{52}$H$_{32}$BrN$_8$S$_3$.

G2 Free base Diethylene glycol di-[5-(3-hydroxyphenyl)-10,15,20-tri-(4-pyridyl)]-porphine By general method C, 43%; $^1$H NMR (CDCl$_3$) δ 9.00 (m, 8H), 8.92 (d, J=4.9 Hz, 4H), 8.83 (s, 12H), 8.76 (d, J=4.7 Hz, 4H), 8.16 (m, 12H), 7.78 (m, 4H), 7.55 (t, J=7.3 Hz, 2H), 7.28 (m, 2H), 4.25 (m, 4H), 3.86 (m, 4H), −2.91 (s, 4H); MS (FAB) (NBA) m/z: 1338 (M+H).

G3 Free base Tetraethylene glycol di-[5-(3-hydroxyphenyl)-10,15,20-tri-(4-pyridyl)]-porphine By general method C, 44%; $^1$H NMR (CDCl$_3$) δ 9.00 (m, 8H), 8.92 (d, J=4.9 Hz, 4H), 8.83 (s, 12H), 8.76 (d, J=4.7 Hz, 4H), 8.16 (m, 12H), 7.78 (m, 4H), 7.55 )t, J=7.3 Hz. 2H), 7.28 (m, 2H), 4.24 (m, 4H), 3.87 (m, 4H), 3.68 (m, 8H), −2.92 (s, 4H); MS (FAB) (NBA) m/z: 1425 (M+H).

G4 Free base Pentaethylene glycol di-[5-(3-hydroxyphenyl)-10,15,20-tri-(4-pyridyl)]porphine By general method C, 17%; $^1$H NMR (CDCl$_3$) δ 9.00 (m, 8H), 8.92 (d, J=4.9 Hz, 4H), 8.83 (s, 12H), 8.76 (d, J=4.7 Hz, 4H), 8.16 (m, 12H), 7.78 (m, 4H), 7.55 (t, J=7.3 Hz. 2H), 7.28 (m, 2H), 4.22 (m, 4H), 3.88 (m, 4H), 3.68 (m, 12H), −2.90 (s, 4H); MS (FAB) (NBA) m/z: 1470 (M+2H).

G5 Free base Hexaethylene glycol di-[5-(3-hydroxyphenyl)-10,15,20-tri-(4-pyridyl)]porphine By general method C, 20%; $^1$H NMR (CDCl$_3$) δ 9.00 (m, 8H), 8.92 (d, J=4.9 Hz, 4H), 8.83 (s, 12H), 8.76 (d, J=4.7 Hz, 4H), 8.16 (m, 12H), 7.78 (m, 4H), 7.60 (t, J=7.3 Hz, 2H), 7.31 (m, 2H), 4.26 (m, 4H), 3.87 (m, 4H), 3.50–3.70 (m, 16H), −2.91 (s, 4H); MS (FAB) (NBA) m/z: 1514 (M+2H).

5.1.6 Quaternary Ammonium Salts

D7 Copper(II)tetra-N-methyl-tetrazaphthalocyanine

Copper tetraazaphthalocyanine was reacted with dimethyl suplhate according to reference 24, and the chloride salt prepared by ion exchange on Dowex 1. 86% yield, HRMS (FAB) (M) calcd 639.1543, obsd 639.1543, C$_{32}$H$_{24}$N$_{12}$Cu.

D1 5,10,15,20-tetra-(N-ethyl-4-pyridyl)porphine chloride

By general method D from the free base, 96%. $^1$H NMR (D$_2$O) δ 9.13–8.01 (m, 26H), 4.90–4.87 (m, 8H), 1.81–1.75 (m, 12H).

D2 5,10,15,20-tetra-(N-acetoxymethyl-4-pyridyl) porphine chloride

By general method D from the free base, 91% yield. $^1$H NMR (D$_2$O) δ 9.97 (br s, 4H), 9.76 (br d, 4H), 9.35 (br d, 4H), 9.07 (br s, 8H), 8.75–8.66 (m, 4H), 6.78 (s, 8H), 2.25 (s, 12H); HRMS (FAB) (M) calcd 911.3517, obsd 911.3528, C$_{52}$H$_{47}$N$_8$O$_8$.

D4 5,10,15,20-tetra-(N-ethyl-3-pyridyl)porphine chloride
By general method D from the free base.

D6 5,10,15,20-tetra-(N-acetoxymethyl-3-pyridyl) porphine chloride
By general method D from the free base.

D10 5,10,15,20-tetra-(6-methyl-N-methyl-2-pyridyl) porphine chloride

By general method D from the free base, 89% yield. $^1$H NMR (D$_2$O) δ 9.41–7.52 (m, 20H), 3.81 (s, 12H), 2.73 (s, 12H). HRMS (FAB) (M) calcd 733.3767, obsd 733.3767, C$_{48}$H$_{45}$N$_8$.

D12 5,10-di-(N-methyl-3-quinolyl)-15,20-di-(N-methyl-3-pyridyl)porphine chloride By general method D from the free base. $^1$H NMR (D$_2$O) δ 10.06–7.84 (m, 28H), 4.59 (s, 9H), 4.49 (s, 3H). HRMS (FAB) (M) calcd 777.3454, obsd 777.3420, C$_{52}$H$_{41}$N$_8$.

D11 5,10,15-tri-(N-methyl-3-quinolyl)-20-(N-methyl-3-pyridyl)porphine chloride

By general method D from the free base, 89% yield. $^1$H NMR (D$_2$O) δ 10.03–7.76 (m, 32H), 4.50 (s, 3H), 4.33 (s, 9H).

D9 5-(N-methyl-4-pyridyl)-10,15,20-(4-methylphenyl) porphine chloride

By general method D from the free base.

D19 5,10,15-tri-(N-methyl-4-pyridyl)-20-(3-nitrophenyl) porphine chloride

By general method D from the free base, ion exchange in acetone:water 10:1, 89% yield. $^1$H NMR (DMSO-d$_6$) δ 9.43 (br d, 2H), 8.96–8.86 (m, 10H), 8.09 (br d, 6H), 7.65 (br d, 6H), 4.67 (s, 3H), 2.69 (s, 9H); MS (FAB) 673 (M+H), HRMS (M+H) calcd 707.2883, obsd 707.2872, C$_{44}$H$_{35}$N$_8$O$_2$.

D20 5,10-di-(N-methyl-4-pyridyl)-15,20-di-(3-nitrophenyl)porphine chloride

By general method D from the free base, 79%. $^1$H NMR (CDCl$_3$) δ; HRMS (FAB) (M) calcd 736.2547, obsd 736.2541, C$_{44}$H$_{32}$N$_8$O$_4$.

D21 5,10-di-(N-methyl-4-pyridyl)-15,20-(3-carboxyphenyl)porphine chloride

By general method D from the free base, 79%. $^1$H NMR (D$_2$O) δ 9.05–7.90 (m, 24H), 4.55 (s, 6H). HRMS (M) calcd 734.2642, obsd 734.2653, C$_{46}$H$_{34}$N$_6$O$_4$.

D22 5,10,15-tri-(N-methyl-4-pyridyl)-20-(3-carboxyphenyl)porphine chloride

By general method D from the free base, 76% yield. $^1$H NMR (D$_2$O) δ 9.02–7.96 (m, 26H), 4.56 (s, 9H). HRMS (FAB) (M) calcd 706.2930, obsd 706.2917, C$_{45}$H$_{36}$N$_7$O$_2$.

D23 5,10,15-tri-(N-methyl-4-pyridyl)-20-(4-carboxyphenyl)porphine chloride

By general method D from the free base. $^1$H NMR (D$_2$O) δ 9.49–7.60 (m, 26H), 4.60 (s, 6H); HRMS (M+) calcd 706.2930, obsd 706.2915, C$_{45}$H$_{36}$N$_7$O$_2$.

D24 5,10,15-tri-(N-methyl-4-pyridyl)-20-(3-carboxamidophenyl)porphine chloride

By general method D from the free base, 66%. $^1$H NMR (D$_2$O) δ 9.01–7.39 (m, 26H), 4.61 (s, 9H). HRMS (FAB) (M+H) calcd 705.3090, obsd 705.3079, C$_{45}$H$_{37}$N$_8$O.

D25 5,10-di-(N-methyl-4-pyridyl)-15,20-di-(3-[2-bromoethylcarboxamido)phenyl)porphine chloride A solution of the diacid (76 mg, 0.1 mmol) and carbonyldiimidazole (46 mg, 0.26 mmol) in dry THF was stirred under reflux in an argon atmosphere for 1.5 hr. After cooling to room temperature, 2-bromoethylamine hydrobromide (0.115 g, 0.5 mmol) was added followed by 0.1 mL of triethylamine and the mixture stirred at room temperature for 24 hr. After evaporation of the solvent the residue was dissolved in 20 mL chloroform and washed with 10% sodium carbonate (10 mL) and water (twice 20 mL). TLC showed one spot, MS (CI) 917 (M+). The crude product was alkylated with methyliodide according to general procedure D to give 49 mg, 45%.

D26 5,10-tri-(N-methyl-4-pyridyl)-15,20-di-(3-acetylamino)porphine chloride

By general method D from the free base, 58%. $^1$H NMR (D$_2$O) δ 9.12–8.36 (m, 22H), 7.86–7.66 (m, 4H), 4.54 (s, 9H), 3.29 (s, 3H). HRMS (M) calcd 719.3247, obsd 719.3234, C$_{46}$H$_{39}$N$_8$O.

D27 5,10-di-(N-methyl-4-pyridyl)-15,20-di-(3-carboxamidophenyl)porphine chloride By general method D from the free base, 88%. $^1$H NMR (D$_2$O) δ; HRMS (FAB) (M) calcd 732.2961, obsd 732.2971, C$_{46}$H$_{36}$N$_8$O$_2$.

D28 5,10,15,20-tetra-(5-[2-furanyl]-N-methyl-3-pyridyl)-porphine chloride

By general method D from the free base, 61%. $^1$H NMR (D$_2$O) δ 9.42–8.94 (m, 22H), 7.55–6.56 (m, 12H), 4.54 (CH$_3$ and HOD); HRMS (FAB) (M) calcd 941.3564, obsd 941.3550, C$_{60}$H$_{45}$N$_8$O$_4$.

G1 5-(3-ethylcarbonyloxyphenyl)-10,15,20-tri-(N-methyl-4-pyridyl)]porphine

From the free base, 99%; $^1$H NMR (DMSO-d$_6$) δ 9.50 (m, 4H), 8.98–9.18 (m, 16H), 8.13 (d, J=7.5 Hz, 1H), 8.03 (m, 1H), 7.87 (t, J=8.2 Hz, 1H), 7.68 (d, J=8.3 Hz, 1H), 2.72 (q, J=7.5 Hz, 2H), 2.48 (M, 9H), 1.17 (t, J=7.5 Hz, 3H), −3.06 (s, 2H); MS (FAB) (Glycerol) m/z: 735 (M+H).

G2 Diethylene glycol di-[5-(3-hydroxyphenyl)-10,15,20-tri-(N-methyl-4-pyridyl)]porphine hexachloride By general method C, 93%; $^1$H NMR (DMSO-d$_6$) δ 9.50 (m, 4H), 8.93–9.18 (m, 16H), 7.94 (s, 2H), 7.75 (m, 4H), 7.45 (m, 2H), 4.26 (m, 4H), 3.76 (m, 4H), 2.51 & 2.86 (2×s, 6H), 2.48 (m, 12H), −3.05 (s, 4H); MS (FAB) (NBA) m/z: 1426 (M).

G3 Tetraethyleneglycol di-[5-(3-hydroxyphenyl)-10,15,20-tri-(N-methyl4-pyridyl)]porphine hexachloride By general method C, 68%; $^1$H NMR (DMSO-d$_6$) δ 9.50 (m, 4H), 8.93–9.18 (m, 16H), 7.94 (s, 2H), 7.75 (m, 4H), 7.45 (m, 2H), 4.26 (m, 4H), 3.76 (m, 4H), 3.34–3.56 (m, 8H), 2.51 & 2.86 (2×s, 6H), 2.48 (m, 12H, NCH$_3$), −3.05 (s, 4H, NH); MS (FAB) (NBA) m/z: 1514 (M).

G4 Pentaethyleneglycol di-[5-(3-hydroxyphenyl)-10,15,20-tri-(N-methyl4-pyridyl)]-porphine hexachloride By general method C, 94%; $^1$H NMR (DMSO-d$_6$) δ 9.50 (m, 4H), 8.93–9.18 (m, 16H), 7.94 (s, 2H), 7.45 (m, 2H), 4.26 (m, 4H), 3.76 (m, 4H), 3.34–3.56 (m, 12H), 2.51 & 2.86 (2×s, 6H), 2.48 (m, 12H), −3.05 (s, 4H); MS (FAB) (NBA) m/z: 1558 (M).

G5 Hexaethyleneglycol di-[5-(3-hydroxyphenyl)-10,15,20-tri-(N-methyl4-pyridyl)]porphyrin hexachloride By general method C, 95%; $^1$H NMR (DMSO-d$_6$) δ 9.50 (m, 4H), 8.93–9.18 (m, 16H), 7.94 (s, 2H), 7.75 (m, 4H), 7.45 (m, 2H), 4.26 (m, 4H), 3.76 (m, 4H), 3.34–3.56 (m, 16H), 2.51 & 2.86 (2×s, 6H), 2.48 (m, 12H), −3.05 (s, 4H); MS (NBA) m/z: 1602 (M+H).

5.1.7 Uncharged Porphyrins

D13 5,10,15,20-tetra-(4-chloro-3-nitrophenyl)porphine

By general method A from 4-chloro-3-nitrobenzaldehyde (0.8 g, 4.3 mmol) and pyrrole (0.3 mL, 4.3 mmol) in propionic acid (15 mL). Chromatography on silica eluted with chloroform gave a purple solid, 0.45 g (45%).

D14 5,10-di-(3-nitro-4-hydroxyphenyl)porphine

From dipyrromethane and 3-nitro-4-hydroxybenzaldehyde by general method B. $^1$H NMR (DMSO-d$_6$) δ 11.60 (s, 2H), 10.67 (s, 2H), 9.69 (d, J=4.5 Hz, 4H), 9.14 (d, J=4.5 Hz, 4H), 8.73 (br s, 2H), 8.43 (d, J=8.5 Hz, 2H), 7.62 (d, J=8.6 Hz, 2H), −3.24 (s, 2H); MS m/z: 585, 567, 249; HRMS (M+H) calcd 585.1523, obsd 585.0220, C$_{32}$H$_{21}$N$_6$O$_6$.

D15 5,10-di-(4-nitro-3-hydroxyphenyl)porphine

From dipyrromethane and 4-nitro-3-hydroxybenzaldehyde by general method B. $^1$H NMR (DMSO-d$_6$) δ 11.53 (s, 2H), 10.71 (s, 2H), 9.71 (t, J=4.6 Hz, 4H), 9.17 (d, J=4.5 Hz, 4H), 8.37 (d, J=8.6 Hz, 2H), 8.01 (s, 2H), 7.89 (d, J=8.4 Hz, 2H), −3.34 (s, 2H); MS m/z: 585, 567, 249.

D16 5,10-di-(3-nitrophenyl)porphine

By general method B from dipyrromethane and 3-nitrobenzaldehyde, a purple solid 0.110 g, 74%. mp 233–235 _C. $^1$H NMR (CDCl$_3$) δ 10.46 (s, 2H), 9.47 (br s, 4H), 9.16 (s, 2H), 8.89 (br s, 4H), 8.69 (br t, 2H), 8.56 (br d, 2H), 8.08–7.92 (m, 4H), −3.50 (s, 2H); HRMS (CI) (M+H) calcd 553.1624, obsd 553.1619, C$_{32}$H$_{21}$N$_6$O$_4$.

D17 5,10,15,20-tetra-(4-methoxy-3-hydroxyphenyl)porphine

Condensation of pyrrole and 3-hydroxy-4-methoxybenzaldehyde (1:1) in propionic acid by general method A. Chromatography on silica eluted with chloroform:methanol (25:1) gave a purple solid, 36%.

D18 5,10-di-(4-methoxy-3-hydroxyphenyl)porphine

From dipyrromethane and 4-methoxy-3-hydroxybenzaldehyde. MS (CI) m/z: 555 (M+H), 540. $^1$H NMR (DMSO-d$_6$) δ 10.58 (s, 2H), 9.61 (d, J=4.6 Hz, 4H), 9.53 (s, 2H), 9.10 (d, J=4.6 Hz, 4H), 7.71 (d, J=1.6 Hz, 2H), 7.63 (d, J=8.0 Hz, 2H), 7.39 (d, J=8.4 Hz, 2H), −3.25 (s, 2H).

5.2 Example 2

Telomerase Inhibition

Inhibition of Telomerase Activity in HeLa Cell-Free Extract. The effects of porphyrins on telomerase activity have been examined in HeLa cells, which express high levels of processive telomerase activity. The HeLa cell-free system has been routinely used as a reference in evaluating the effects of standard chemotherapeutics and novel agents on telomerase activity in human tumor cell lines and primary tumors (Raymond et al., 1996; Zhu et al., 1996; Holt et al., 1997). In this study, solutions of TMPyP4, TMPyP4.In$^{III}$, TMPyP4.Cu$^{II}$, QP3, and QP3.In$^{III}$ at 2.5, 5, 10, and 25 μM were added to the telomerase reaction mixture containing extract from 2,000 HeLa cells and the assay run. FIG. 7A illustrates the dependence of telomerase activity on porphyrin concentration. The $^{32}$P signal intensity due to incorporation of [α-$^{32}$P]-dGTP into the ladder produced by the action of telomerase was quantitated in each lane. An IC$_{50}$ (porphyrin concentration which inhibited 50% of the telomerase activity in the control) was determined from a plot of relative activity against porphyrin concentration (FIG. 7B). The interpolated IC$_{50}$ values were in the range of 5–40 μM.

5.3 Example 3

In vitro evaluation of cytotoxicity

Cytotoxicity of Porphyrins Against Tumor and Normal Cells. To identify tumor models most suitable for evaluation and development of novel agents that target telomerase and/or telomeres, a systematic study was undertaken to measure telomerase activity and telomere length in a range of human tumor cell lines. HeLa telomerase activity and median telomere length were used as reference points. Telomerase activity and telomere length have been examined in a total of 39 human tumor cell lines representing breast, prostate, leukemia, lymphoma, ovary, colon, non-small and small cell lung carcinomas. Tumor cell lines such as breast, prostate, and lymphoma consistently showed high levels of telomerase, in the range of 20–40% of the activity in HeLa cells (average values) and had relatively short telomeres (usually <6 kilobases). These tumor types (breast, prostate, and lymphoma) were used as the models to examine biological effects of the novel G-quadruplex interactive agents.

Within each tumor type, cell lines were selected to represent a spectrum of telomerase activities. In breast carcinoma cell lines, telomerase activity relative to HeLa cells was high in MCF7 (40%), intermediate in MDA-231 (30%), and very low in BT20 (<1% HeLa control). Some of these cell lines were estrogen-sensitive (MDA-231) and the others estrogen-resistant (BT20, MCF7, HS578t). Prostate carcinoma cells were androgen receptor positive (LNCaP) and negative (DU145, PC3) and both had intermediate telomerase activity (30%). Raji lymphoma cell line expressed intermediate telomerase activity (30%), Daudi lymphoma cells had low telomerase activity (<20%). Most porphyrins showed low cytotoxicity against the tumor cell lines examined and against normal human fibroblasts (Table I). No apparent correlation was observed between cytotoxic effects of porphyrins and the endogenous levels of telomerase activity or the steroid hormone receptor status in the tumor cell lines.

To determine whether the cationic porphyrins exhibit differential toxicity between tumor and normal cells, as shown by some other quaternary aromatic cations (Lampidis et al., 1983; Nadakuvakaren et al., 1985), MTT assays using TMPyP4 or TMPyP4.Pt$^{II}$ were run in a matched pair of human breast cell lines. Hs578t cells represented a transformed phenotype and expressed intermediate telomerase activity; Hs578Bst, normal breast cells, did not express detectable telomerase activity. The cationic porphyrins showed similar cytotoxic $IC_{50}$ values in normal and transformed breast cells (FIG. 8). Thus, the general toxicity of porphyrins appears not to be telomerase-related as telomerase inhibition occurs at concentrations below the toxic threshold for the cells.

Effects of TMPyP4 in Intact MCF7 Human Breast Carcinoma Cells. To determine the long-term effects of TMPyP4 on whole cells, MCF7 breast carcinoma cells were cultured in the continuous presence of 1, 10, and 100 μM TMPyP4. The porphyrin solution was freshly added to the medium from the concentrated stock at each passage of the cells (every 3–4 days). On days 4, 8, and 15, the cells were lysed and the telomerase activity was measured in the extracts. A clear concentration-dependent loss of telomerase activity in the presence of TMPyP4 was observed at days 4 and 8 (FIG. 9A). The results were quantitated and expressed as percentage of control telomerase activity (FIG. 9B). The inhibition of telomerase activity was also time dependent (FIG. 9C). Even at 1 and 10 μM TMPyP4 (below the cytotoxic $IC_{50}$ for MCF7 cells), the inhibition of telomerase activity showed a concentration dependence. The inhibition of telomerase activity by 1, 10, and 100 μM TMPyP4.Pt$^{II}$ was also concentration-dependent at days 4 and 8, but TMPyP4.Pt$^{II}$) was a less potent inhibitor than TMPyP4. The extent of inhibition of telomerase by the two porphyrins in whole MCF7 cells thus parallels their relative potency of telomerase inhibition in the HeLa cell-free system.

Recent reports addressed the link between the cell cycle, regulation of telomerase activity and its possible repression during quiescence and cell differentiation. Diverse cell cycle blockers, including growth factors and cytotoxic agents, which caused inhibition of telomerase activity, also arrested the cells in G2/M (Zhu et al., 1996). Telomerase activity is repressed in quiescent cells that exited the cell cycle (Holt et al., 1997). The inventors examined whether the treatment of MCF7 cells with TMPyP4 affected the cell cycle. A fraction of the MCF7 cells from the long-term treatment with 100 μM TMPyP4 (in which telomerase activity was measured) was also subjected to the analysis of the cell cycle at days 4, 8, and 15. A time-dependent gradual increase in the G2/M phase was observed in cells cultured in the presence of 100 μM TMPyP4 (FIG. 10).

Telomeres shorten at an average rate of 65–100 base pairs per cell division (Counter et al., 1992). To observe a significant effect of an agent on telomere length, e.g., shortening the telomeres by >1 kilobase in MCF7 cells (5.7 kbases), a minimum of 11–17 population doubling times will be required. No detectable effects on telomere shortening were seen in MCF7 cells grown in the presence of TMPyP4 (1 and 10 μM) by day 8 (about 6 population doublings), or in the presence of 1 and 10 μM TMPyP4.Pt$^{II}$ by day 28 (24 population doublings).

Cytotoxicity of the compounds to human breast cancer cells in vitro was assessed using a panel of cell lines representing estrogen receptor-positive (BT20, MCF-7m), and a pair of estrogen receptor-negative, transformed breast (11S578t) and normal breast (HS578Bst) cells. The results are shown in Table 2.

TABLE 2

Cytotoxicity and Telomerase Inhibition Data

| Cell line | Method | TMPyP4 (μM) | Pt(II)TMPyP4 (μM) |
|---|---|---|---|
| HS578t | Thy | 327 ± 75.1 | 214 ± 49 |
|  | Cell count | >10 | — |
| HS578 Bst | Thy | >100 |  |
| MCF-7M | Thy | 70.8 ± 9.01 | 434 ± 386 |
|  | MTT | 7.76 ± 1.13 | 74.79 ± 31.93 |
| BT20 | Cell count | >100 |  |
| HeLa | MTT | 18.7 ± 3.89 | 135.6 ± 34.76 |
| Telomerase Inhibition |  | 15 | 15 |

Thy: tritiated thymine assay (n = 3 ± SEM)
Cell count (n = 3 ± SEM)
MTT (n = 3 ± SEM)
TMPyP4 = Tetra(N-methyl-4-pyridyl)porphyrin chloride
Pt(II)TMPyP4 = Platinum(II)tetra(N-methyl-4-pyridyl)porphyrin chloride The growth of tumor cells in the presence or absence of the disclosed porphyrin compounds was assessed in a semiautomatic radiometric assay that utilizes inhibition of the conversion of $^{14}$C-glucose to $^{14}CO_2$. This method is suitable for rapid screening of large numbers of chemical entities against human breast cancer cells and normal human bone marrow cells. For the short-term (1 hour) exposure studies, human breast cancer cells or human bone marrow preparation cells were pretreated with inhibitors, washed and resuspended in fresh media. The cells were aseptically seeded in rubber-stoppered vials containing tissue culture media and $^{14}$C-glucose freshly flushed with 5% $CO_2$. For continuous exposure, the inhibitors were added directly to the vials before incubation at 37° C. The amount of $^{14}CO_2$ produced at days 3, 6, 9 and 14 was measured in a BACTEC System 460 unit (Sheithauer, et al., 1986; Hanasuke, et al., 1989; Von Hoff, et al., 1985). The growth index of inhibitor-treated cells was compared with the untreated controls and used to determine the $IC_{30}$ values. An independent assessment of the effects of the novel compounds on DNA synthesis-related enzymes was achieved by the measurement of thymidine uptake into cells using standard means (Elston, et al., 1982).

5.4 Example 4

Effects of Novel G-quadruplex Interactive Ligands on Telomerase Activity in Human Breast Cancer Cells Breast cancer cells MCF-7m, BT20, HS578t and normal HS578Bst cells were grown in culture in T75 flasks ($10^6$ cells/flask). The cells were cultured in the continuous presence of the compounds of interest at concentrations corresponding to $2 \times IC_{50}$, $IC_{50}$, and $0.5 \times IC_{50}$ for 1, 4, 8, and 12 days. See FIG. 4A and FIG. 4B showing concentration and time dependence of tetra(N-methyl-4-pyridyl)porphyrin on telomerase activity in MCF-7m breast tumor cells. The cells were harvested and freeze-thawed and the extracts used to measure telomerase activity using the Dynabeads method. The compounds listed in Table 3 were tested in a similar manner with results as shown in 7A and FIG. 7B.

TABLE 3

| No. | Compound |
|---|---|
| 1 | Tetra-(4-aminophenyl)porphyrin |
| 2 | Tetra-(3-aminophenyl)porphyrin |
| 3 | Tetra-(2-aminophenyl)porphyrin |
| 4 | 5,15-Diphenyl-10,20-di(N-methyl-4-pyridyl)porphyrin chloride |
| 5 | 5,10-Diphenyl-15,20-di(N-methyl-4-pyridyl)porphyrin chloride |
| 6 | Tri(N-methyl-4-pyridyl)phenylporphyrin chloride |
| 7 | Tetra(N-methyl-3-pyridyl)porphyrin chloride |
| 8 | Tetra(N-methyl-2-pyridyl)porphyrin chloride |
| 9 | 5,15-Diphenyl-10,20-di(N-methyl-3-pyridyl)porphyrin chloride |
| 10 | Tri(N-methyl-3-pyridyl)phenylporphyrin chloride |
| 11 | Tetrabenzoporphyrin |
| 12 | Phthalocyanine |
| 13 | Tetra(N-methyl-3-quinolyl)porphyrin chloride |
| 14 | Copper(II)tetraaminophthalocyanine |
| 15 | Zinc(II)tetraaminophthalocyanine |
| 16 | Tetra(N-ethanesulphonato-4-pyridyl)porphyrin |
| 17 | Tetra(N-propanesulphonato-4-pyridyl)porphyrin |
| 18 | Tetra(N,N-dimethyl-4-aminophenyl)porphyrin |
| 19 | Ethylenediamineprotoporphyrin-IX |
| 20 | Platinum(II)tetra(N-methyl-4-pyridyl)porphyrin chloride |

5.5 Example 5
Stabilization of Quadruplex

The inherent photosensitizing activity of porphyrins was used to probe the binding site of TMPyP4 on quadruplex DNA. A single-stranded sequence bearing four human telomeric repeats was treated with TMPyP4 and then exposed to light. The cleavage patterns are shown in FIG. 5A. In the absence of potassium ions (lanes 1–4), uniform cleavage at purines was observed. However, under conditions that promote quadruplex formation (100 mM KCl, lanes 5–8), a clear selectivity for cleavage at the 5'-ApG-3' step at G1 and G7, and 5'-GpT-3' step at G6 and G12 was observed. This may be related to the secondary structure of the quadruplex: whatever the folding topology of the sequence, these four guanines are necessarily members of the same tetrad (an example fold is shown in FIG. 5B). Thus, these data imply that the porphyrin is stacked externally on the G1, G6, G7, G12 tetrad. This result is consistent with the UV and NMR results.

The ability of potassium ions and quadruplex-interactive compounds to inhibit telomerase has been ascribed to stabilization of DNA quadruplexes (Zahler et al., 1991; Sun et al., 1997). The potassium-dependent block to DNA polymerase has been shown to be a selective and sensitive indicator of the formation of intramolecular quadruplexes in a DNA template, and this assay (Weitzmann and Woodford, 1996) has been adapted to demonstrate the stabilization of quadruplex by small molecules. A single-stranded DNA template, which included four telomeric repeats, was taken, and an 18-base primer complementary to the 5'-end was extended using Taq DNA polymerase. In Tris buffer, in the absence of $K^+$ or $Na^+$ (FIG. 13A, lane 1) there was only a weak stop at the site corresponding to the start of the putative quadruplex (marked by an arrow). However, upon addition of TMPyP4, these bands became more intense in a concentration-dependent manner (see lanes 2–6).

The stabilization of the quadruplex by TMPyP4 was further demonstrated by examining its temperature dependence. The block to Taq DNA polymerase may be relieved by thermal denaturation of the quadruplex, since the intensity of the pause decreased with increasing temperature (FIG. 13B, lanes 1–5). Lanes 6–10 in FIG. 13B show the same phenomenon in the presence of TMPyP4. The intense bands at the pause site persisted up to 65° C. in the presence of TMPyP4; whereas, in the control lanes there was a significant loss of intensity by 55° C. Thus the binding of TMPyP4 to quadruplex exaggerated the block posed to Taq DNA polymerase and increased the melting temperature of the quadruplex.

Finally, the inventors have found TMPyP4 to be a potent inhibitor of human telomerase. There is a concentration-dependent effect of TMPyP4 on the ladder produced by telomerase extension of an 18-base primer in a quantitative, cell-free primer-extension assay using $(\alpha\text{-}^{32}P)$-dGTP. The relative telomerase inhibition was determined from phosphorimager measurement of the intensity of the bands in the telomerase extension assay, and the $IC_{50}$ of TMPyP4 was determined as $6.5\pm1.4\,\mu M$. The pattern of ladders formed by telomerase extension of the 18-base primer in the presence of TMPyP4 was quite different from that seen in the control reaction. In the presence of TMPyP4, the amounts of the first and second extension products were little affected, but a significant reduction in the formation of products corresponding to more than four extensions was seen. Since a quadruplex structure cannot be formed until after at least two rounds of extension, this result supports the contention that TMPyP4 mainly interacts with quadruplex structures formed during the telomerase reaction. Previously the inventors observed that an anthraquinone inhibited telomerase by targeting G-quadruplex structures generated during the telomerase reaction and produced a change in the pattern of ladder formation (Sun et al., 1997), which is similar to that observed in the presence of TMPyP4. A wide variety of analogues of TMPyP4 has been evaluated in this assay and rough structure activity relationship determined, which are consistent with a mechanism of action involving intercalation.

5.6 Example 6
Nuclear Localization of Porphyrins

Several reports indicate that porphyrins localize specifically in tumor tissue, although sites of subcellular localization may vary widely with porphyrin structure and net charge (De Paolis et al., 1985). Porphyrin TMPyP4 has been shown to rapidly accumulate (within min) in the nuclei of cultured human dermal fibroblasts (Georgiou et al., 1994). To gain insight into the subcellular distribution of cationic porphyrins, the inventors have cultured MCF7 cells with 0, 50, or 100 $\mu M$ TMPyP4 for 7 days. When MCF7 cells were grown in the presence of 50 $\mu M$ TMPyP4, porphyrin concentration in the nuclear pellet was 1.39 nmoles/$10^6$ cells, and the cytoplasm contained 47.3 pmoles/$10^6$ cells (3.3% of the TMPyP4 concentration measured in the nuclear fraction). In cells cultured in the presence of 100 $\mu M$ TMPyP4, the concentration of TMPyP4 in the nuclear fraction was 7.81 nmoles/$10^6$ cells, while the cytoplasmic fraction contained 434 pmoles/$10^6$ cells (that is, 5.5% of the porphyrin concentration in the nuclear pellet). These measurements did not differentiate between free and bound porphyrin, consequently the measured values are likely to be an underestimate of the local porphyrin concentration associated with the DNA fraction. Assuming that the volume of the nucleus is about $\frac{1}{100}$ of the cell and that the volume of $10^6$ cells is about 10–100 $\mu l$, the calculated concentration of TMPyP4 in the nucleus (1.4–78 mM) greatly exceeds that of the cytoplasm (0.47–434 μM) and can readily approach the telomerase $IC_{50}$ seen in the cell-free system.

To examine whether porphyrin in the nucleus was associated with chromosomal DNA, the inventors examined fluorescence in metaphase spreads prepared from cells cultured in the presence of the cationic porphyrin. From a preliminary assessment of intrinsic fluorescence in solution, porphyrin QP3.In$^{III}$ was selected as the strongest flourophore in the TMPyP4 and QP3 series. MCF7 cells were cultured in the continuous presence of 40 μM QP3.In$^{III}$ for 3 days. After that time, the cells were washed, fixed, and used for preparation of metaphase spreads. Direct evidence for the chromosomal localization of QP3.In$^{III}$ porphyrin is shown in FIG. 11. These findings are consistent with the known high affinity of the cationic porphyrins for DNA and indicate that porphyrins can accumulate in the nuclei of intact tumor cells at concentrations possibly exceeding those in the surrounding medium.

5.7 Example 7
Chromosomal Effects in Sea Urchin Embryos

Sea urchin embryos may be a useful model for examining effects of novel agents that target telomere and/or telomerase due to their rapid growth (initially, one division every 60 min). The embryos express low levels of processive telomerase activity. Telomeric repeats sequences and telomere length in sea urchins are identical to humans (Lejnine et al., 1995).

The inventors examined whether treatment of the embryos with G-quadroplex interactive agents can cause observable chromosomal abnormalities. A time course of the embryo development was followed in the presence of 10 μM and 100 μM concentrations of TMPyP4 or TMPyP4.Pt$^{II}$. At 150 min after fertilization, no definitive differences were seen between controls and embryos treated with either porphyrin at 10 μM. At 100 μM TMPyP4, the condensed chromosomes were longer than in the untreated controls (FIG. 12). Qualitatively similar results were observed in embryos treated with TMPyP4.Pt$^{II}$, but the effects were not so pronounced. At later time points, in the control embryos the polyploid nuclei had undergone several rounds of chromosome replication and mitosis. The TMPyP4 and TMPyP4.Pt$^{II}$-treated embryos had fewer cells, many very misshapen and variable in size relative to the controls. Many of the embryos had variably-sized, diffuse nuclei and apparently a higher percentage of cells in mitosis. In general, the porphyrin-treated embryos were less Feulgen-stained than controls, indicating that DNA synthesis is partially suppressed or slowed in the presence of these compounds. However, despite appearing morphologically quite abnormal, because they are both polyspermic and treated with G-quadruplex interactive agents, the embryos were quite viable, showing the first signs of ciliary motility at 9 h. Thus, the porphyrins were generally non-toxic to the embryos.

5.8 Example 8
Structure Activity Relationships

Cationic porphyrins have been identified which are effective inhibitors of human telomerase. From data pertaining to a wide range of analogues a basic SAR has been determined, viz.: the face of the porphyrin must be available for stacking; the positively charged substituents are important but may be interchanged and combined with hydrogen bonding groups; substitution is only tolerated on the meso positions of the porphyrin and the size of the substituents should to be matched to the width of the grooves in which they lie. These factors are all consistent with a model in which the porphyrins stack externally on the G-tetrads of quadruplex, placing the meso substituents in each of the four grooves. Using this data, novel compounds have been designed and synthesized with improved activity over the lead porphyrin, TMPyP4.

The cationic porphyrins represent a very promising class of compounds for the development of clinical telomerase inhibitors. For a compound to be useful it must have a significant therapeutic window between its activity against telomerase and the onset of cytotoxic effects. This is clearly so with the porphyrins, for example TMPyP4 has cell free telomerase $IC_{50}$ about 12 μM but its cytotoxic $IC_{50}$ against a panel of normal and transformed breast and prostate cell lines is in the range 50–200 μM. Furthermore, evidence exists for the uptake and concentration of TMPyP4 in the nuclei of cells grown in culture and for its accumulation in tumor tissue in mice. Thus the cationic porphyrins have a number of properties that render them attractive candidates for development as telomerase inhibitors for the treatment of patients with cancer. The data presented herein lay the foundations for a program of drug development to achieve the dual aims of efficacy and selectivity in vivo.

The validity of telomerase as a selective target for drug therapy has recently been questioned. In mice deficient in telomerase RNA it was found that the absence of telomerase activity and consequent severe shortening of telomeres did not reduce the tumorigenicity of murine cells. However, we have found that cellular effects following administration of TMPyP4 may not only be related to telomerase inhibition but also to disruption of other G-quadruplex structures, leading to more rapid onset of chromosomal instability, cell senescence and other consequences of telomere malfunction than could be accounted for by consideration of telomerase inhibition and concomitant telomere shortening alone.

Groups of compounds were selected to determine the effects of steric and electronic variations on the TMPyP4 structure: coordinated metal ion, number of charges on the meso substituents, disposition of charges around the porphyrin ring, position of the charged group on the pyridyl and quinolyl substituents, bulk of substituents, effects of different quaternizing groups (Me, Et, HO—Et, $CH_2OAc$). A wide range of natural porphyrins and their close analogues was also investigated.

5.8.1 Stacking Interactions

The data in Table 4 show the effects of coordination to different metal ions on the inhibition of telomerase by TMPyP4. Across the first row transition metals there is a general relationship between the coordination chemistry of the metal ion and the degree of telomerase inhibition. Those complexes where the porphyrin offered an unhindered face for stacking were the better inhibitors, that is the square planar Cu(II) complex and pyramidal Zn(II). In contrast, octahedral complexes, in which the metal ion carried two strongly bound axial ligands which posed a block to stacking interactions, were generally less active, for example Mn(III) and Mg(II). In the complexes of TMPyP4 with second and third row metal ions the larger ions do not fit in the center of the porphyrin but lie above the plane of the porphyrin ring so that even the formally square planar Au(III) complex was a poor inhibitor. This was exacerbated in the lanthanide complexes where the metal ions lie well above the plane of the porphyrin in 10 or 12 co-ordinate sites.

The DNA photocleavage activity of the free porphyrins is not a desirable property in a telomerase inhibitor. However, this activity may be modified by the presence of a metal ion: for example, the Cu(II) ion with its unpaired d-electron is able to quench the excited state of the porphyrin and so reduce its photocleavage activity. The data in Table 4 indicate that copper (II) complexes may be used without detriment to the telomerase inhibitory activity of the porphyrin.

TABLE 4

Telomerase Inhibition by Metalloporphyrins

| Porphyrin | Metal | Notes | % Inhibition (25 μM) | $IC_{50}$ (μM) |
|---|---|---|---|---|
| TMPyP4 | H2 |  | 88 | 6.5 ± 1.4 |
|  | ZnII | py | 88 |  |
|  | CoII |  | 83 |  |
|  | FeIII | oh | 63 |  |
|  | NiII | sqpl←→oh | 42 |  |
|  | MnIII | oh | 37 |  |
|  | CuII | sqpl | 75 | 13 ± 1.9 |
|  | MgII | oh | 42 |  |
|  | PtII | sqpl | 69 |  |
|  | PdII | sqpl | 41 |  |
|  | TiO | py | 28 |  |
|  | VO | py | 2 |  |
|  | Sn |  | 19 |  |
|  | InIII | py | 47 | 35 ± 4.5 |
|  | AlIII | py | 56 |  |
|  | AuIII | sqpl | 23 |  |
|  | GaIII |  | 27 |  |
|  | ErIII | * | -2 |  |
|  | EuIII | * | 12 |  |
|  | GdIII | * | 24 |  |
|  | YbIII | * | 40 |  |
|  | LuIII | * | 27 |  |
|  | PrIII | * | 23 |  |
|  | TbIII | * | 17 |  |
| QP3 | H2 |  | 56 | 17 ± 8 |

Notes: Except for Lanthanides all other ligands were chloride. Abbreviations: sqpl, square planar; oh, octahedral; py, pyramidal; * lanthanides are 10 or 12 coordinate with the metal above the plane of the porphyrin, mixture of water, chloride and imidazole ligands.

The data in Table 5 provide further evidence of the importance of stacking interactions to the process by which telomerase is being inhibited. When a porphyrin bears meso aryl substituents there is usually some rotation possible about the bond between the porphyrin and aryl rings. However, where the meso aryl substituent has a group other than a hydrogen atom on the 2-position, steric hindrance prevents any rotation about the bond between the two rings and the compound has a permanent twist. Moreover, the 2-substituent lies partly over the face of the porphyrin thus posing a block to stacking. This is demonstrated by the data in Table 4: as the N-methyl group of the pyridine is moved from the 4 to the 3 and the 2 position there is a dramatic loss of activity in the 2-pyridyl analogue. A similar situation pertained for the quinolyl series where the 4 quinolyl compound, which places a the fused benzo ring over the face of the porphyrin, was the most inactive of all the tetracationic compounds.

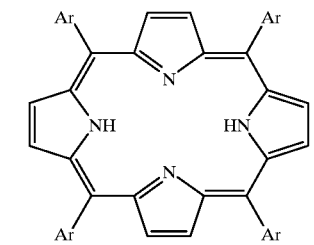

TABLE 5

Stacking Ability (Group 2)

| Compound | Ar | % Inhibition (25 μM) |
|---|---|---|
| TMPyP4 | 4-(N-methylpyridinium-yl) | 66 |
| B7 | 3-(N-methylpyridinium-yl) | 54 |
| B8 | 2-(N-methylpyridinium-yl) | 0 |
| QP3 | 4-(N-methylquinolinium-yl) | 14 |
| B13 |  | 3 |

TABLE 5-continued

Stacking Ability (Group 2)

| Compound | Ar | % Inhibition (25 μM) |
|---|---|---|
| QP4 (B21) | 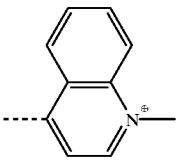 | 0 |
| TAP (B23) | 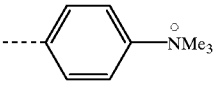 | 6 |
| B19 | Ethylenediamine protoporphyrin-IX | 0 |

5.8.2 Substituent Bulk

The grooves of the intramolecular quadruplex are not all the same size (ref patel) a very narrow grove lies opposite a wide groove with two intermediate-width grooves between. The compounds in Table 6 were designed to explore the importance of fitting the bulk of the meso substituents to the width of the grooves. Thus replacing one of the 3-quinolyl groups of QP3 with a 3-pyridyl group results in activity equivalent to the tetra-3-pyridyl compound. This can be rationalized in terms of the smaller pyridyl group better fitting into the minor groove of the quadruplex.

TABLE 6

Substituent Bulk

| Compound | $Ar^1$ | $Ar^2$ | $Ar^3$ | $Ar^4$ | % Inhibition 25 μM |
|---|---|---|---|---|---|
| TMPyP4 |  | 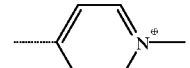 | 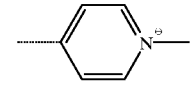 |  | 60 |
| B7 | 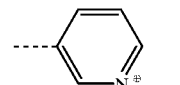 | 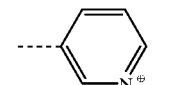 | 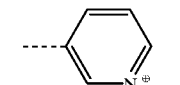 | 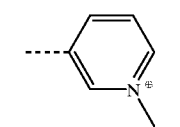 | ≈50 |
| D12 | 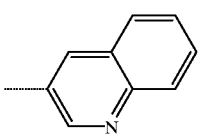 | 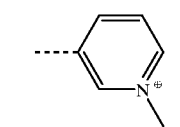 | 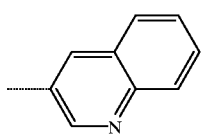 | | 80 |

TABLE 6-continued

Substituent Bulk

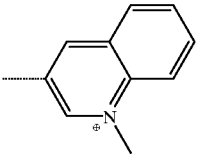

| Compound | Ar¹ | Ar² | Ar³ | Ar⁴ | % Inhibition 25 μM |
|---|---|---|---|---|---|
| QP3 | 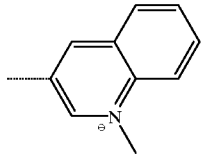 | 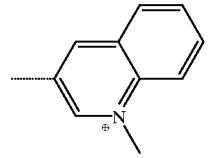 | 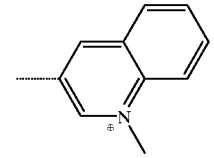 |  | 28 |

5.8.3 Charge Effects

The significance of the number and positioning of the charged groups is shown by the data of Table 7. In the 4-pyridyl series (compounds, qq-vv) the general trend is that the telomerase inhibition is charge dependent. However, there are two possible isomers of the dicationic compound: with the charged groups on either the 5,10 (cis) or 5,15 (trans) positions of the porphyrin. Curiously, the 2⁺ trans compound exhibited equivalent activity against telomerase to the 3⁺ compound. This pattern was repeated in the 3-pyridyl series. Thus is seems that the trans orientation may be a better fit for threading through the quadruplex to place the charged groups in opposite grooves.

TABLE 7

Charge Effects

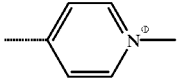

| Compound | Ar¹ | Ar² | Ar³ | Ar⁴ | Charge | % Inhibition (25 μM) |
|---|---|---|---|---|---|---|
| TMPyP4 | 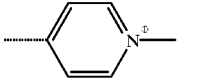 | 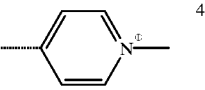 | 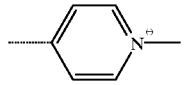 | 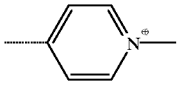 | 4⁺ | 62 |
| B6 | 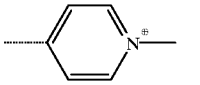 | 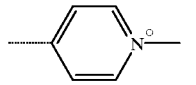 | 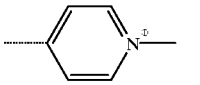 | Ph | 3⁺ | 15 |
| B4 | 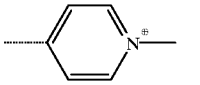 | Ph | 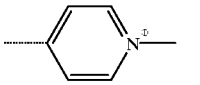 | Ph | 2⁺ trans | 30 |

TABLE 7-continued
Charge Effects
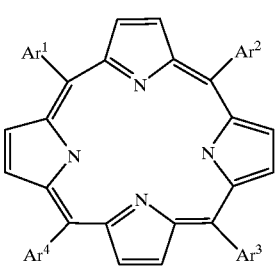
| Compound | Ar¹ | Ar² | Ar³ | Ar⁴ | Charge | % Inhibition (25 μM) |
|---|---|---|---|---|---|---|
| B5 |  | 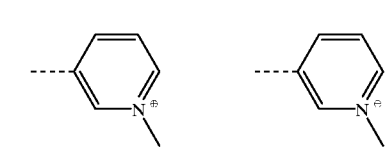 | Ph | Ph | 2⁺ cis | 20 |
| B24 | 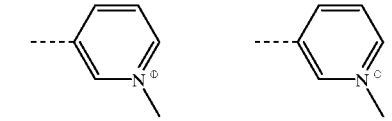 | Ph | Ph | Ph | 1⁺ | 34 |
| B7 | 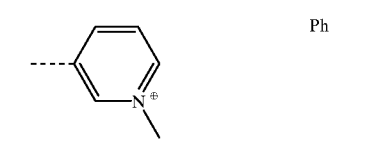 | 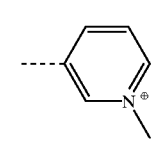 |  | 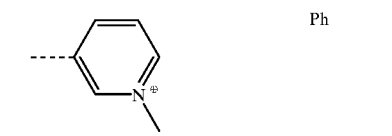 | 4⁺ | 88 |
| B10 |  | 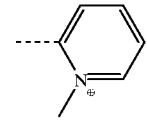 | | Ph | 3⁺ | 42 |
| B9 | | Ph | | Ph | 2⁺ trans | 18 |
| B22 | | | Ph | Ph | 2⁺ cis | 20 |
| B25 | | Ph | Ph | Ph | 1⁺ | 35 |
| D9 | | 4-Tol | 4-Tol | 4-Tol | 1⁺ | 31 |
| B26 | Ph | Ph | Ph | | 1⁺ | 0 |

TABLE 7-continued

Charge Effects

| Compound | Ar¹ | Ar² | Ar³ | Ar⁴ | Charge | % Inhibition (25 μM) |
|---|---|---|---|---|---|---|
| QP3 | 3-(N-methyl)quinolinium | 3-(N-methyl)quinolinium | 3-(N-methyl)quinoline (neutral) | 3-(N-methyl)quinolinium | 4+ | 37 |

5.8.4 Effect of Pyridine-N-alkyl Substituents

Table 8 investigated the effect of different pyridine-N-alkyl substituents. In all cases where the positive charge was maintained there was little effect in activity across the series Me, Et, hydroxyethyl, acetoxymethyl. However, the two compounds resulting in zwitterions, and hence zero net charge, showed no activity under the conditions used.

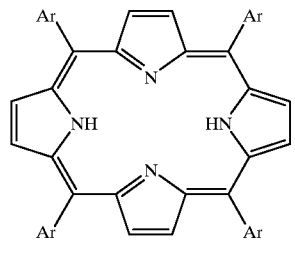

TABLE 8

R Groups (Group 1)

| Compound | Ar | % Inhibition (25 μM) |
|---|---|---|
| TMPyP4 | 4-(N-methyl)pyridinium | 67 |
| D1 | 4-(N-ethyl)pyridinium | 55 |
| D3 | 4-(N-hydroxyethyl)pyridinium | 55 |

TABLE 8-continued

R Groups (Group 1)

| Compound | Ar | % Inhibition (25 μM) |
|---|---|---|
| D2 | 4-(N-acetoxymethyl)pyridinium (OAc) | 15 |
| B16 | 4-pyridinium-N-CH₂CH₂SO₃⁻ (zwitterion) | 0 |
| B17 | 4-pyridinium-N-CH₂CH₂CH₂SO₃⁻ | 14 |
| B7 | 3-(N-methyl)pyridinium | 55 |
| D4 | 3-(N-ethyl)pyridinium | 33 |

TABLE 8-continued
R Groups (Group 1)
| Compound | Ar | % Inhibition (25 μM) |
|---|---|---|
| D5 | 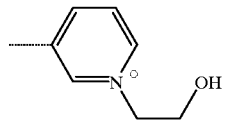 | 52 |
| D6 | 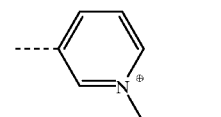 | 33 |
| QP3 | 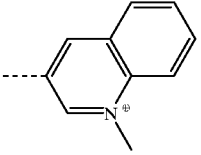 | 32 |
5.8.5 Importance of Hydrogen Bonding Groups
Table 9 introduces the concept that uncharged compounds bearing appropriate hydrogen bonding groups may be telomerase inhibitors.
TABLE 9
Uncharged Hydrogen bonders
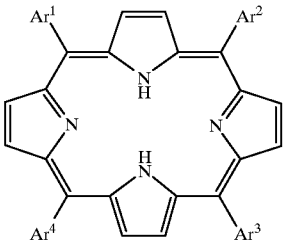
| Compound | Ar¹ | Ar² | Ar³ | Ar⁴ | % Inhibition 25 μM |
|---|---|---|---|---|---|
| TMPyP4 | 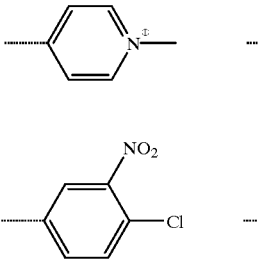 | 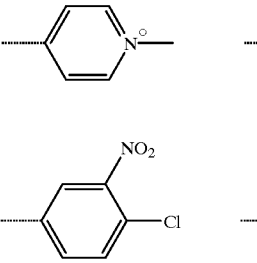 | 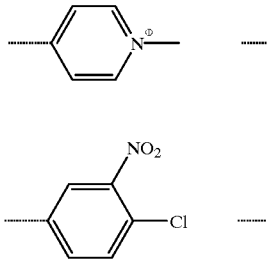 | 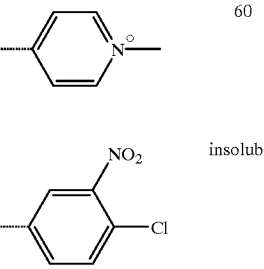 | 60 |
| D13 | 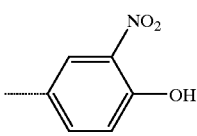 | 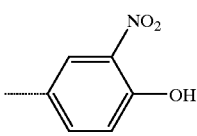 | 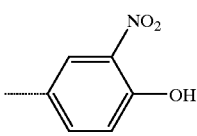 | 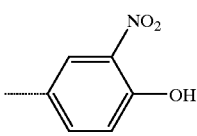 | insoluble |
| D14 | 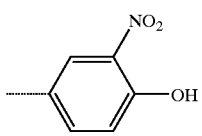 | H | 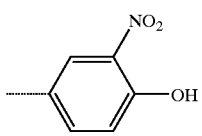 | H | 55 |

TABLE 9-continued

Uncharged Hydrogen bonders

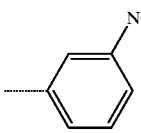

| Compound | Ar¹ | Ar² | Ar³ | Ar⁴ | % Inhibition 25 μM |
|---|---|---|---|---|---|
| D16 | 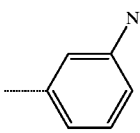 | H | 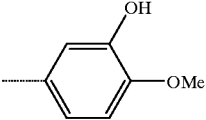 | H | insoluble |
| D17 | 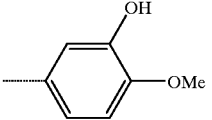 | 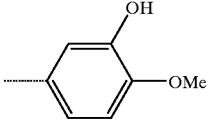 | 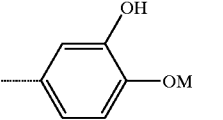 | 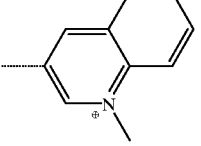 | 50 |
| QP3 | 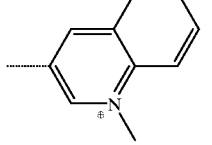<br>phenyl | 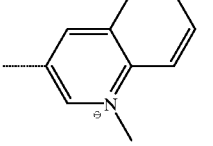<br>phenyl | 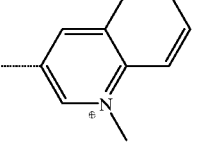<br>phenyl | <br>phenyl | 28 |

This idea was developed further in the data of Table 10 where charged and hydrogen bonding groups were mixed. Thus combination of two cationic and two hydrogen bonding substituents gave compounds with good activity (D19, D20, D26, D27). The exception to this were the carboxy compounds (D21, D22, D23) where ionization of the carboxylate at physiological pH would reduce the intrinsic electrostatic affinity of the compounds for DNA. The bromoethylamide compound D25 also has the potential to alkylate or cross-link DNA.

TABLE 10

| Compound | Ar¹ | Ar² | Ar³ | Ar⁴ | % Inhibition (25 μM) |
|---|---|---|---|---|---|
| TMPyP4 | 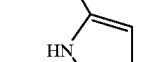 |  | 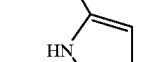 |  | 60 |

TABLE 10-continued

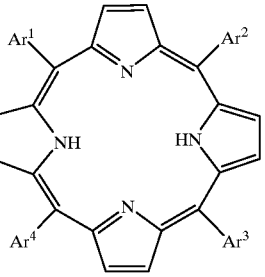

| Compound | Ar¹ | Ar² | Ar³ | Ar⁴ | % Inhibition (25 μM) |
|---|---|---|---|---|---|
| D19 | 4-N-methylpyridinium | 4-N-methylpyridinium | 4-N-methylpyridinium | 3-NO₂-phenyl | 85 |
| D20 | 4-N-methylpyridinium | 3-NO₂-phenyl | 4-N-methylpyridinium | 3-NO₂-phenyl | 70 |
| D21 | 4-N-methylpyridinium | 3-CO₂H-phenyl | 4-N-methylpyridinium | 3-CO₂H-phenyl | 48 |
| D22 | 4-N-methylpyridinium | 4-N-methylpyridinium | 4-N-methylpyridinium | 3-CO₂H-phenyl | 18 |
| D23 | 4-N-methylpyridinium | 4-N-methylpyridinium | 4-N-methylpyridinium | 4-CO₂H-phenyl | 10 |
| D24 | 4-N-methylpyridinium | 4-N-methylpyridinium | 4-N-methylpyridinium | 3-CONH₂-phenyl | 55 |
| D25 | 4-N-methylpyridinium | 3-CONHCH₂CH₂Br-phenyl | 4-N-methylpyridinium | 3-CONHCH₂CH₂Br-phenyl | 95 |
| D26 | 4-N-methylpyridinium | 4-N-methylpyridinium | 4-N-methylpyridinium | 3-NHCOCH₃-phenyl | 85 |

TABLE 10-continued

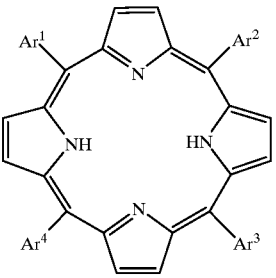

| Compound | Ar¹ | Ar² | Ar³ | Ar⁴ | % Inhibition (25 μM) |
|---|---|---|---|---|---|
| D27 | 4-(N-methyl)pyridinium | 3-benzamide (CONH₂) | 4-(N-methyl)pyridinium | 3-benzamide (CONH₂) | 85 |
| QP3 | N-methylquinolinium | N-methylquinolinium | N-methylquinolinium | N-methylquinolinium | 30 |

Given the model of the porphyrins stacking on the G-tetrads, compound D28, Table 11, was designed specifically to hydrogen bond the guanine(2)H's on the edges of the G-tetrad immediately below the stacking site. An increase in activity was observed.

TABLE 11

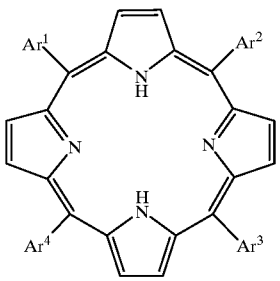

| Compound | Ar¹ | Ar² | Ar³ | Ar⁴ | % Inhibition |
|---|---|---|---|---|---|
| TMPyP4 | 4-(N-methyl)pyridinium | 4-(N-methyl)pyridinium | 4-(N-methyl)pyridinium | 4-(N-methyl)pyridinium | 60 |

TABLE 11-continued

| Compound | Ar¹ | Ar² | Ar³ | Ar⁴ | % Inhibition |
|---|---|---|---|---|---|
| D28 | 5-methyl-N-methyl-pyridinium-3-yl furan | 5-methyl-N-methyl-pyridinium-3-yl furan | 5-methyl-N-methyl-pyridinium-3-yl furan | 5-methyl-N-methyl-pyridinium-3-yl furan | 86 |
| D | 5-methyl-N-methyl-pyridinium-3-yl thiophene | 5-methyl-N-methyl-pyridinium-3-yl thiophene | 5-methyl-N-methyl-pyridinium-3-yl thiophene | 5-methyl-N-methyl-pyridinium-3-yl thiophene | |
| QP3 | N-methyl-quinolinium-3-yl | N-methyl-quinolinium-3-yl | N-methyl-quinolinium-3-yl | N-methyl-quinolinium-3-yl | 30 |

5.8.5 Porphyrin Dimers

Since there are theoretically two stacking sites in each quadruplex, some porphyrin dimers were designed which might simultaneously stack on both ends of the stacked G-tetrads. Flexible oligomers of ethylene glycol (which might also hydrogen bond in the grooves) were used for initial investigations, Table 12. These resulted in additive activity, that is the dimers inhibited telomerase with activity similar to an equivalent concentration of the porphyrin monomer.

TABLE 12
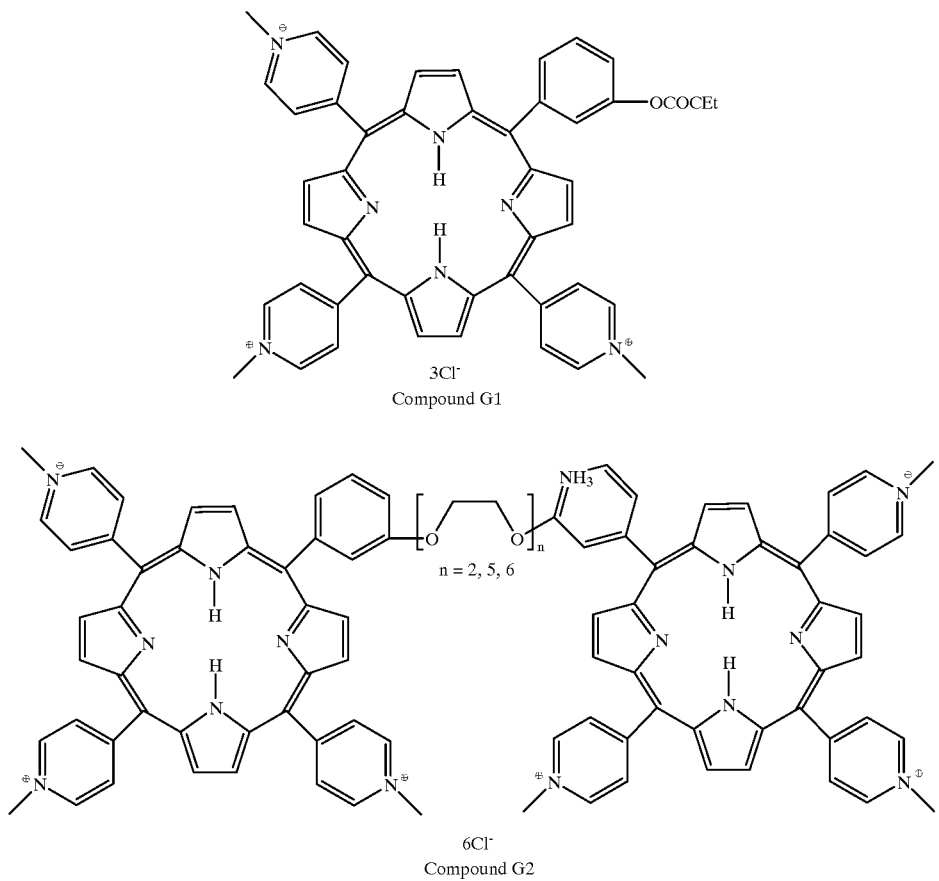
| Compound | Concentration/$\mu$M | % Inhibition |
| --- | --- | --- |
| TMPyP4 | 25 | 60 |
| QP3 | 25 | 30 |
| G1 | 25 | 50 |
| G2 n = 2 | 12.5 | 60 |
| G4 n = 5 | 12.5 | 45 |
| G5 n = 6 | 12.5 | 55 |
5.8.7 Anilines
Table 13 shows the results of studies with selected aniline derivatives.

TABLE 13

Anilines

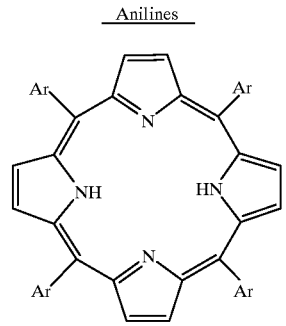

| Ar | Compound | % Inhibition (25 μM) |
|---|---|---|
| 4-NH$_2$Ph | B1 | 50 |
| 3-NH$_2$Ph | B2 | 15 |
| 2-NH$_2$Ph | B3 | 3 |
| 4-NMe$_2$Ph | B4 | 47 |
| 4-NMe$_3$$^+$Ph | B23 | 18 |
| TMPyP4 | | 70 |
| QP3 | | 20 |

5.8.8 Fused Benzoporphyrin and Phthalocyanine Systems

These data investigated effects of fused ring porphyrin systems and generally showed little activity against telomerase. Surprisingly, copper tetraazaphthalocyanine even when quaternized, (compound D7), showed only slight activity although the coppertetraamino analogue, (compound B14), was active. These data imply, with the data for the tentacle porphyrin, that substitution is only tolerated on the meso positions of the porphyrin—an observation reinforced by the data of Table 14.

TABLE 14

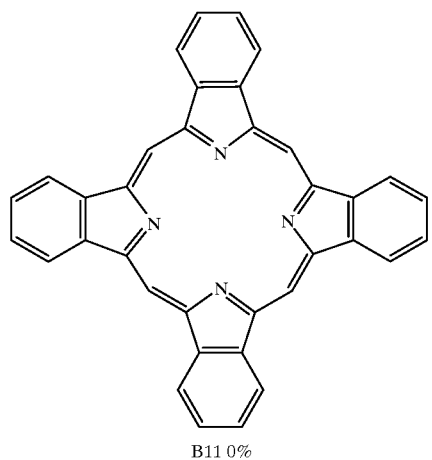

B11 0%

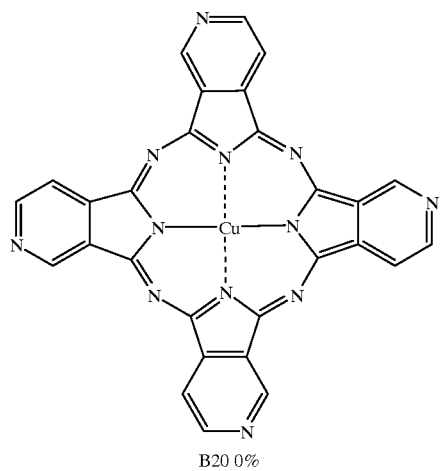

B20 0%

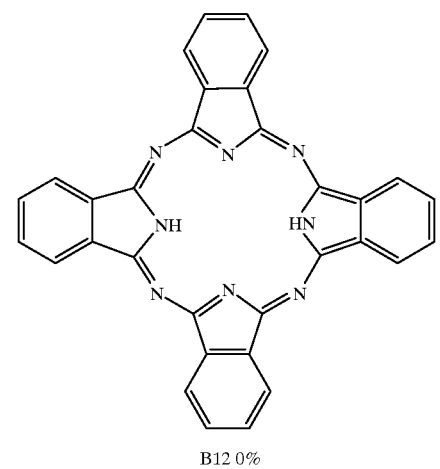

B12 0%

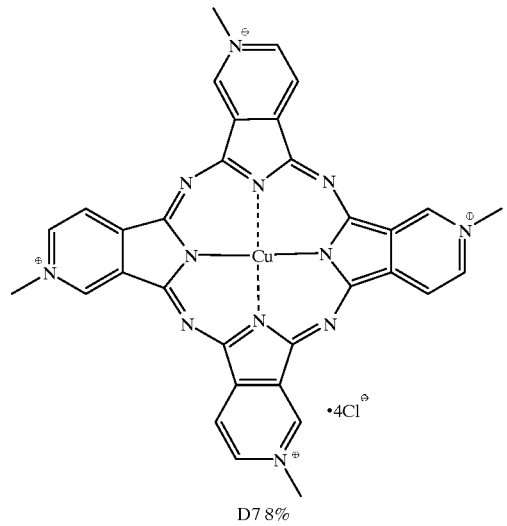

D7 8%

TABLE 14-continued
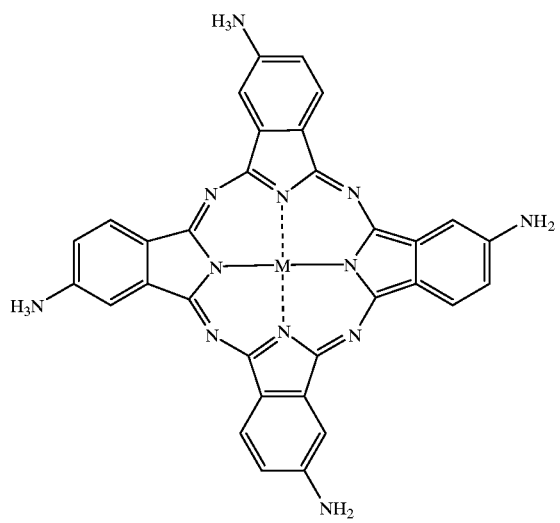
B14, M = Cu²⁺ 75%
B15, M = Zn²⁺ 8%
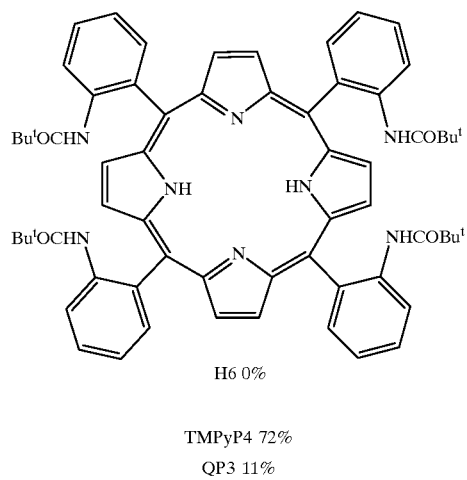
H6 0%
TMPyP4 72%
QP3 11%
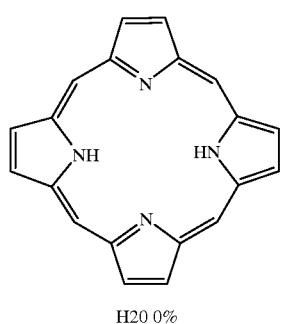
H20 0%
TABLE 14-continued
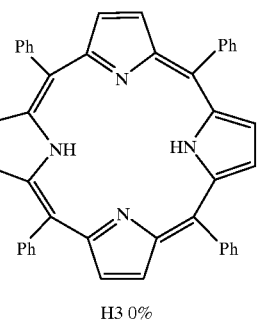
H3 0%
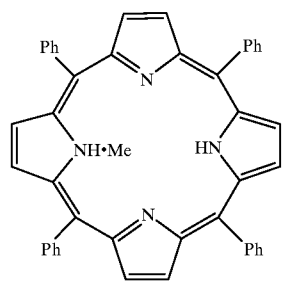
H4 0%
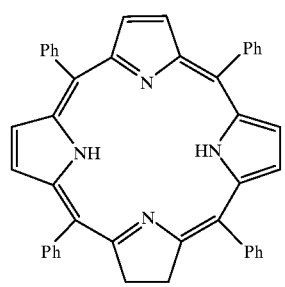
H5 0%
Concentration of the compound was tested at 25 $\mu$M. Percents represent amount of inhibition.
5.8.9 Naturally Occurring Porphyrins
An extensive range of compounds showed little activity against telomerase. Results are shown in Table 15.

TABLE 15

| Porphyrin | R2 | R2 | R3 | R4 | R5 | R6 | R7 | R8 | % Inhibition |
|---|---|---|---|---|---|---|---|---|---|
| TMPyP4 | | | | | | | | | 64 |
| QP3 | | | | | | | | | 39 |
| H1 | Et | Et | Et | Et | Et | Et | Et | Et | 12 |
| H2 | Me | Et | Me | Et | Me | H | Et | Me | 0 |
| H7 | Me | CH₂CO₂Me | CH₂CH₂CO₂Me | Me | Me | SO₃H | Me | SO₃H | 14 |
| H8 | Me | CH₂CH₂CO₂Me | CH₂CH₂CO₂Me | Me | Me | Ac | Me | Ac | 24 |
| H9 | Me | CH₂CH₂CO₂Me | CH₂CH₂CO₂Me | Me | Me | Br | Me | Br | 14 |
| H10 | Me | CH₂CH₂CO₂Me | CH₂CH₂CO₂Me | Me | Me | CH(OH)CH₃ | Me | CH(OH)CH₃ | 0 |
| H11 | Me | CH₂CH₂CO₂H | CH₂CH₂CO₂H | Me | Me | CH(OH)CH₃ | Me | CH(OH)CH₃ | 20 |
| H12* | Me | CH₂CH₂CO₂Me | CH₂CH₂CO₂Me | Me | Me | CH=CH₂ | Me | CH=CH₂ | 18 |
| H14(1) | Me | CH₂CH₂CO₂H | CH₂CH₂CO₂H | Me | Me | Et | Me | Et | 42 |
| H15 | Me | CH₂CH₂CO₂Me | CH₂CH₂CO₂Me | Me | Me | CH=CH₂ | Me | CH=CH₂ | 6 |
| H16 | Me | CH₂CH₂CO₂H | CH₂CH₂CO₂H | Me | Me | CH=CH₂ | Me | CH=CH₂ | 6 |
| H17 | Me | CH₂CH₂CO₂Me | CH₂CH₂CO₂Me | Me | Me | CH=CH₂ | Me | CH=CH₂ | 17 |
| H18 | Me | CH₂CH₂CO₂H | CH₂CH₂CO₂H | Me | Me | CH=CH₂ | Me | CH=CH₂ | 16 |
| H19 | Me | CH₂CH₂CO₂Na | CH₂CH₂CO₂Na | Me | Me | CH=CH₂ | Me | CH=CH₂ | 33 |
| H21 | Me | CH₂CH₂CO₂Me | CH₂CH₂CO₂Me | Me | Me | Me | Me | Me | 5 |
| H22 | CH₂CO₂Me | CH₂CH₂CO₂H | CH₂CH₂CO₂H | CH₂CO₂Me | CH₂CO₂Me | CH₂CH₂CO₂Me | CH₂CH₂CO₂Me | Me | 19 |
| H23* | CH₂CO₂H | CH₂CH₂CO₂H | CH₂CH₂CO₂H | CH₂CO₂H | CH₂CO₂H | CH₂CH₂CO₂H | CH₂CH₂CO₂H | CH₂CO₂Me | 4 |
| H24* | Me | CO₂Et | Me | CH₂CH₂CO₂Et | Me | Et | Me | Et | 18 |
| H25 | Me | CH₂CH₂CH₂OH | CH₂CH₂CH₂OH | Me | Me | Et | Me | Et | 23 |
| H26 | Me | CH₂CH₂CH₂OH | CH₂CH₂CH₂OH | Me | Me | CH=CH₂ | Me | CH=CH₂ | 24 |
| H27 | Me | Et | Me | Et | CH₂CH₂CO₂Et | Me | Me | Me | 0 |
| H28 | Me | CH₂CH₂CO₂H | Me | CH₂CH₂CO₂H | Me | Ac | Me | Ac | 0 |
| H29 | Me | CH₂CH₂CO₂Me | Me | CH₂CH₂CO₂Me | Me | Me | Me | Me | 23 |
| H30 | Me | CH₂CH₂CO₂H | Me | CH₂CH₂CO₂H | Me | CHO | Me | CHO | −10 |
| H32 | Me | H | Me | CH₂CO₂Me | Me | Et | Me | Et | 0 |

*: .2HCl; (1) FeCl complex.

5.9 Example 9
In Vivo Breast Tumor Studies

A MX-1 human breast tumor adjuvant model employed nude mice (Harlan Sprague Dawley, Inc.). The mice were implanted s.c. by trocar with fragments of MX-1 mammary carcinomas harvested from S.C. growing MX-1 tumors in nude mice hosts. When tumors were approximately 5 mm×5 mm in size (about 10 days after inoculation), the animals received cytoxan at 200 mg/kg. After tumors regressed (fifteen days after cytoxan administration), the animals were pair-matched into groups of mice, each of which was eartagged and followed individually throughout the experiment. The i.p. daily administration of TMPyP4 at 10 and 20 mg/kg five times weekly, began the day the animals were pairmatched (Day 1). TMPyP4 20 mg/kg was administered for 47 days. At the 10 mg/kg dose, TMPyP4 was administered continuously to the end of the study.

Mice were weighed twice weekly and tumor measurements were taken by calipers twice weekly, starting on Day 1. These tumor measurements were converted to mg tumor weight by a well-known formula, and from these calculated tumor weights, the termination date for each individual mouse was determined. Mice were euthanized when their tumors reached approximately 2 grams. Time to tumor recurrence and survival were monitored during the study.

Results of the treatment are shown in Table 16

TABLE 16

TMPyP4 vs. MX-1 Adjuvant Human Breast Tumor Xenograft

| Group | n | # CR's | % CR's | # of Recur | Avg Day of Recur | # Recur at 2 g | MDS | # of Toxic Deaths | # of Survivors | # Remaining w/Tumors | Mean Tumor Wt. |
|---|---|---|---|---|---|---|---|---|---|---|---|
| Control | 20 | 10 | 50% | 1 | 16 | 1 | 44 | 0 | 9 | 0 | n/a |
| TMPyP4 20 mg/kg | 20 | 15 | 75% | 9 | 19.33 | 8 | 67.4 | 1 | 6 | 0 | n/a |
| TMPyP4 10 mg/kg | 20 | 18 | 90% | 8 | 25 | 6 | 55 | 1 | 11 | 1 | 11.52 mg |

| Group | n | # Partial Shrinkage | MDS-Partial Shrinkages | # PS Remaining | Mean Tumor Wt. |
|---|---|---|---|---|---|
| Control | 20 | 10 | 40.3 | 0 | n/a |
| TMPyP4 20 mg/kg | 20 | 5 | 44.6 | 0 | n/a |
| TMPyP4 10 mg/kg | 20 | 2 | 36.0 | 0 | n/a |

6.0 REFERENCES

The following references, to the extent that they provide exemplary procedural or other details supplementary to those set forth herein, are specifically incorporated herein by reference.

Anatha and Sheardy, *Biophys. J.*, 72:A422, 1997.

Biasco, Lee, Hande, Samper, Lansdorp, DePinho, Greider, *Cell*, 91:25–34, 1997.

Blackburn, "Structure and Function of Telomeres," *Nature*, 350:569–573, 1991.

Blackburn, *Nature*, 350:569–573, 1991.

Blasco, Lee, Hande, Samper, Lansdorp, DePinho, Greider, *Cell*, 91:25–34, 1997.

Burger, Double, Newell, *Eur. J. Cancer*, 33:638–644, 1997.

Chen, Behrens, Behrens, Czerniak, Dexter, Dusak, Fredericks, Gale, Gross, Jiang, Kirshenbaum, McRipley, Papp, Patten, Pertella, Seitz, Stafford, Sun, Sun, Wuonola, Von Hoff, *Anti-Cancer Drugs*, 4:447–457, 1993.

Counter, Avillion, Le Feuvre, Stewart, Greider, Harley, Baccetti, *EMBO J.*, 11:1921–922, 1992.

De Paolis, Chandra, Charalambides, Bonnett, Magnus, *Biochem. J.*, 226:757–766, 1985.

Elston, D. L., Osborne, C. K., Livingston, R. B., and Von Hoff, D. D. (1982) Methods for Determining Chemosensitivity in Double Layer Agar Culture: Labeling Index Depression and Colony Count Inhibition. *Stem Cells*, 2, 34–44.

Feng, Funk, Wang, Weinrich, Avillon, Chiu, Adams, Chang, Allsop, Yu, *Sci.*, 269:1236–1241, 1995.

Fletcher, Salazar, Chen, "Human Telomerase Inhibition by 7-Deaza-2'-deoxypurine Nucleoside Triphosphates," *Biochem.*, 35:15611–15617, 1996.

Georgiou, Ahmet, Houlton, Silver, "Measurement of the Rate of Subcellular Localization of Porphyrins in Cells Using Fluorescence Digital Imaging Microscopy," *Photochem. Photobiol.*, 59:419–422, 1994.

Han, Hurley, *Biochem.*, 35:7993–8001, 1996.

Hanasuke, U., Hanasuke, A., Clark, G. M., Tsen, S. D., Buchok, J. and Von Hoff, D. D. (1989). A New In Vitro Screening System for Anticancer Drugs for the Treatment of Non-small Cell Lung Cancer. *Selective Cancer Therapeut.*, 5, 97–111.

Haq, I., Ladbury, J. E., B. Z. and Jenkins, T. C. (1996). Molecular Anchoring of Duplex and Triplex DNA by Disubstituted Anthracene-9,10-diones: Calorimetric, UV Melting and Competition Dialysis Studies. *J. Amer. Chem. Soc.*, 118, 10693–10701.

Holt Aisner, Shay, Wright, *Proc. Natl. Acad. Sci. USA*, 94, 1997.

Kim, Piatyszek, Prowse, Harley, West, Ho, Coviello, Wright, Weinrich, Shay, *Science*, 266:2011–2015, 1994.

Kirk, Harmon, Reichardt, Sedat, Blackburn, *Science*, 275:1478–1481, 1997.

Lampidis, Bernal, Summerheys, Chen, *Cancer Res.*, 43:716–720, 1983.

Lejnine, Makarov, Langmore, *Proc. Natl. Acad. Sci. USA*, 92:2393–2397, 1995.

Lingner, Hughes, Shevchenko, Mann, Lundblad, Cech, *Sci.*, 276:561–567, 1997.

Lipscomb, Zou, Presnell, Woo, Peek, Plaskon, Williams, *Biochem.*, 35:2818–2823, 1996.

Marzilli, L. G., Banville, D. L., Zon, G. and Wilson, W. D. (1986). Pronounced $^1$H and $^{31}$P NMR Spectral Changes on meso-Tetrakis (N-methylpyridinium-4-yl)porphyrin Binding to Poly[d(G-C)]-Poly[d(G-C)] and to Three Tetradecaoligodeoxyribonucleotides: Evidence for Symmetric Selective Binding to 5'-CG'3' Sequences. *J. Amer. Chem. Soc.*, 108, 4188–4192.

Mata, Joshi, Palen, Pirruccello, Jackson, Elias, Paige, Medlin, Iveson, *Toxicol. Appl. Pharmacol.*, 144:189–197, 1997.

Morin, *J. Natl. Cancer Inst.*, 87:859–861, 1995.

Mossman, *J. Immunol. Meth.*, 65:55–63, 1983.

Nadakuvakaren, Nadakavakaren, Summerheys, Chen, *Cancer Res.*, 45:6093–6099, 1985.

Norton, Piatyszek, Wright, Shay, Corey, *Nature Biotechnol.*, 14:615–619, 1996.

Parkinson, *Brit. J. Cancer,* 73:1–4, 1996.

Pasternack, R. F., Gibbs, E. and Villafranca, J. W. (1983). Interaction of Porphyrins with Nucleic Acids. *Biochemistry,* 22, 5409–5417.

Raymond, Sun, Chen, Windie, Von Hoff, *Curr Opinion Biotech.,* 7:583–591, 1996.

Salazar, Thompson, Kerwin, Hurley, *Biochem.* 35:16110–16115, 1996.

Sheithauer, W., Clark, G. M., Moyer, M. P. and Von Hoff, D. D. (1986). Novel Screening System for Selection of Anticancer Drugs for Treatment of Human Colorectal Cancer. *Cancer Res.,* 31, 8112–8119.

Shippen-Lentz, D. and Blackburn, E. H. (1990). Functional Evidence for a RNA Template in Telomerase. *Science,* 247, 546–552.

Strahl and Blackburn, *Mol. Cell Biol.,* 16:53–65, 1996.

Strahl and Blackburn, *Nucl. Acids Res.,* 22:893–900, 1994.

Sun, Thompson, Cathers, Salazar, Kerwin, Trent, Jenkins, Neidle, Hurley, L. H. *J. Med. Chem.,* 40:2113–2116, 1997.

Von Hoff, D. D., Forsch, B. J. and Warpel, L. (1985). Use of a Radiometric System to Screen for Antineoplastic Agents: Correlation With a Human Tumor Cloning System. *Cancer Res.,* 45, 4032–4238.

Wang and Patel, *Biochem.,* 32:8112–8119, 1992.

Wang and Patel, "Solution Structure of the Human Telomeric Repeat d[AG$_3$(T$_2$AG$_3$)$_3$] G-Quadruplex," *Structure,* 1:263–282, 1993.

Ward, Skorobogaty, Dabrowiak, "DNA Binding Specificity of a Series of Cationic Metalloporphyrin Complexes," *Biochem.,* 25:7827–7833, 1986.

Weitzmann, Woodford, Usdin, *J. Biol. Chem.,* 34:20958–20964, 1996.

Wheelhouse, Sun, Hurley, *Proc. Amer. Assoc. Cancer Res.,* 38:637, 1997.

Zahler, Williamson, Cech, Prescott, "Inhibittion of Telomerase by G-Tetrad DNA Structures," *Nature,* 350:718–720, 1991.

Zhu, Kumar, Mandal, Sharma, Sharma, Dhingra, Sokoloski, Hsiao, Narayan, *Proc. Natl. Acad. Sci. USA,* 93:6091–6095, 1996.

---

What is claimed is:

1. A method of modifying telomerase or telomere function, comprising interacting a porphyrin with telomeric DNA wherein the porphyrin has a formula:

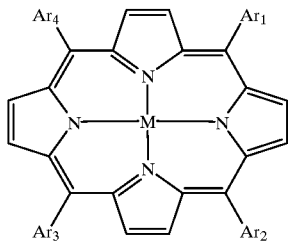

where $Ar_1$, $Ar_2$, $Ar_3$ and $Ar_4$ are H or independently

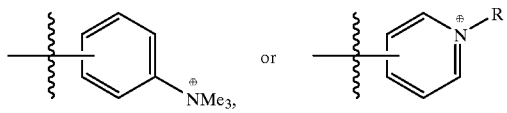

where R is H, lower alkyl, —$CH_2CH_2OH$, $CH_2OAc$, or —$CH_2CH_2CH_2SO_3^-$,

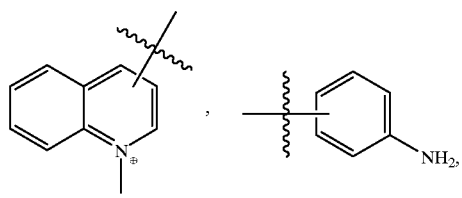

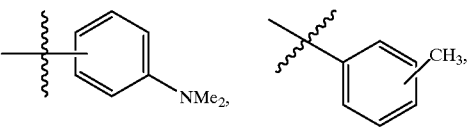

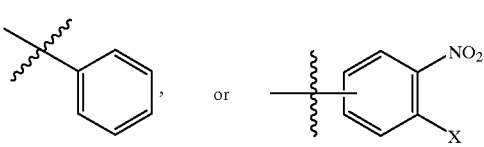

where X is H, OH, OMe, Cl or Me,

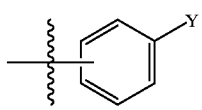

where Y is —$CO_2H$, $CONH_2$, $CONHCH_2CH_2Br$ or $NHCOCH_3$, or where $Ar_1$, $Ar_2$, $Ar_3$ and $Ar_4$ are independently

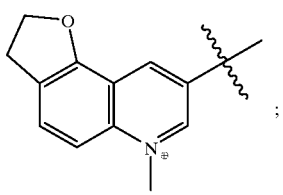

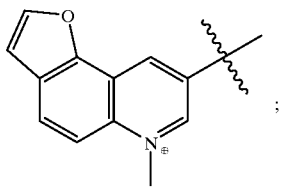

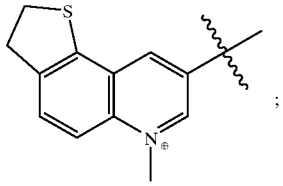

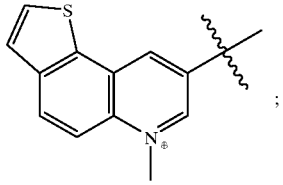

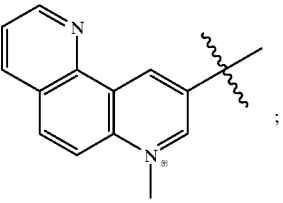

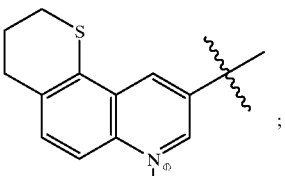

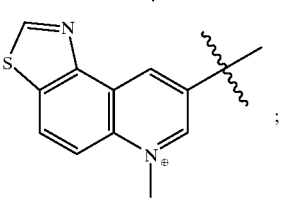

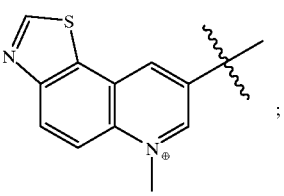

-continued
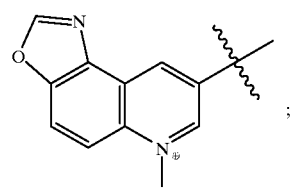
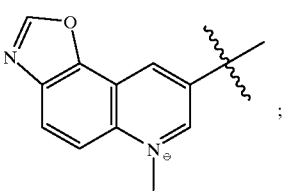
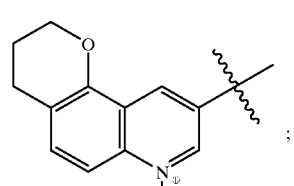
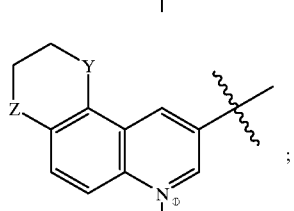
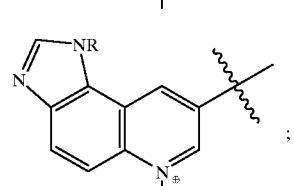
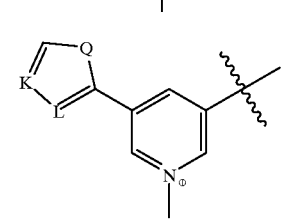
where Q is O, S, NH or NMe; K=CH, N, L=N, CH where R is lower alkyl, and A is CH, NH, NMe, O or S; or where Ar$_1$, Ar$_2$, Ar$_3$ and Ar$_4$ are independently;
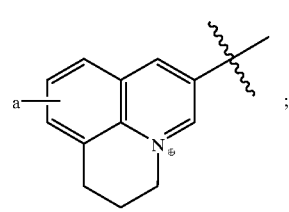
-continued
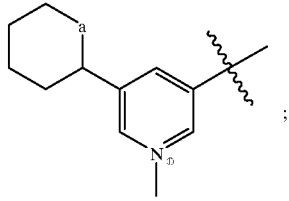
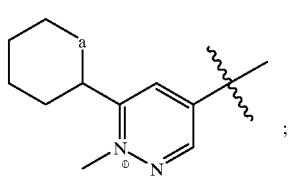
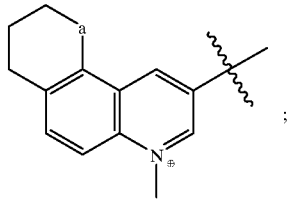
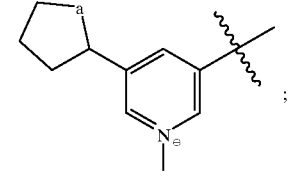
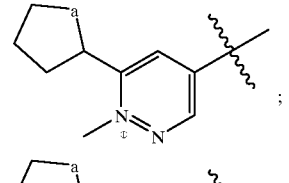
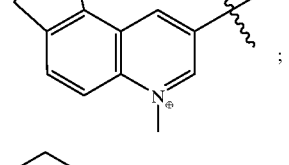
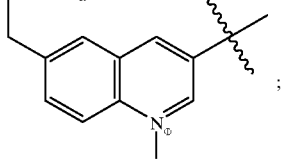
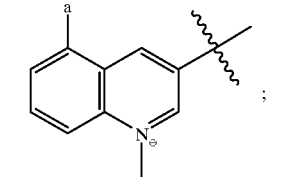
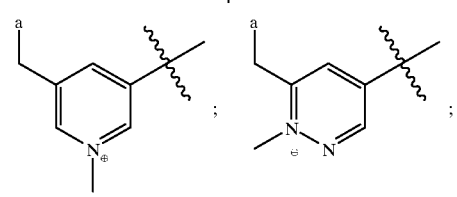

-continued

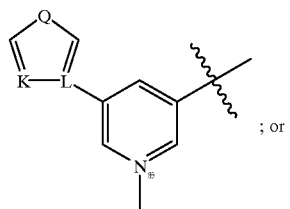

Where Q = O, S, NH or NMe
K = CH or N
L = N or CH or

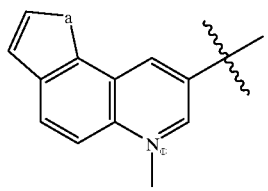

where a is NH, NH₂, NHMe, NMe₂, NMe, OH, OMe, SMe, O or S;

or where Ar₁, Ar₂, Ar₃ and Ar₄ are independently;

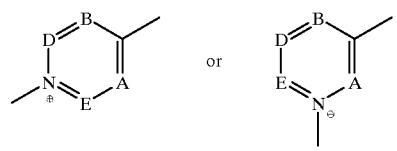

where A, B, D and E are independently N or CH; or where Ar₁, Ar₂, Ar₃ and Ar₄ are independently

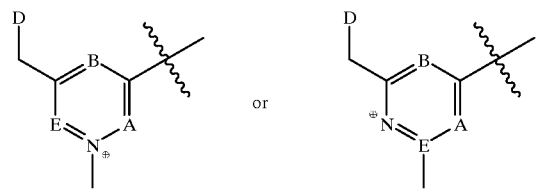

where A, B and E are independently N or CH and D is NH₂, NHMe, NMe₂, OH, SH, SMe or CF₃;

and M is 2H⁺ or a metal ion selected from the group consisting of Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb and Eu.

2. The method of claim 1 wherein the telomerase modifying is telomerase inhibition.

3. The method of claim 1 wherein the porphyrin is 5,10,15,20-tetra-(N-methyl-3-quinolyl)porphine.

4. The method of claim 1 wherein the porphyrin is Pt(II) 5,10,15,20-tetra-(N-methyl-3-quinolyl)porphine.

5. A method of modifying telomerase or telomere function, comprising interacting a porphyrin with telomeric DNA wherein the porphyrin has a formula:

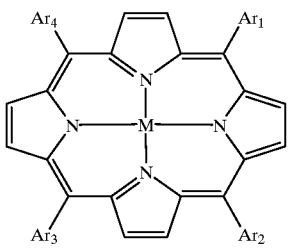

where Ar¹, A², Ar³ and Ar₄ are independently

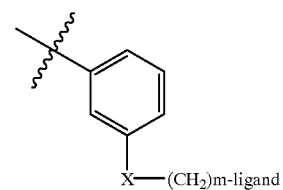

where m is 0–3. x is O, NH, CO, or

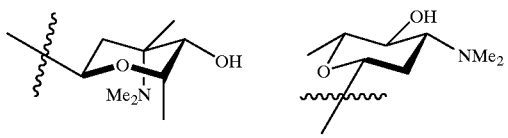

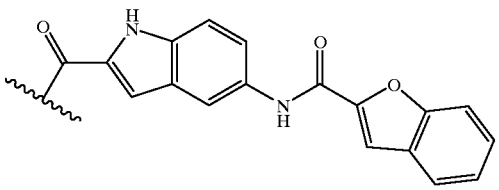

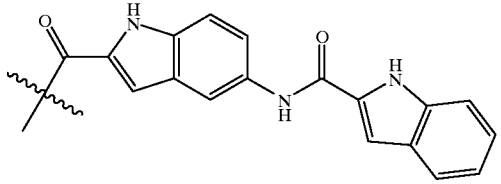

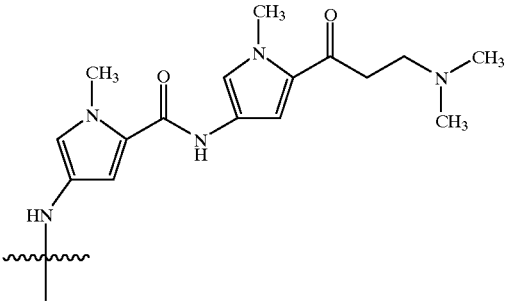

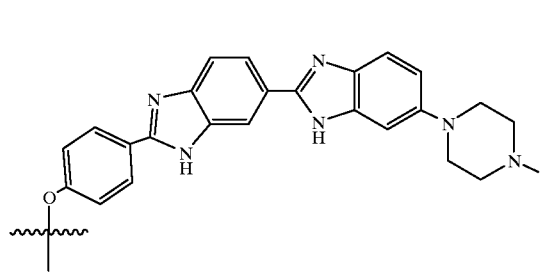

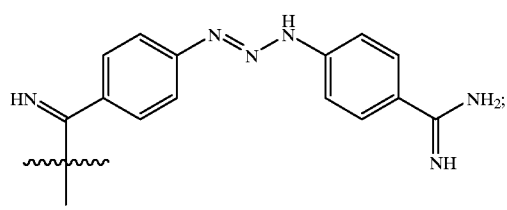

and M is 2H⁺ or CH₂ and where ligand is a metal ion selected from the group consisting of Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb and Eu.

6. A method for cleaving telomeric DNA, comprising contacting the telomeric DNA with a porphyrin having a formula:

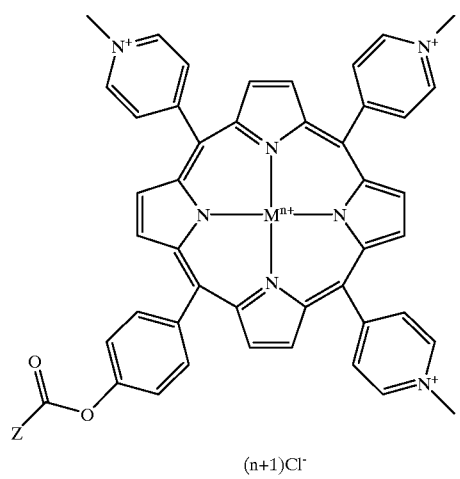

where Z is Fe.EDTA, n is 1–3 and M is a metal ion selected from the group consisting of Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb and Eu.

7. A method for covalently modifying telomeric DNA, comprising reacting telomeric DNA with a porphyrin having a formula;

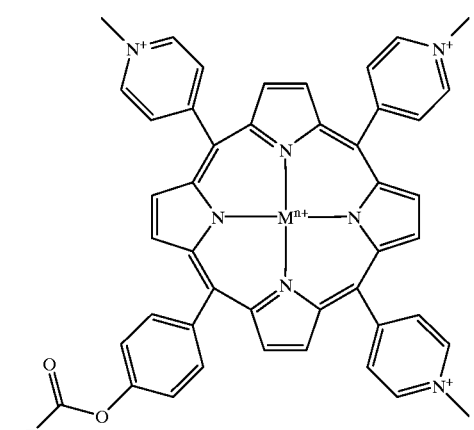

where Z is

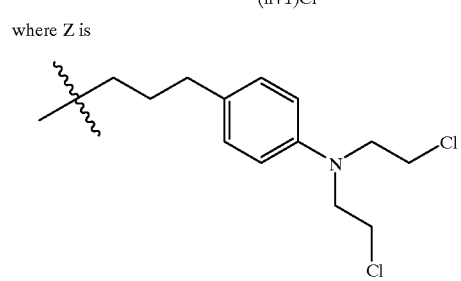

and n is the charge on the metal M, and M is 2H⁺ or a metal cation selected from the group consisting of Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb and Eu.

8. The method of any of claims 1, 5, or 7 wherein the telomeric DNA is a G-quadruplex.

9. The method of any of claims 1, 5, or 7 wherein the telomerase is human telomerase.

10. A compound having a formula:

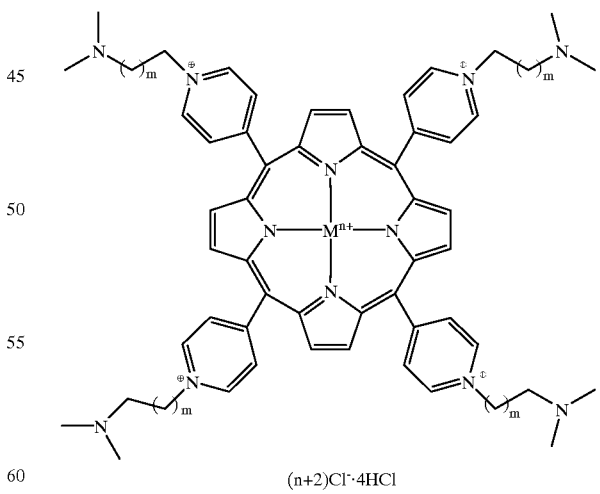

where m is 0–3, n is the charge on the metal ion M, and M is 2H⁺ or a metal cation selected from the group consisting of Ca, Sc, Mn, Fe, Co, Ni, Cu, Zn, Sr, Y, Ru, Pd, Ag, In, Ba, La, Pt. Au, Gd, Mg, TiO, VO, Sn, In, Al, Ga, Er, Gd, Yb, Lu, Pr, Tb and Eu.

11. A compound having the formula:
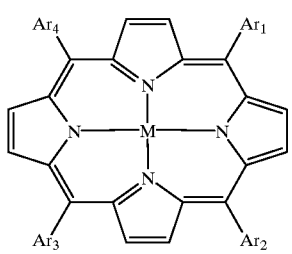
where Ar$_1$, Ar$_2$, Ar$_3$ and Ar$_4$ are selected from the group consisting of
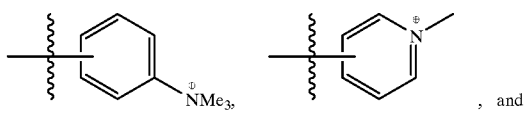, and
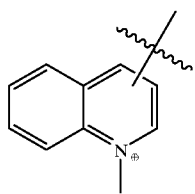
except that Ar$_1$, Ar$_2$, Ar$_3$ and Ar$_4$ are not identical;
or where Ar$_1$, Ar$_2$, Ar$_3$ and Ar$_4$ are independently:
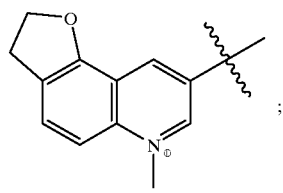;
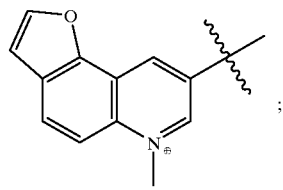;
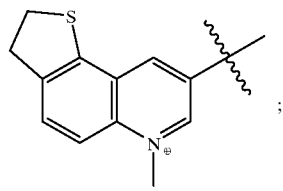;
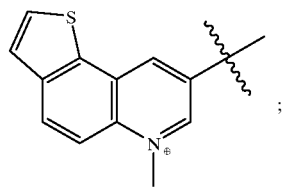;
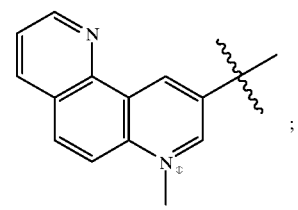;
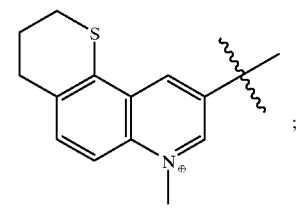;
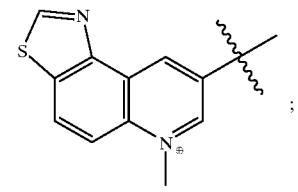;
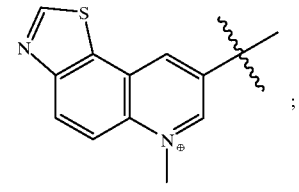;
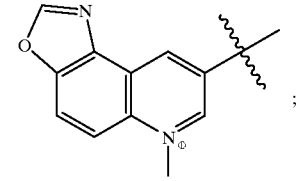;
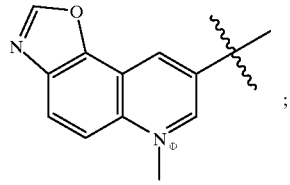;
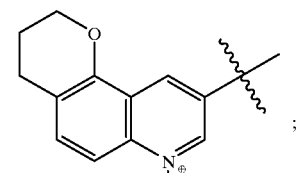;
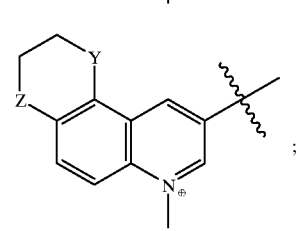;

-continued
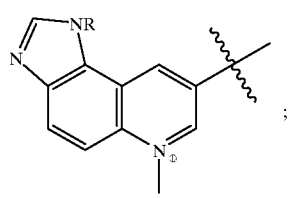
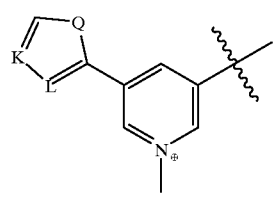
where Q is O, S, NH or NMe; K=CH, N, L=N, CH,
R is lower alkyl, Y and Z are independently CH, NH, NMe, O or S;
or where Ar₁, Ar₂, Ar₃ and Ar₄ are independently:
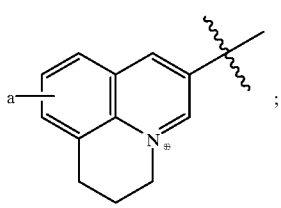
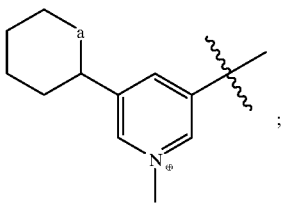
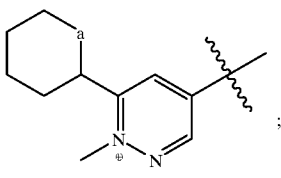
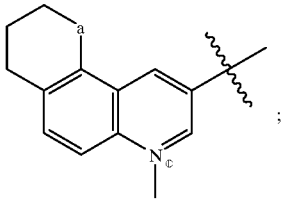
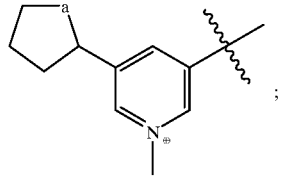
-continued
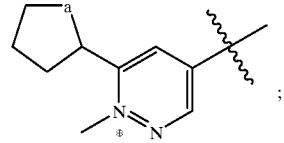
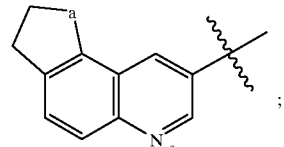
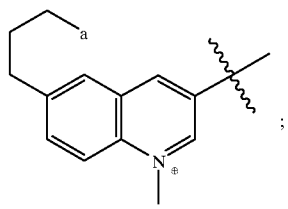
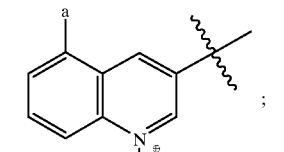
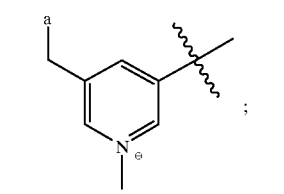
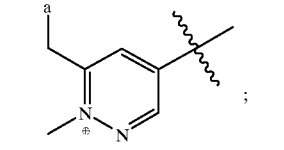
Where Q = O, S, NH or NMe
K = CH or N
L = N or CH
or
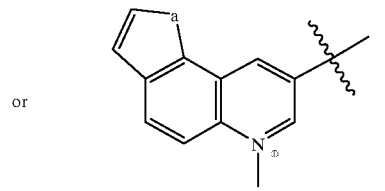
where a is NH, NH₂, NHMe, NMe₂, NMe, OH, OMe, SMe, O or S;
and M is $2H^+$ or a metal ion selected from the group consisting of Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb and Eu; and salts thereof.

12. A compound having a structure:

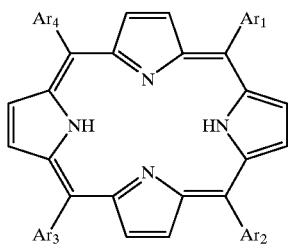

where $Ar_1$, $Ar_2$, $Ar_3$, and $Ar_4$ are selected from the group consisting of:

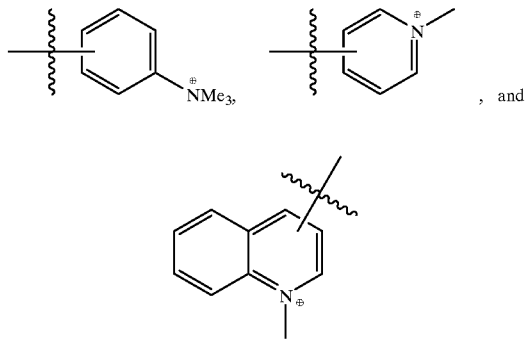

and salts thereof except that $Ar_1$, $Ar_2$, $Ar_3$, and $Ar_4$ are not identical.

13. A pharmaceutical composition comprising the compound of claim 11 or claim 12.

14. A method of inhibiting cell proliferation comprising contacting said cell with an effective amount of a porphyrin.

15. The method of claim 14 wherein the cell is a cancer cell.

16. The method of claim 14 wherein the porphyrin is tetra(N-methyl-4-pyridyl)porphine.

17. The method of claim 14 wherein the porphyrin is Pt(II) tetra(N-methyl-4-pyridyl)porphyrin, or Cu (II) tetra (N-methyl4-pyridyl)porphyrin.

18. The method of claim 15 wherein the cancer cell is a prostate or lymphoma cell.

19. The method of claim 15 wherein the cancer is a breast cancer cell.

20. The method of claim 19 wherein the breast cancer cell is a BT20, MCF-7m, 11S578t, HS576Bst or Hela cell.

21. The method of claim 14 wherein the cell is in a mammal.

22. A porphyrin which is diethylene glycol di-[5-(3-hydroxyphenyl)-10,15,20-tri-(4-pyridyl)]-porphine; tetra-ethylene glycol di-[5-(3-hydroxyphenyl)-10,15,20-tri-(4-pyridyl)]-porphine, pentaethylene glycol di-[5-(3-hydroxyphenyl)-10,15,20-tri-(4-pyridyl)]-porphine, hexaethylene glycol di-[5-(3-hydroxyphenyl)-10,15,20-tri-(4-pyridyl)]-porphine or 5-(3-ethylcarbonyloxyphenyl)-10,15,20-tri(N-methyl4pyridyl)]porphine and quaternary ammonium salts thereof.

23. A porphyrin having the formula:

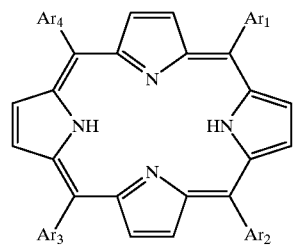

in which:

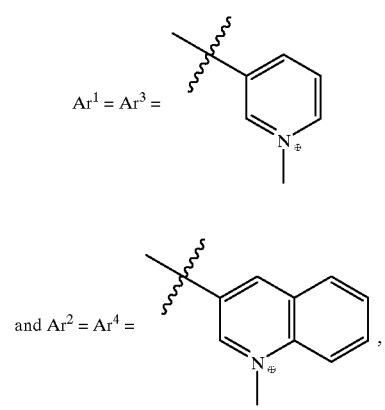

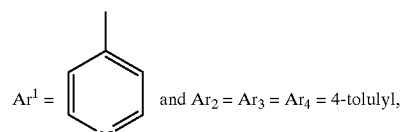

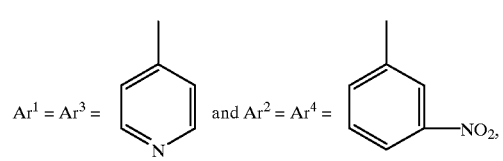

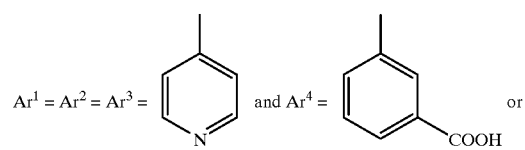

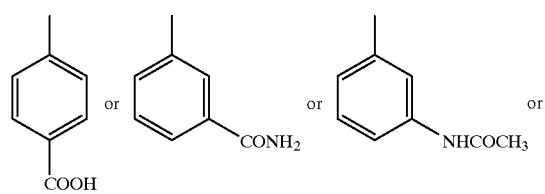

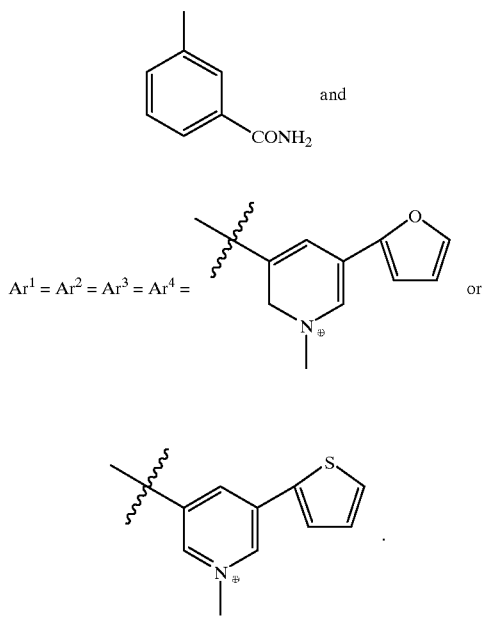

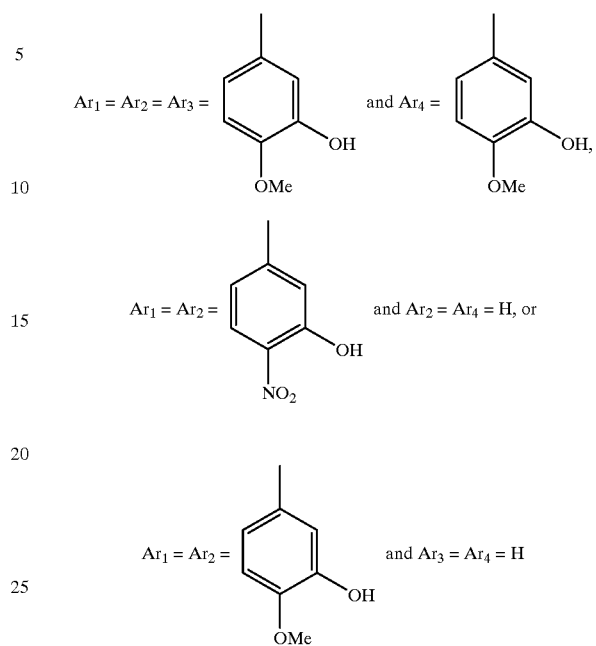

24. A porphine of the formula:

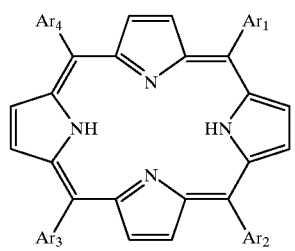

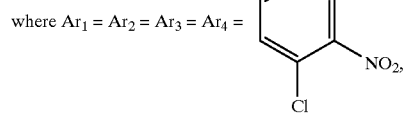

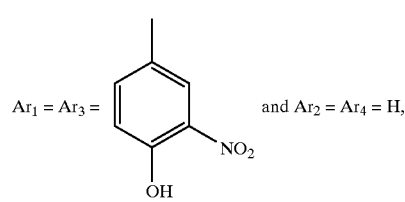

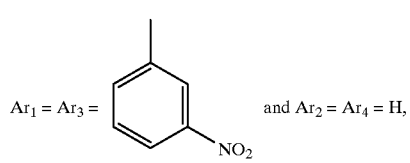

25. A porphyrin quaternary ammonium compound which is selected from the group consisting of 5,10,15-tri-(N-methyl-3-quinolyl)-20-(N-methyl-3-pyridyl)porphine; 5,10,15-tri-(N-methyl-4-pyridyl)-20-(3-nitrophenyl)porphine; 5,10-di-(N-methyl-4-pyridyl)-15,20-(3-carboxyphenyl)porphine; 5,10-di-(N-methyl-4-pyridyl)porphine and 15,20-di-(3-[2-bromoethylcarboxamido]phenyl)porphine.

26. The porphyrin quaternary ammonium salt of claim 25 wherein the porphine quaternary compound is a chloride salt.

27. A porphyrin having the formula:

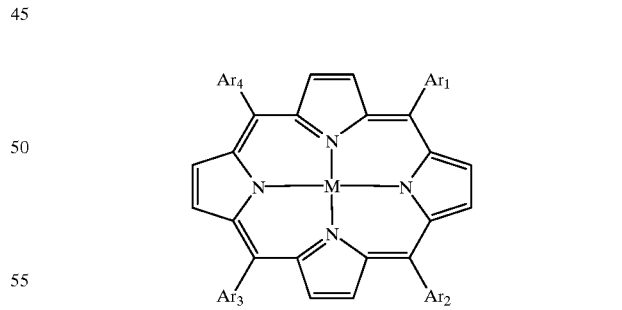

wherein $Ar_1$, $Ar_2$, $Ar_3$ and $Ar_4$ are positively charged moieties, are not identical, and assume a planar disposition with regard to said porphyrin structure.

28. A method of modifying telomerase or telomere function, comprising interacting a porphyrin with telomeric DNA wherein the porphyrin has a formula:

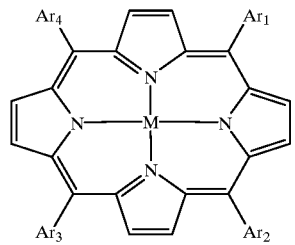

wherein $Ar_1$, $Ar_2$, $Ar_3$ and $Ar_4$ are positively charged moieties, are not identical, and assume a planar disposition with regard to said porphyrin structure.

29. A method of inhibiting proliferation of a cell comprising contacting said cell with porphyrin having the formula:

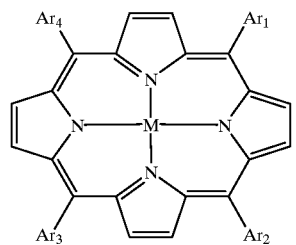

wherein $Ar_1$, $Ar_2$, $Ar_3$ and $Ar_4$ are positively charged moieties, are not identical, and assume a planar disposition with regard to said porphyrin structure.

* * * * *

UNITED STATES PATENT AND TRADEMARK OFFICE
CERTIFICATE OF CORRECTION

PATENT NO. : 6,087,493
DATED : July 11, 2000
INVENTOR(S) : Wheelhouse et al.

Page 1 of 5

It is certified that error appears in the above-identified patent and that said Letters Patent is hereby corrected as shown below:

BRIEF DESCRIPTION OF THE DRAWINGS,
Column 12,
Please delete lines 1-2.
Line 3, please delete "FIG. 9A" and insert therefor -- FIG. 8A --.
Line 7, please delete "FIG. 9B" and insert therefor -- FIG. 8B --.
Line 11, please delete "FIG. 9C" and insert therefor -- FIG. 8C --.
Line 15, please delete "FIG. 10" and insert therefor -- FIG. 9 --.
Line 17, please delete "FIG. 11" and insert therefor -- FIG. 10 --.
Lines 20-21, please delete lines 13 and 14, and insert -- FIGS. 11A AND 11B.

Figure 6A:
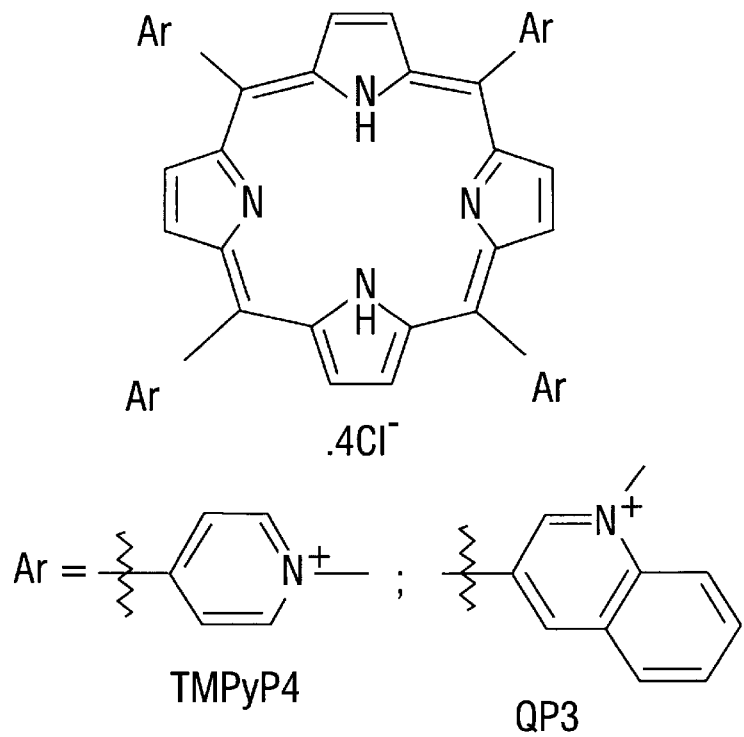
Figure 6B:
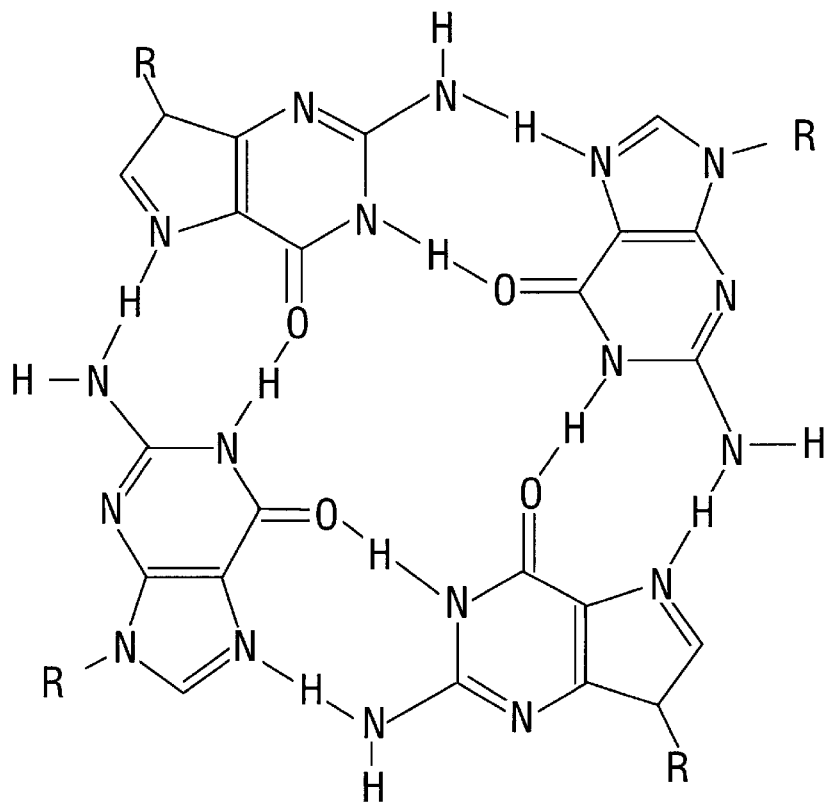
Figure 6C:
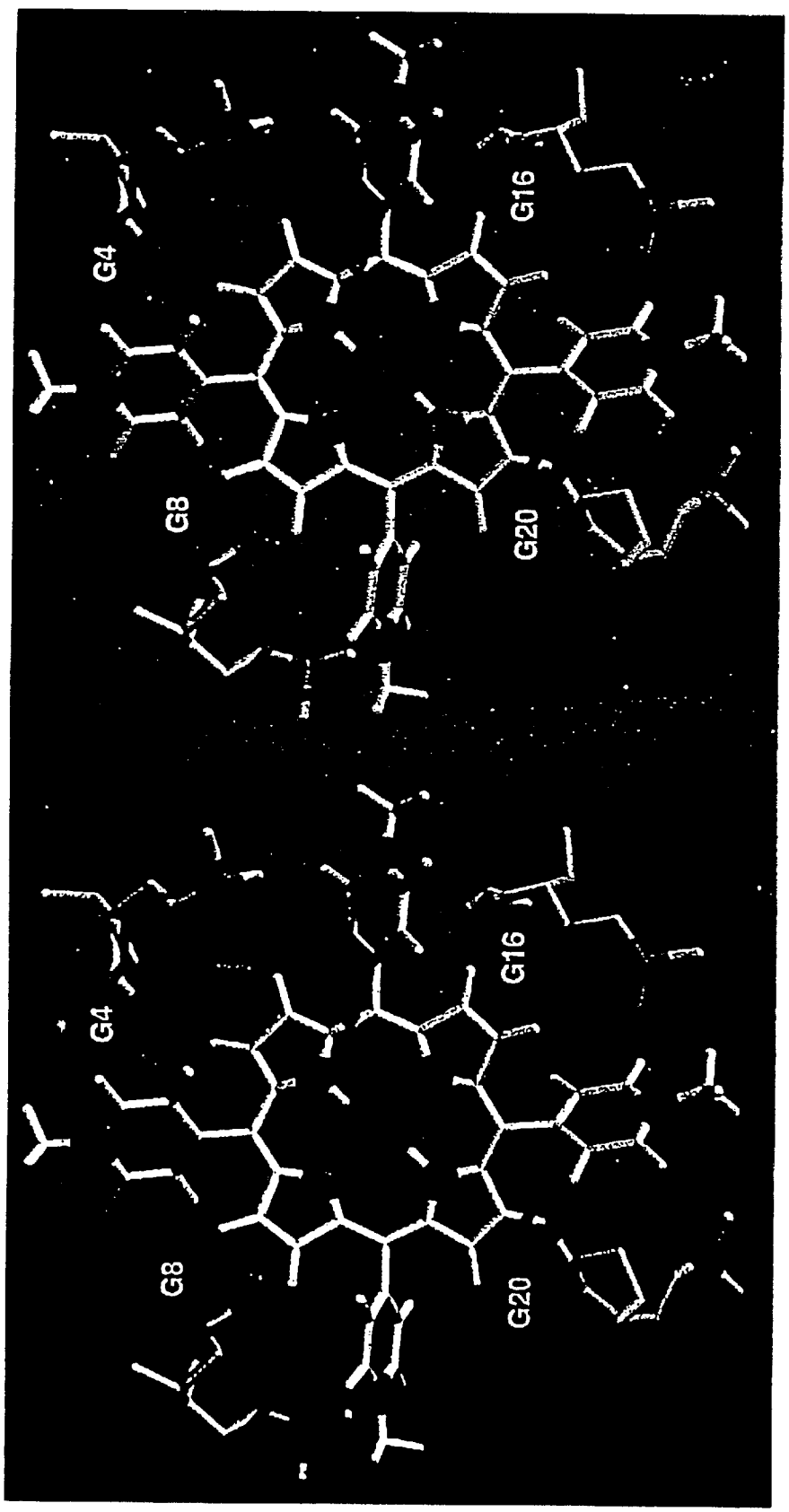
Figure 7A:
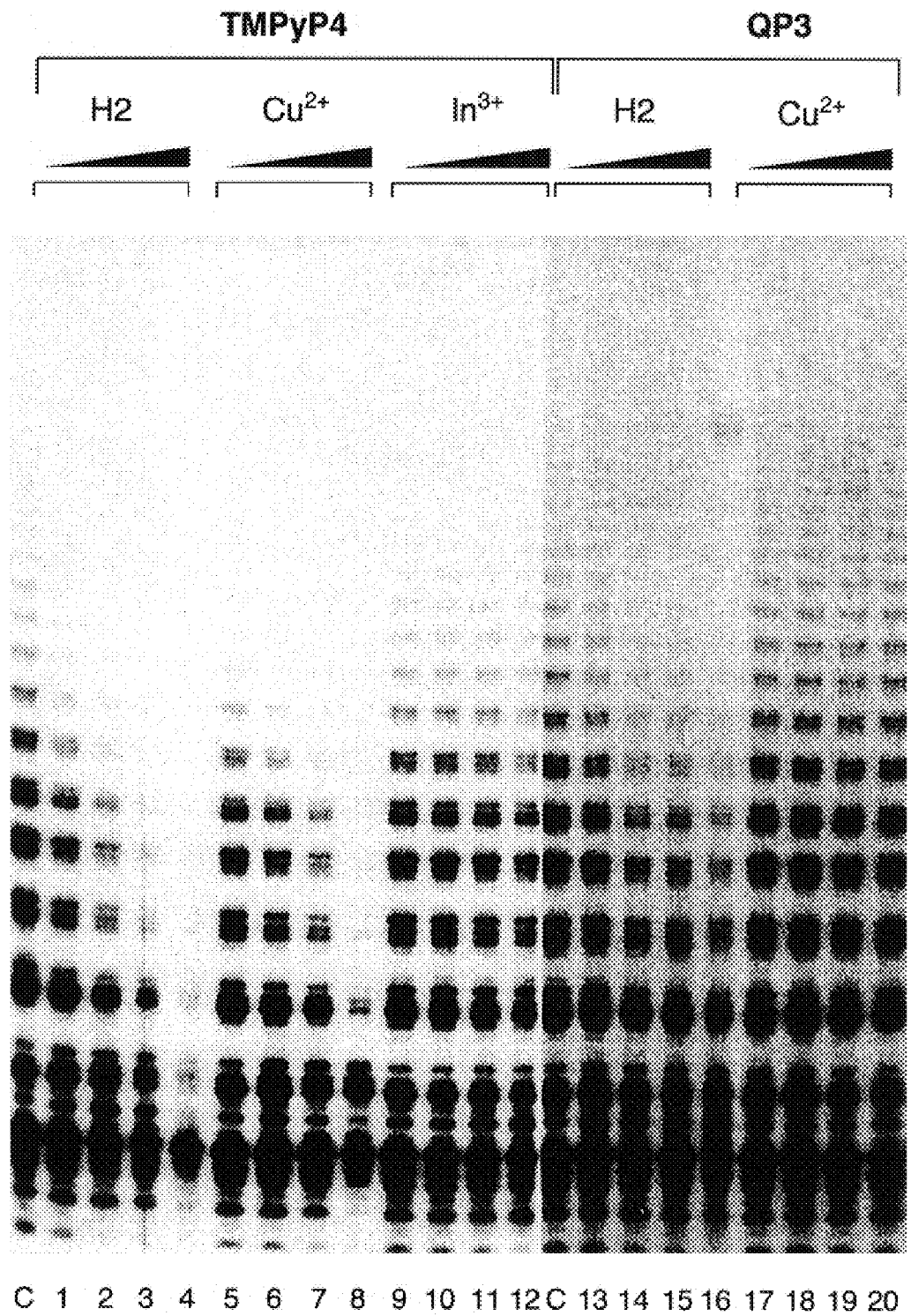
Figure 7B:
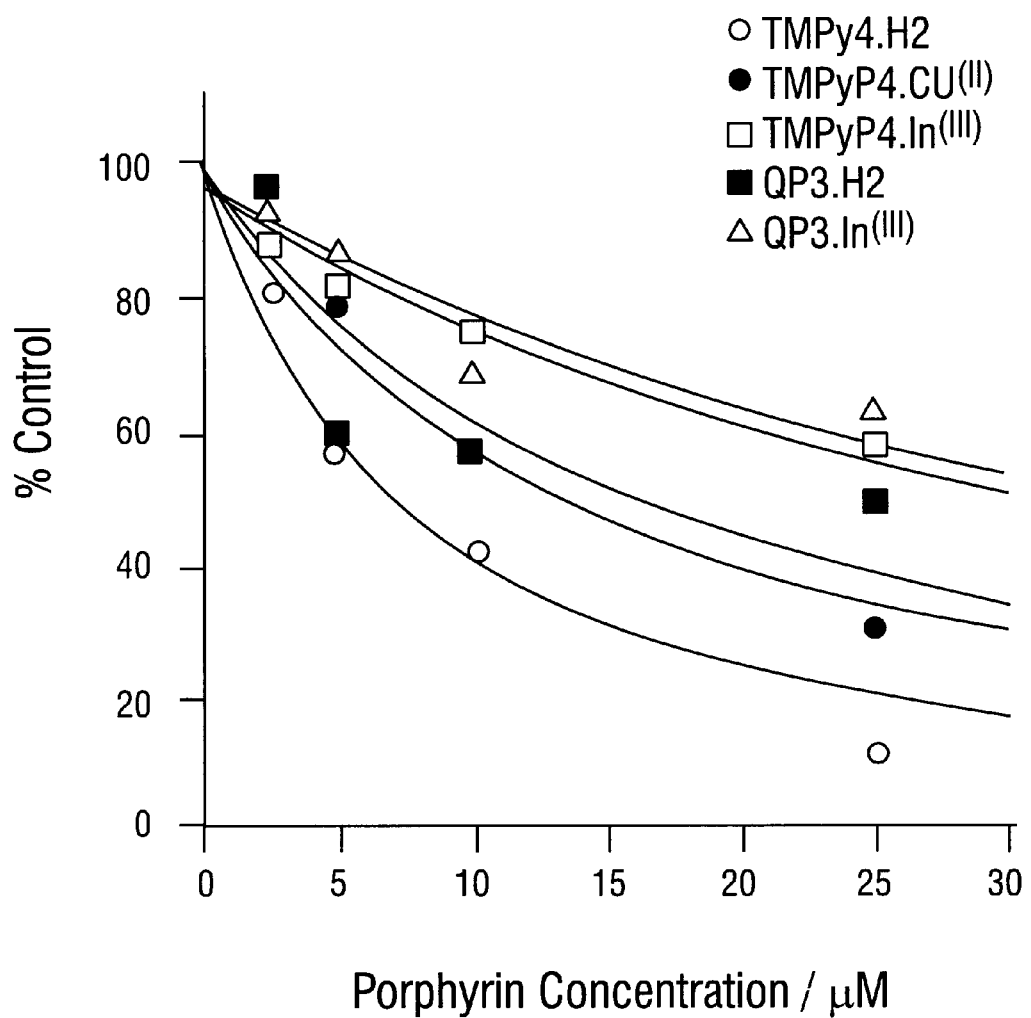

Column 15,
Line 48, please delete "FIG. 7" and insert therefor -- FIG. 6 --.
Line 49, please delete both instances of "FIG. 7" and insert therefor -- FIG. 6 --.
Lines 57-58, please delete "FIG. 7C" and insert therefor -- FIG. 6C --.

Figure 1:
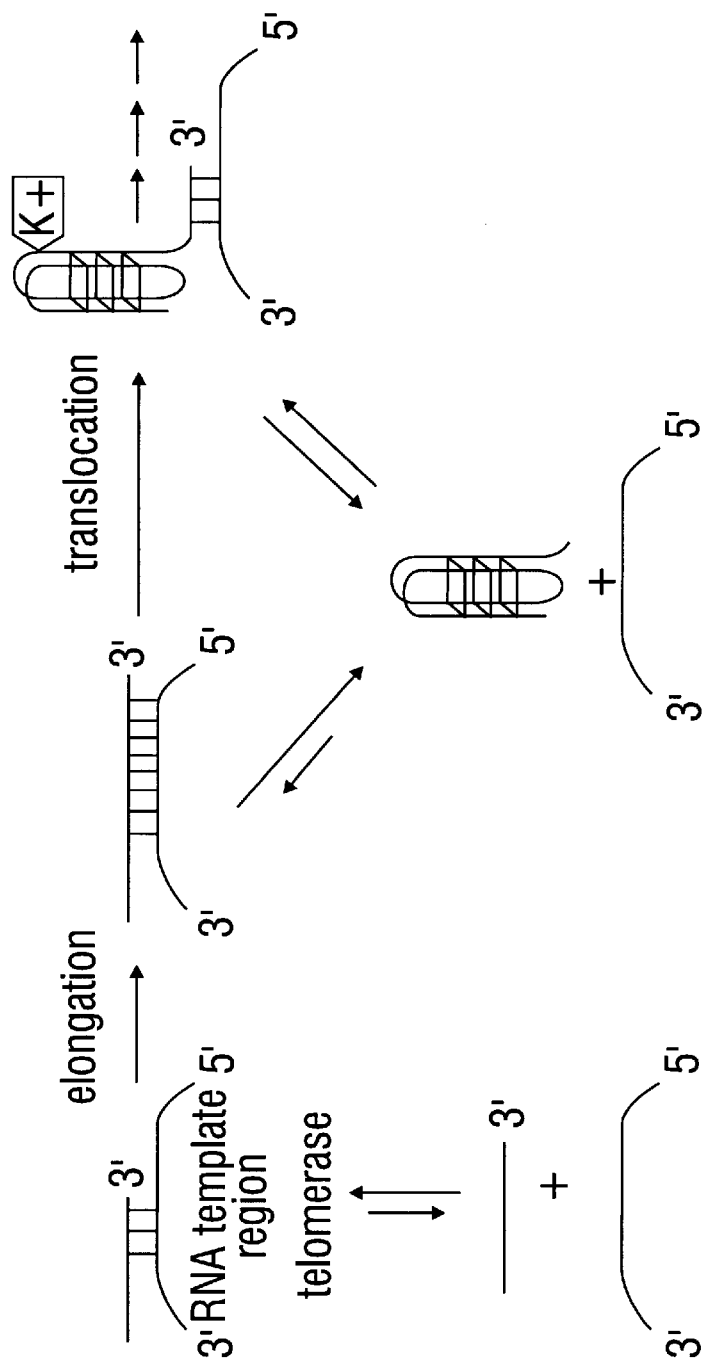
Figure 2:
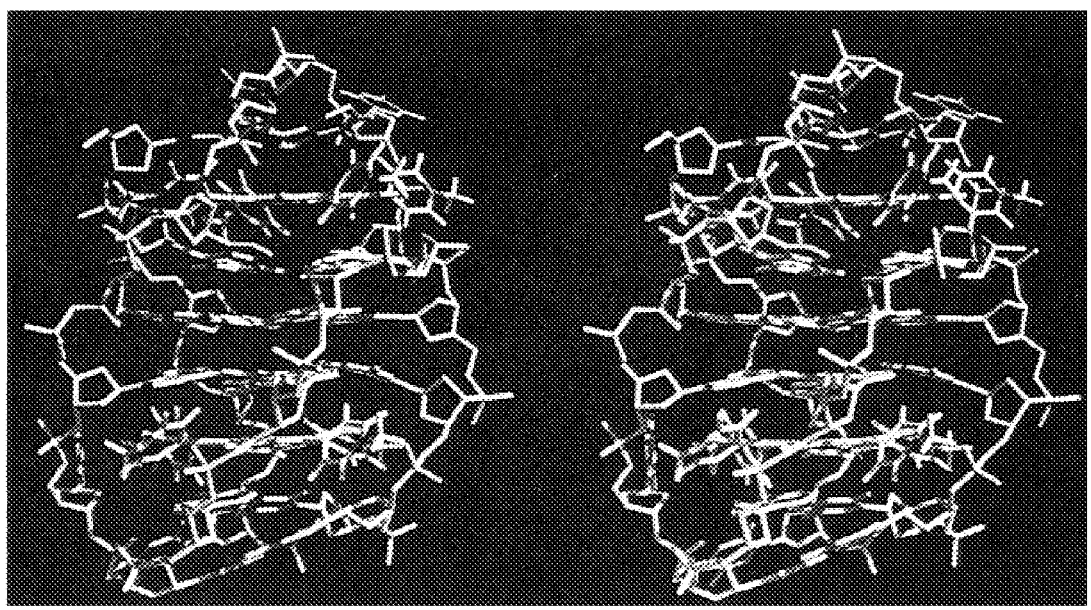
Figure 3:
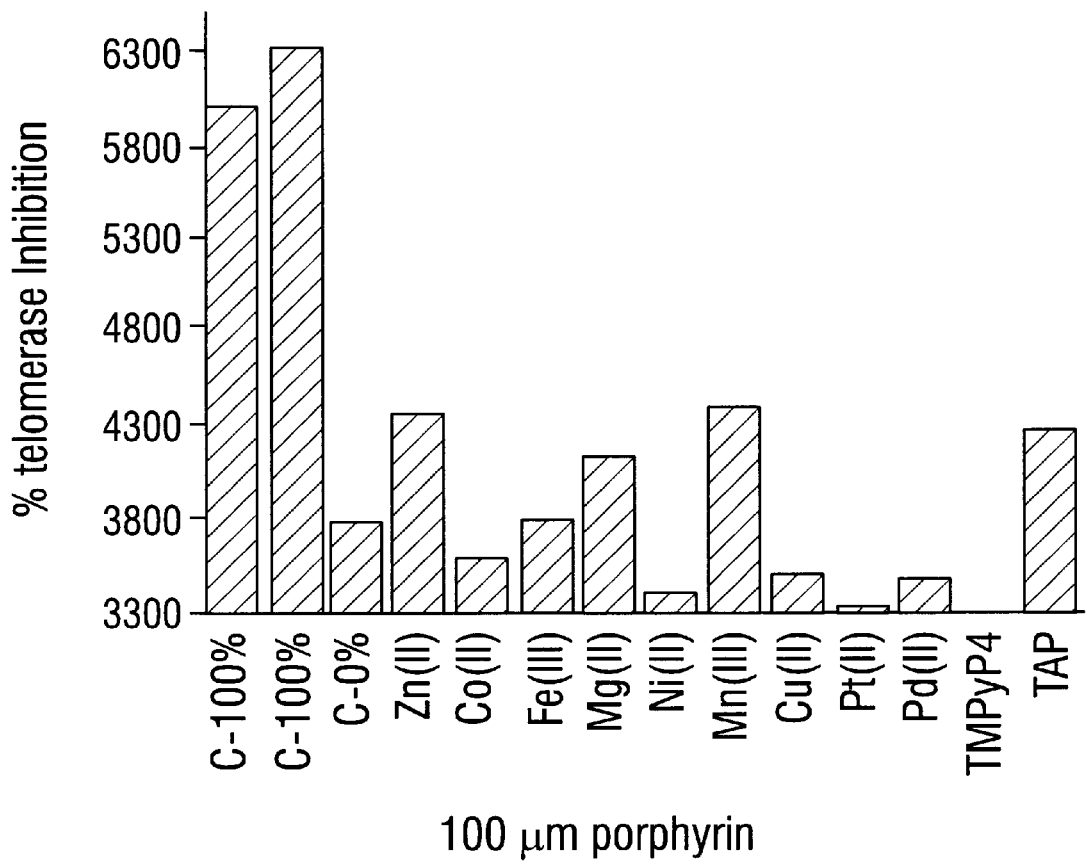
Figure 4A:
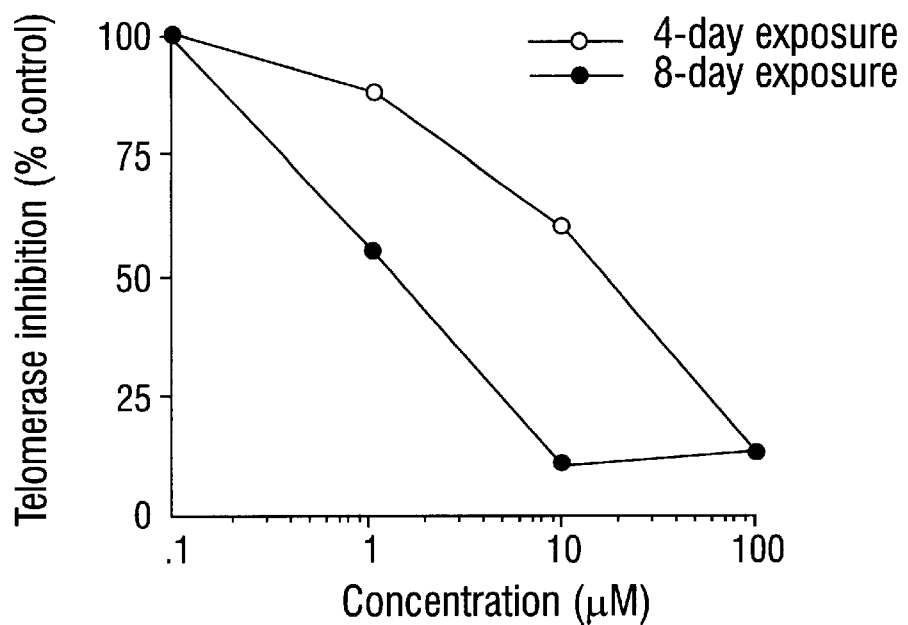
Figure 4B:
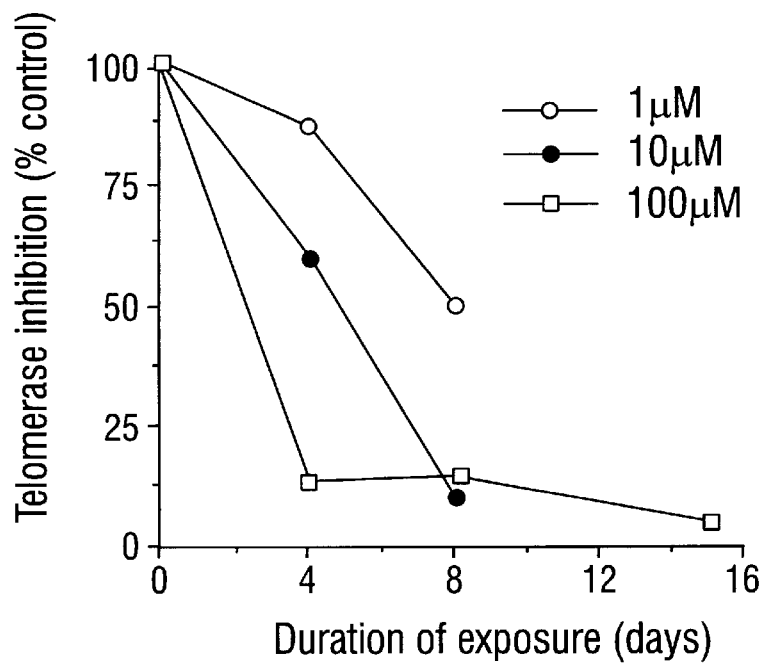
Figure 5A:
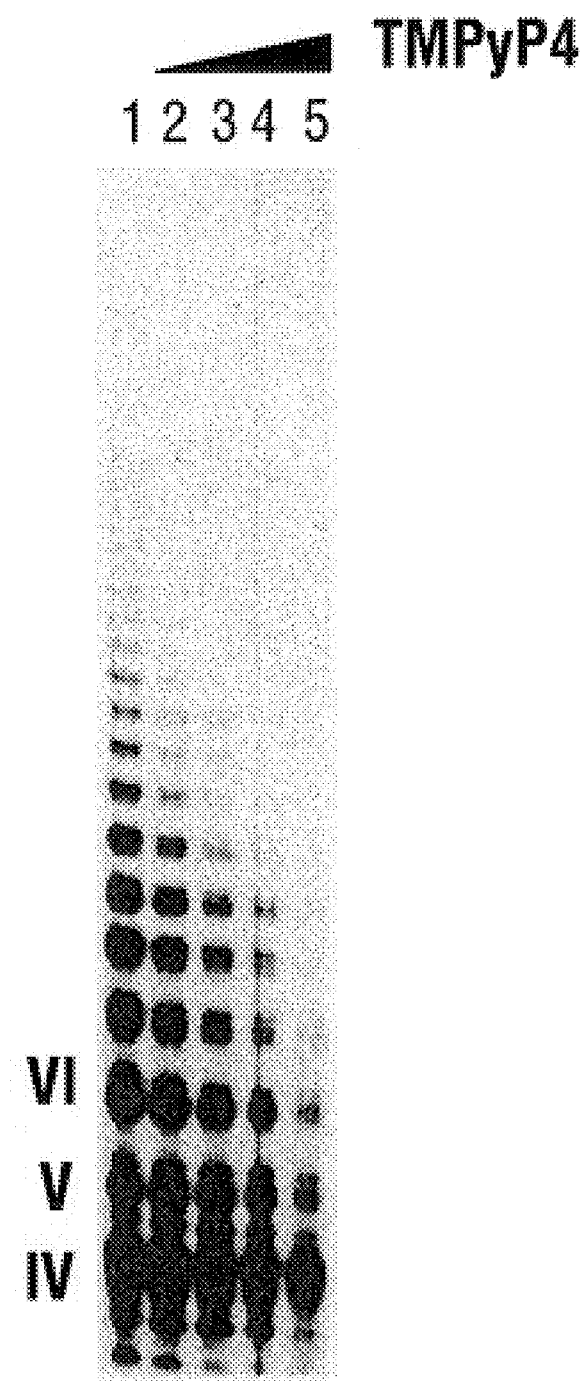
Figure 5B:
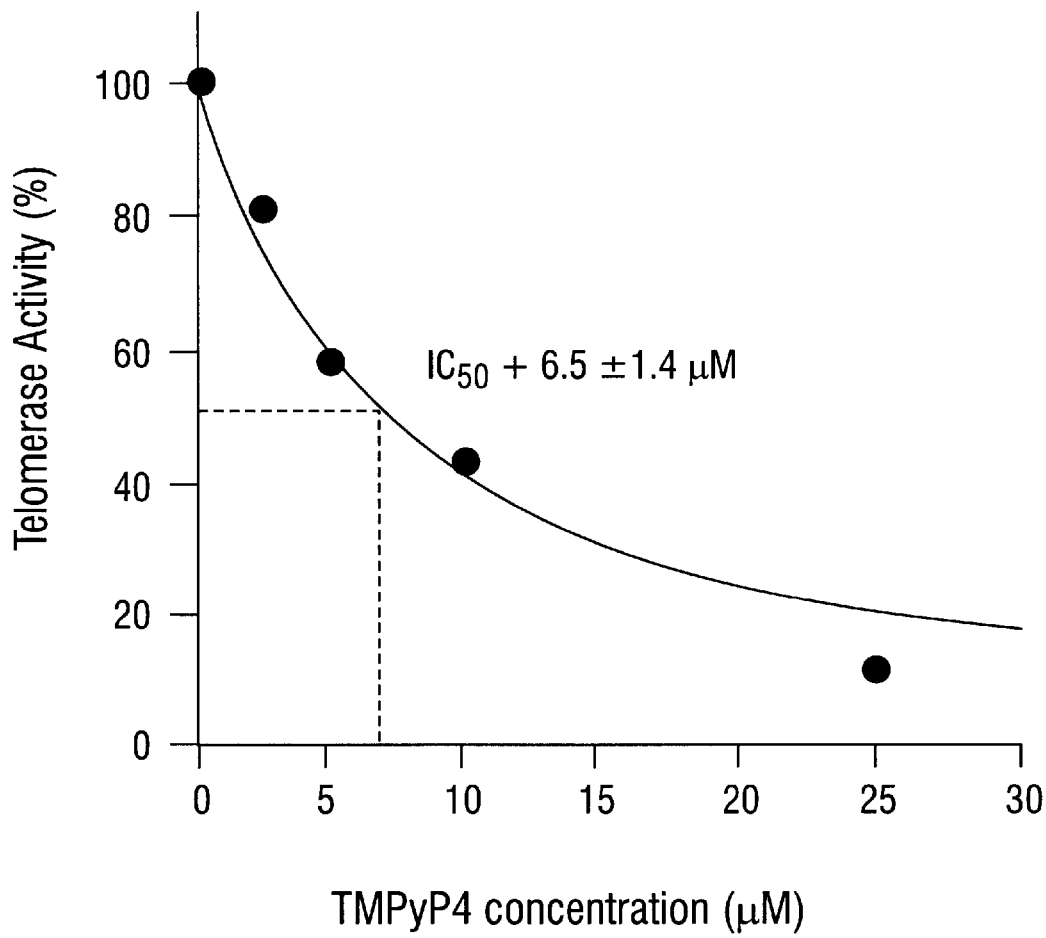

Column 29,
Line 45, please delete "FIG. 6B" and insert therefor -- FIG. 5B --.

UNITED STATES PATENT AND TRADEMARK OFFICE
CERTIFICATE OF CORRECTION

PATENT NO. : 6,087,493
DATED : July 11, 2000
INVENTOR(S) : Wheelhouse et al.

Figure 8A:
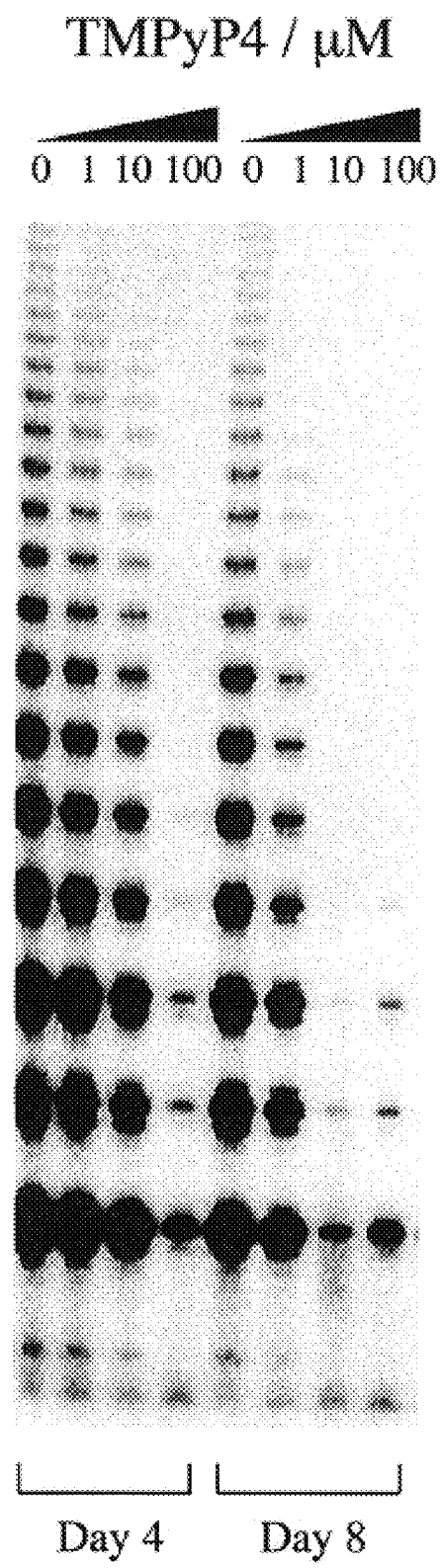
Figure 8B:
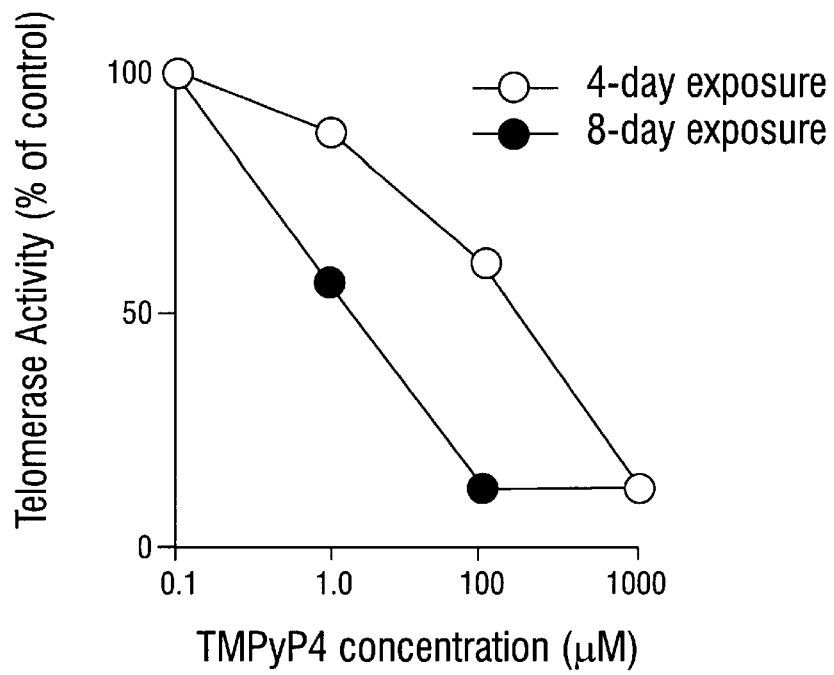
Figure 8C:
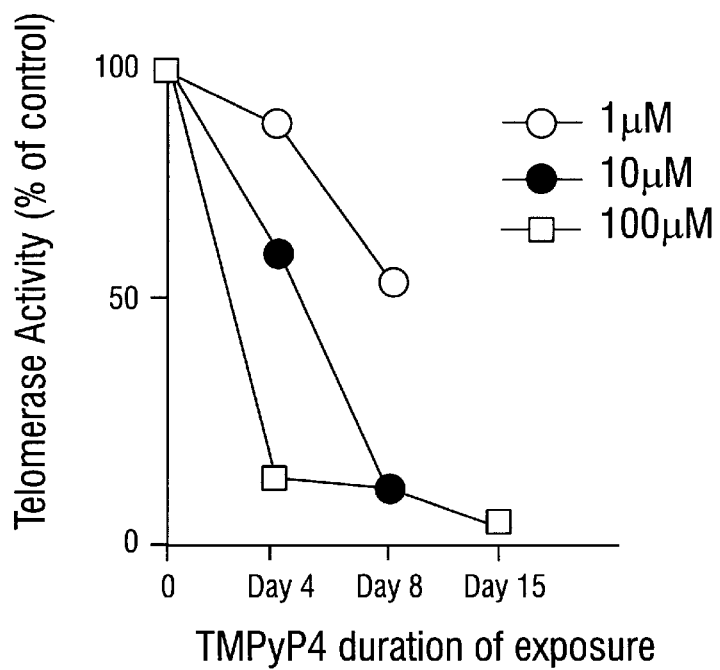
Figure 9:
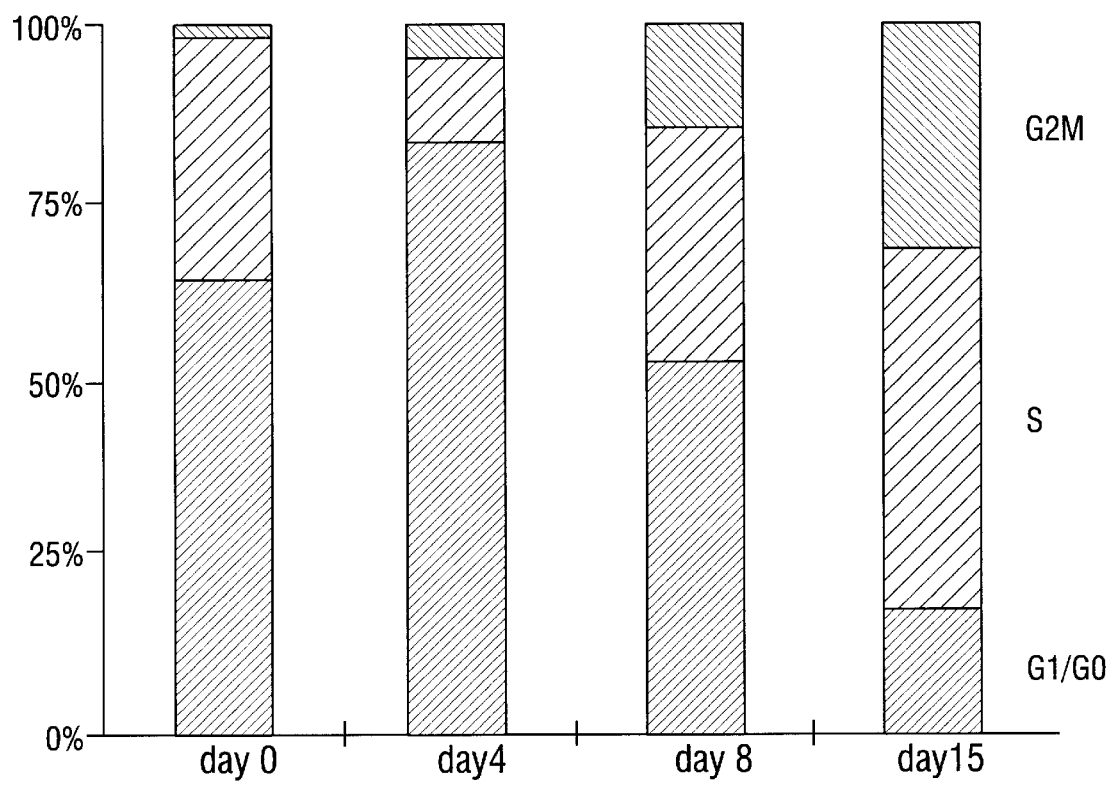

It is certified that error appears in the above-identified patent and that said Letters Patent is hereby corrected as shown below:

Column 39,
Line 21, please delete "(FIG. 8)".
Line 35, please delete "(FIG. 9A)" and insert therefor -- (FIG. 8A) --.
Line 36, please delete "(FIG. 9B)" and insert therefor -- (FIG. 8B) --.
Line 38, please delete "(FIG. 9C)" and insert therefor -- (FIG. 8C) --.
Line 61, please delete "FIG. 10" and insert therefor -- FIG. 9 --.

Figure 12A:
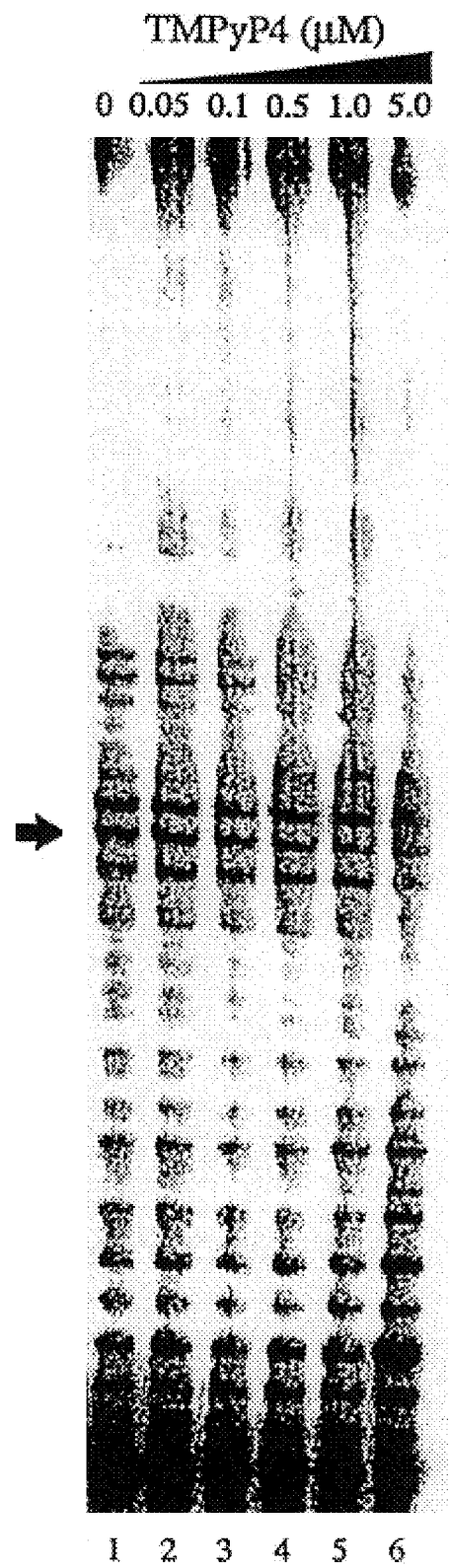
Figure 13A:
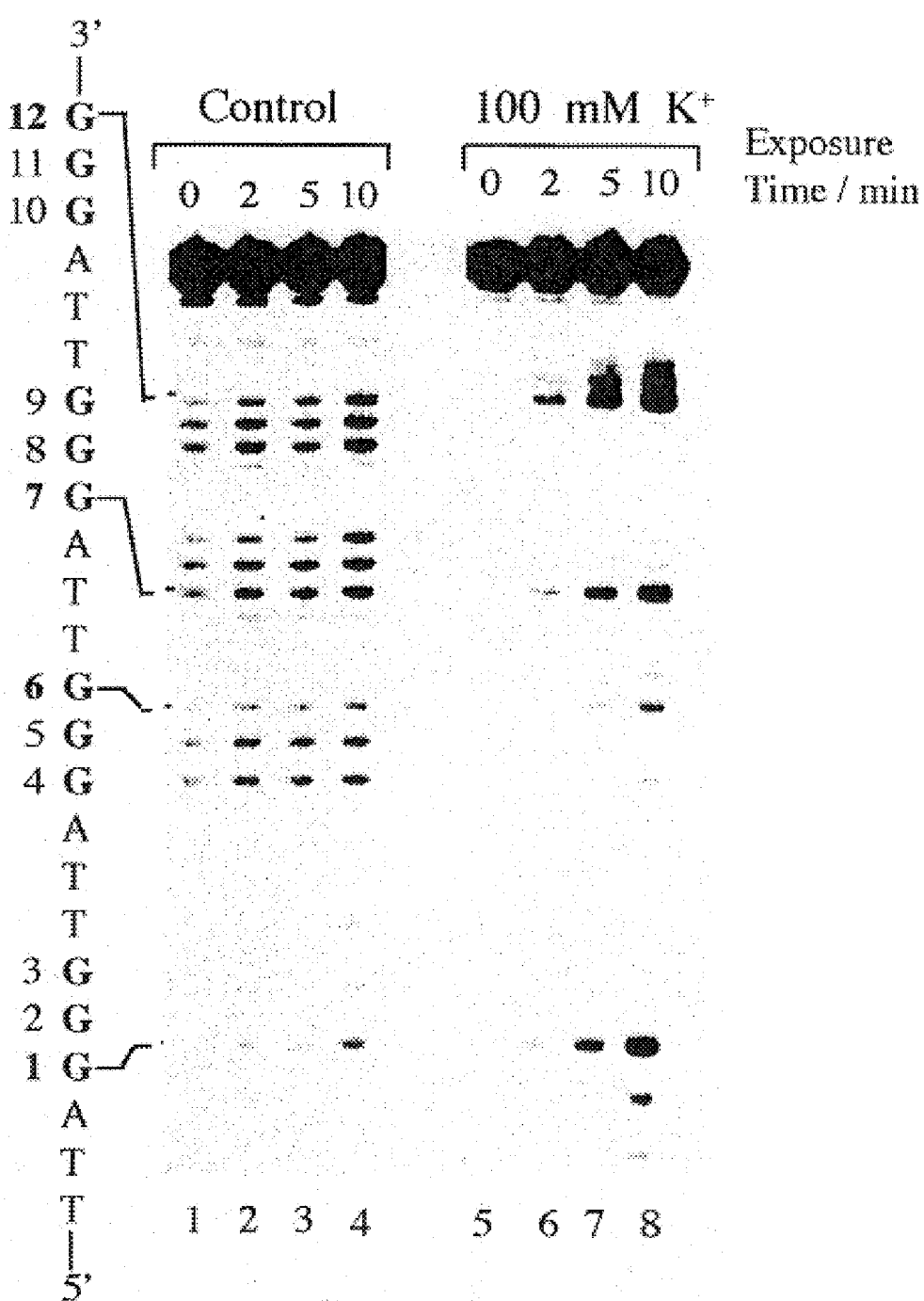
-- FIG. 13A. Photosensitizing activity of porphyrins used to probe binding site of TMPPyP4 on quadruplex DNA. Cleavage patterns of single-stranded DNA bearing four telomeric repeats treated with TMP4P4 and subject to light exposure. Lanes 1-4 show uniform cleavage at purines in the absence of potassium ions, vs. lanes 5-8 where the presence of 100mM KCI favor quadruplex formation and show cleavage selectability at the 5'-ApG-3' step at G1 and G7, and the 5'-GpT-3' step at G6 and G12.

Column 41,
Line 38, please delete "FIG. 5A" and insert therefor -- FIG. 13A --.
Line 47, please delete "FIG. 5B" and insert therefor -- FIG. 13B --.,
Line 63, please delete "FIG. 13A" and insert therefor -- FIG. 12A --.

Figure 12B:
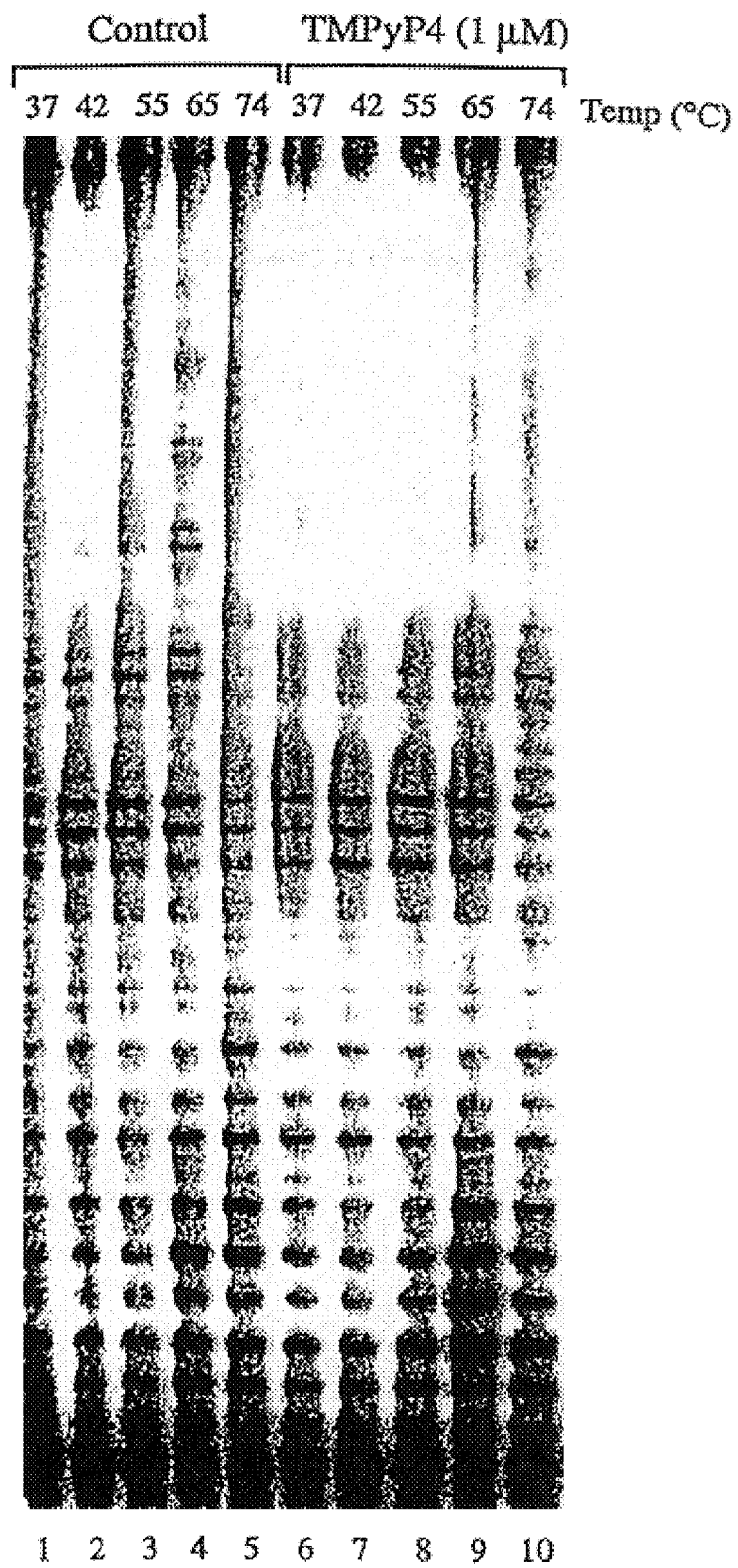
Figure 13B:
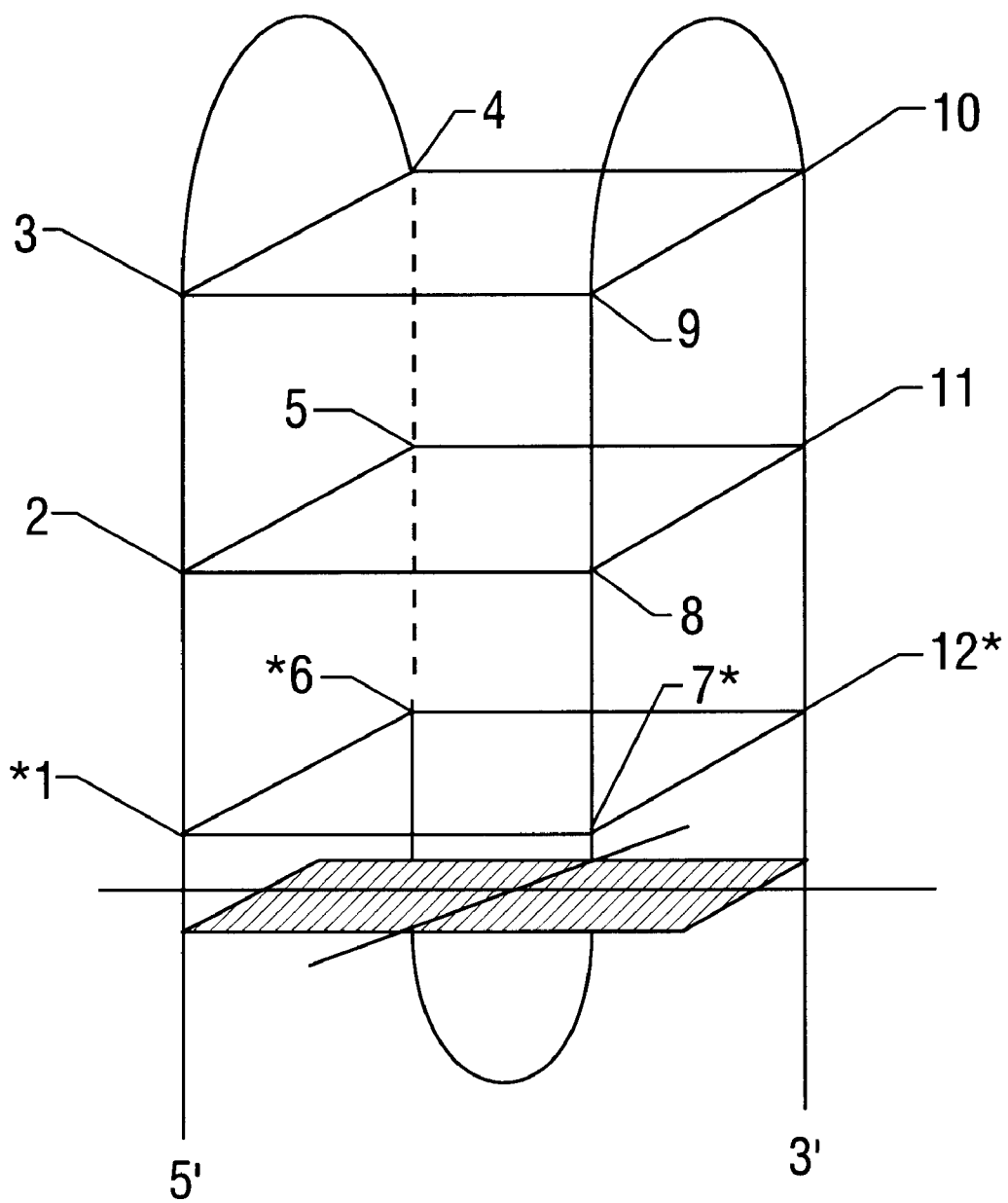
FIG. 13B Shows an example fold depicting that G1, G6, G7 and G12 are members of the same tetrad. -- therefor.

Column 42,
Line 6, please delete both instances of "FIG. 13B" and insert therefor -- FIG. 12B --.

Figure 10:
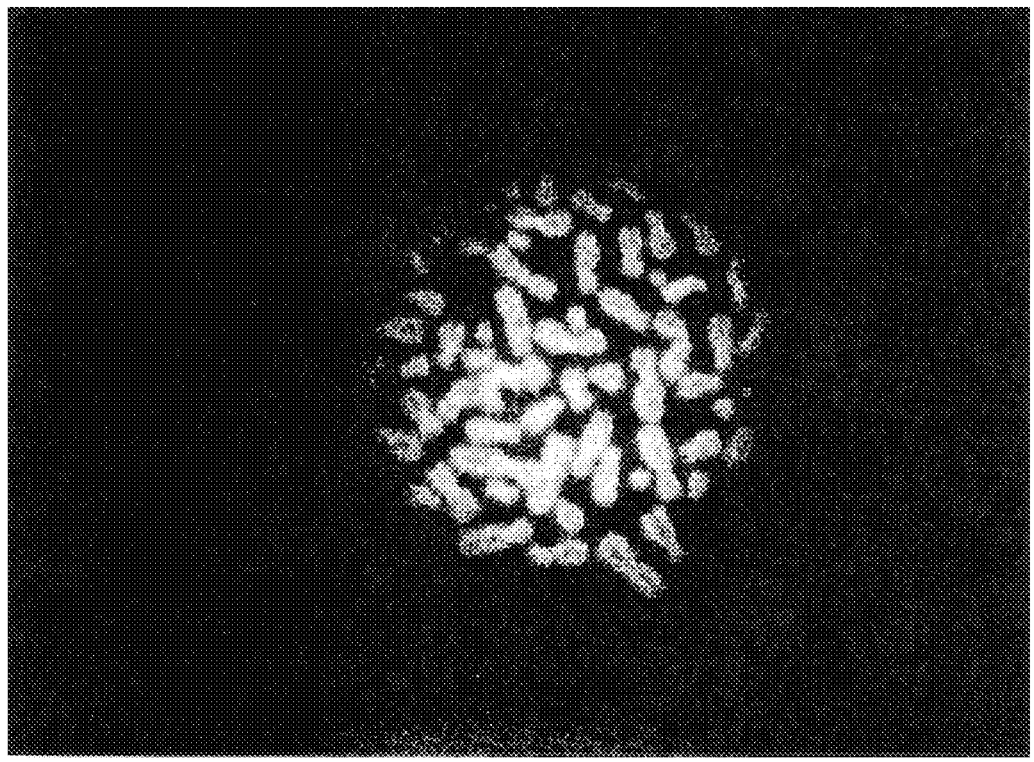
Figure 11A:
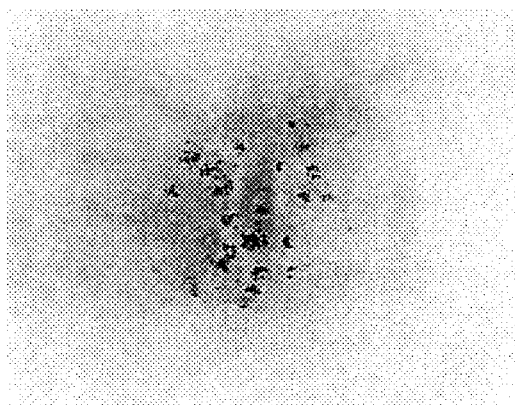
FIG. 11A shows control sea urchin embryo.
Figure 11B:
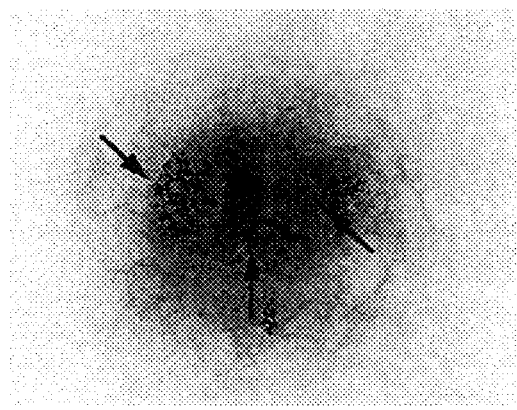
FIG. 11B shows chromosomal destabilization induced by 100 μM TMPyP4 in sea urchin embryos. -- therefor.
Line 22, please delete "FIG. 13A" and insert therefor -- FIG. 12A --.
Line 26, please delete "FIG. 13B" and insert therefor -- FIG. 12B --.
After line 30, please add.

Column 43,
Line 15, please delete "FIG. 11" and insert therefor -- FIG. 10 --.
Line 37, please delete "FIG. 12" and insert therefor -- FIGS. 11A and 11B --.

Column 79, claim 1,
Line 64, please delete "NHCOCH$_3$," and insert -- NHCOCH$_3$; -- therefor.

Column 81, claim 1,
Line 52, please delete "K=CN, N, L=N, CH" and insert -- K is CN or N; L is N or CH -- therefor.
Line 53, please delete "A is CH," and insert -- Y and Z are independently CH$_2$, -- therefor.
Line 54, please delete "independently;" and insert -- independently -- therefor.

UNITED STATES PATENT AND TRADEMARK OFFICE
CERTIFICATE OF CORRECTION

PATENT NO. : 6,087,493
DATED : July 11, 2000
INVENTOR(S) : Wheelhouse et al.

Page 3 of 5

It is certified that error appears in the above-identified patent and that said Letters Patent is hereby corrected as shown below:

Column 83, claim 1,
Line 24, please delete "independently;" and insert -- independently -- therefor.
Lines 25-30, please delete the two figures in insert the figures:

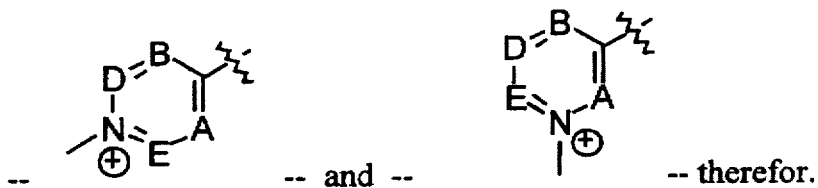

-- and -- -- therefor.

Column 83, claim 1,
Lines 49-51, please delete "Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb, Eu" and insert -- Ca, Sc, Mn, Fe, Co, Ni, Cu, Zn, Sr, Y, Ru, Pd, Ag, In, Ba, La, Pt, Au, Mg, TiO, VO, Sn, Al, Ga, Er, Gd, Yb, Lu, Pr, Tb, Eu -- therefor.

Column 84, claim 1,
Line 14, please delete "$Ar^1$, $A^2$, $Ar^3$ and $Ar_4$" and insert -- $Ar_1$, $Ar_2$, $Ar_3$ and $Ar_4$ -- therefor.

Column 84, claim 5,
Line 25, please delete "0-3. X is O, NH, CO, or" and insert -- 0-3, X is O, NH, CO, or $CH_2$, and where ligand is: -- therefor.

Column 85, claim 5,
Line 25, please delete the phrase "$CH_2$, and where ligand is" therefor.
Lines 26-29, please delete "Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb, Eu" and insert -- Ca, Sc, Mn, Fe, Co, Ni, Cu, Zn, Sr, Y, Ru, Pd, Ag, In, Ba, La, Pt, Au, Mg, TiO, VO, Sn, Al, Ga, Er, Gd, Yb, Lu, Pr, Tb, Eu -- therefor.

Column 85, claim 6,
Lines 60-63, please delete "Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb, Eu" and insert -- Ca, Sc, Mn, Fe, Co, Ni, Cu, Zn, Sr, Y, Ru, Pd, Ag, In, Ba, La, Pt, Au, Mg, TiO, VO, Sn, Al, Ga, Er, Gd, Yb, Lu, Pr, Tb, Eu -- therefor.

UNITED STATES PATENT AND TRADEMARK OFFICE
CERTIFICATE OF CORRECTION

PATENT NO. : 6,087,493
DATED : July 11, 2000
INVENTOR(S) : Wheelhouse et al.

It is certified that error appears in the above-identified patent and that said Letters Patent is hereby corrected as shown below:

Column 86, claim 7,
Lines 33-36, please delete "Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb, Eu" and insert -- Ca, Sc, Mn, Fe, Co, Ni, Cu, Zn, Sr, Y, Ru, Pd, Ag, In, Ba, La, Pt, Au, Mg, TiO, VO, Sn, Al, Ga, Er, Gd, Yb, Lu, Pr, Tb, Eu -- therefor.

Column 86, claim 10,
Lines 65-67, please delete "Ca, Sc, Mn, Fe, Co, Ni, Cu, Zn, Sr, Y, Ru, Pd, Ag, In, Ba, La, Pt, Au, Gd, Mg. TiO, VO, Sn, In, Al, Ga, Er, Gd, Yb, Lu, Pr, Tb Eu" and insert -- Ca, Sc, Mn, Fe, Co, Ni, Cu, Zn, Sr, Y, Ru, Pd, Ag, In, Ba, La, Pt, Au, Mg, TiO, VO, Sn, Al, Ga, Er, Gd, Yb, Lu, Pr, Tb, Eu -- therefor.

Column 87, claim 11,
Line 34, please delete "independently:" and insert -- independently -- therefor.

Column 89, claim 11,
Line 19, please delete "K=CN, N, L=N, CH" and insert -- K is CN or N; L is N or CH -- therefor.
Line 21, please delete "CH," and insert -- $CH_2$, -- therefor.

Column 90, claim 11,
Line 66 through column 91, line 2, please delete "Ca, Sc, Mn, Fe, Co, Ni, Cu, Zn, Sr, Y, Ru, Pd, Ag, In, Ba, La, Pt, Au, Gd, Mg, TiO, VO, Sn, In, Al, Ga, Er, Gd, Yb, Lu, Pr, Tb, Eu" and insert -- Ca, Sc, Mn, Fe, Co, Ni, Cu, Zn, Sr, Y, Ru, Pd, Ag, In, Ba, La, Pt, Au, Mg, TiO, VO, Sn, Al, Ga, Er, Gd, Yb, Lu, Pr, Tb, Eu -- therefor.

Column 91, claim 12,
Line 21, please delete "of:" and insert -- of -- therefor.

Column 91, claim 17,
Line 53, please delete "(N-methyl4-pyridyl)" and insert -- (N-methyl-4-pyridyl) -- therefor.

UNITED STATES PATENT AND TRADEMARK OFFICE
CERTIFICATE OF CORRECTION

PATENT NO.    : 6,087,493
DATED         : July 11, 2000
INVENTOR(S)   : Wheelhouse et al.

It is certified that error appears in the above-identified patent and that said Letters Patent is hereby corrected as shown below:

Column 92, claim 22,
Line 4, please delete "(N-methyl4pyridyl)" and insert -- (N-methyl-4-pyridyl) -- therefor.

Column 92, claim 23,
Line 23, please delete "in which:" and insert -- in which -- therefor.

Signed and Sealed this

Nineteenth Day of February, 2002

Attest:

JAMES E. ROGAN
Attesting Officer    Director of the United States Patent and Trademark Office

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:1:

TTAGGGTTAG GGTTAGGG                                    18

(2) INFORMATION FOR SEQ ID NO:2:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:2:

ATTTTTAGGG TTAGGGTTAG GG                               22

(2) INFORMATION FOR SEQ ID NO:3:

(i) SEQUENCE CHARACTERISTICS:
       (A) LENGTH: 6 base pairs
       (B) TYPE: nucleic acid
       (C) STRANDEDNESS: single
       (D) TOPOLOGY: linear (xi) SEQUENCE DESCRIPTION: SEQ ID NO:3:

TTAGGG                                                  6

(2) INFORMATION FOR SEQ ID NO:4:

(i) SEQUENCE CHARACTERISTICS:

```
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

TTAGGGTTAG GGTTAGGGTT AGGG                                           24

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:5:

CATGGTGGTT TGGGTTAGGG TTAGGGTTAG GGTTACCAC                           39

(2) INFORMATION FOR SEQ ID NO:6:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (xi) SEQUENCE DESCRIPTION: SEQ ID NO:6:

TCCAACTATG TATACTTGGG GTTGGGGTTG GGGTTGGGGT TAGCGGCACG CAATTGCTAT    60

AGTGAGTCGT ATTA                                                     74

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

TAATACGACT CACTATAG                                                  18

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:8:

CAAUCCCAAU C                                                         11

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:9:

AGGGTTAGGG TTAGGGTTAG GG                                             22
```